US012740976B2

(12) United States Patent
Chen et al.

(10) Patent No.: US 12,740,976 B2

(45) Date of Patent: Sep. 22, 2026

(54) METHODS AND COMPOSITIONS FOR TREATING CANCER

(71) Applicant: City of Hope, Duarte, CA (US)

(72) Inventors: Jianjun Chen, Temple City, CA (US); Rui Su, Monrovia, CA (US); David Horne, Duarte, CA (US); Xiaolan Deng, Temple City, CA (US); Hongzhi Li, Duarte, CA (US); Jun Xie, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 1163 days.

(21) Appl. No.: 17/627,059

(22) PCT Filed: Jul. 23, 2020

(86) PCT No.: PCT/US2020/043294

§ 371 (c)(1),
(2) Date: Jan. 13, 2022

(87) PCT Pub. No.: WO2021/016464

PCT Pub. Date: Jan. 28, 2021

(65) Prior Publication Data

US 2022/0370434 A1 Nov. 24, 2022

Related U.S. Application Data

(60) Provisional application No. 62/877,444, filed on Jul. 23, 2019.

(51) Int. Cl.

| | |
|---|---|
| ***A61K 31/47*** | (2006.01) |
| ***A61K 31/4178*** | (2006.01) |
| ***A61K 31/473*** | (2006.01) |
| ***A61K 31/495*** | (2006.01) |
| ***A61K 31/497*** | (2006.01) |
| ***A61K 31/704*** | (2006.01) |
| ***A61K 31/7068*** | (2006.01) |
| ***A61K 45/06*** | (2006.01) |
| ***A61P 35/02*** | (2006.01) |
| ***C07D 215/52*** | (2006.01) |
| ***C07D 219/04*** | (2006.01) |
| ***C07D 233/52*** | (2006.01) |
| ***C07D 403/14*** | (2006.01) |

(52) U.S. Cl.

CPC .......... *A61K 31/47* (2013.01); *A61K 31/4178* (2013.01); *A61K 31/473* (2013.01); *A61K 31/495* (2013.01); *A61K 31/497* (2013.01); *A61K 31/704* (2013.01); *A61K 31/7068* (2013.01); *A61K 45/06* (2013.01); *A61P 35/02* (2018.01); *C07D 215/52* (2013.01); *C07D 219/04* (2013.01); *C07D 233/52* (2013.01); *C07D 403/14* (2013.01)

(58) Field of Classification Search

CPC .. A61K 31/47; A61K 31/4178; A61K 31/473; A61K 31/495; A61K 31/497; A61K 31/704; A61K 31/7068; A61K 45/06; A61P 35/02; C07D 215/52; C07D 219/04; C07D 233/52; C07D 403/14

USPC .................................................... 514/255.05

See application file for complete search history.

(56) References Cited

U.S. PATENT DOCUMENTS

| | | | |
|---|---|---|---|
| 4,258,181 A | 3/1981 | Murdock et al. | |
| 11,555,009 B2 * | 1/2023 | Yang et al. | |

FOREIGN PATENT DOCUMENTS

| | | | | |
|---|---|---|---|---|
| CN | 108472280 A | 8/2018 | | |
| GB | 2 009 171 A | 6/1979 | | |
| WO | WO-2017/037022 A1 | 3/2017 | | |
| WO | WO-2018157842 A1 * | 9/2018 | | C07C 229/58 |
| WO | WO-2019073296 A1 * | 4/2019 | | A61K 31/4178 |

OTHER PUBLICATIONS

Su et al., "R-2HG Exhibits Anti-tumor Activity by Targeting FTO/m6 A/MYC/CEBPA Signaling", Cell 172, 90-105 Jan. 11, 2018 a 2017 Elsevier Inc. https://doi.org/10.1016/j.cell.2017.11.031. (Year: 2018).*

Yap et al., "Bisantrene, an Active New Drug in the Treatment of Metastatic Breast Cancer", Cancer Research, 43, (Mar. 1983) 1402-1404 (hereinafter "Yap") (Year: 1983).*

Doaei et al., "Changes In FTO And IRX3 Gene Expression In Obese And Overweight Male Adolescents Undergoing An Intensive Life-style Intervention And The Role Of FTO Genotype In This Interaction" Journal of Translational Medicine. May 24, 2019, vol. 17, No. 1, Article 176; pp. 1-8; (Year: 2019).*

Su et al. R-2HG Exhibits Anti-tumor Activity by Targeting FTO/m6A/MYC/CEBPA Signaling. Cell, Jan. 11, 2018, vol. 172, Nos. 1-2; pp. 90-105 (Year: 2018).*

Xu et al., "FTO Expression Is Associated With The Occurrence Of Gastric Cancer And Prognosis" Oncology Reports. Oct. 2018 , Epub Aug. 14, 2017, vol. 38, No. 4; (Year: 2017).*

PUBCHEM) Bisantrene. Pubchem entry CID 5351322 (Year: 1983).*

Su et al., 2020, Cancer Cell 38, 79-96 Jul. 1, 2020 a 2020 Elsevier Inc. (Year: 2020).*

Olsen et al. Molecular Cell 78, Jun. 18, 2020, 996-998 (Year: 2020).*

Yap et al., Bisantrene, Cancer Research, 43, (Mar. 1983) 1402-1404 (hereinafter "Yap") (Year: 1983).*

PUBCHEM) Bisantrene. PubChem entry CID 5351322 (Year: 2025).*

Su et al. Cell, Jan. 11, 2018, vol. 172, Nos. 1-2; pp. 90-105 (Year: 2018).*

Xu et al., Oncology Reports. Oct. 2018, Epub Aug. 14, 2017, vol. 38, No. 4 (Year: 2017).*

Doaei et al., Journal of Translational Medicine ("Doaei"). vol. 17, Art. No. 176 (2019) (Year: 2019).*

Extended European Search Report mailed on Jul. 20, 2023, for EP Patent Application No. 20844993.4, 15 pages.

(Continued)

*Primary Examiner* — Kortney L. Klinkel
*Assistant Examiner* — Grace Ching Hsu
(74) *Attorney, Agent, or Firm* — Mintz, Levin, Cohn, Ferris, Glovsky and Popeo, P.C.

(57) ABSTRACT

Provided, inter alia, are methods and compositions for treating FTO-mediated cancer.

3 Claims, 37 Drawing Sheets

(56) References Cited

OTHER PUBLICATIONS

Madak, J.T. et al. (Jun. 28, 2018, e-published May 14, 2018). "Design, Synthesis, and Biological Evaluation of 4-Quinoline Carboxylic Acids as Inhibitors of Dihydroorotate Dehydrogenase," *Journal of Medicinal Chemistry* 61(12):5162-5186.
Shi, Z-B. et al. (2013). "Design, Synthesis and Evaluation of Quinoline-based Small Molecule Inhibitor of STAT3," *Letters in Drug Design and Discovery* 10(5):420-426.
Su, R. et al. (Jul. 13, 2020, e-published Jun. 11, 2020). "Targeting FTO Suppresses Cancer Stem Cell Maintenance and Immune Evasion," *Cancer Cell* 38(1):79-96.e11.
Wunz, T.P. et al. (Aug. 1987). "New antitumor agents containing the anthracene nucleus," *Journal of Medicinal Chemistry* 30(8):1313-1321.
Dexter, D.L. et al. (Dec. 31, 1985). Activity of a Novel 4-Quinolinecarboxylic Acid, NSC 368390 [6-Fluoro-2-(2'-fluoro-1,1'-biphenyl-4-yl)-3-methyl-4-quinolinecarboxylic Acid Sodium Salt], against Experimental Tumors, *Cancer Research* 45:5563-5568.
RN: 1052223-82-1 STN Registry database, entered STN Sep. 24, 2008, 1 page.
Olsen, S.N. et al. (Jun. 18, 2020). "It's Not What You Say But How You Say It: Targeting RNA Methylation in AML," *Mol Cell* 78(6): 996-998.
Boccaletto, P. et al. (Jan. 4, 2018). "MODOMICS: a database of RNA modification pathways. 2017 update," *Nucleic Acids Res* 46(D1):D303 -D307.
Chen, B. et al. (Oct. 31, 2012, e-published Oct. 17, 2012). Development of cell-active N6-methyladenosine RNA demethylase FTO inhibitor. *J Am Chem Socv*134(43):17963-17971.
Dang, L. et al. (Dec. 10, 2009). "Cancer-associated IDH1 mutations produce 2-hydroxyglutarate," *Nature* 462(7274):739-744.
Deng, X. et al. (Jul. 30, 2018). "Critical Enzymatic Functions of FTO in Obesity and Cancer," *Front Endocrinol* (Lausanne) 9:396.
Doaei, S. et al. (May 24, 2019). "Changes in FTO and IRX3 gene expression in obese and overweight male adolescents undergoing an intensive lifestyle intervention and the role of FTO genotype in this interaction," *Journal of Translational Medicine* 17(1):176.
Dombret, H. et al. (Jul. 16, 2015, e-published May 18, 2015). "International phase 3 study of azacitidine vs conventional care regimens in older patients with newly diagnosed AML with >30% blasts," *Blood* 126(3):291-299.
Frayling, T.M. et al. (May 11, 2007, e-published Apr. 12, 2007). "A common variant in the FTO gene is associated with body mass index and predisposes to childhood and adult obesity," *Science* 316(5826):889-894.
Frye, M. et al. (Sep. 28, 2018). "RNA modifications modulate gene expression during development," *Science* 361(6409):1346-1349.
Gao, M. et al. (Dec. 11, 2017, e-published Nov. 29, 2017). "Stereoselective Stabilization of Polymeric Vitamin E Conjugate Micelles," *Biomacromolecules* 18(12):4349-4356.
He, W. et al. (Sep. 24, 2015). "Identification of A Novel Small-Molecule Binding Site of the Fat Mass and Obesity Associated Protein (FTO)," *J Med Chem* 58(18):7341-7348.
Hernandez-Caballero, M.E et al. (Mar. 2015, e-publsihed Nov. 12, 2014). "Single nucleotide polymorphisms of the FTO gene and cancer risk: an overview," *Mol Biol Rep* 42(3):699-704.
Huang, Y et al. (Jan. 2015, e-published Dec. 1, 2014). "Meclofenamic acid selectively inhibits FTO demethylation of m6A over ALKBH5," *Nucleic Acids Res* 43(1):373-384.
Huang, Y. et al. (Apr. 15, 2019). "Small-molecule targeting of oncogenic FTO demethylase in acute myeloid leukemia," *Cancer Cell* 35(4):677-691.
International Search Report mailed on Dec. 9, 2020, for PCT Application No. PCT/US2020/043294, filed Jul. 23, 2020, 6 pages.
Issa, J.P. et al. (Mar. 1, 2004, e-published Nov. 6, 2003). "Phase 1 study of low-dose prolonged exposure schedules of the hypomethylating agent 5-aza-2'-deoxycytidine (decitabine) in hematopoietic malignancies," *Blood* 103(5):1635-1640.
Jia, G. et al. (Oct. 16, 2011). "N6-methyladenosine in nuclear RNA is a major substrate of the obesity-associated FTO," *Nat Chem Biol* 7(12): 885-887.
Jia, G. et al. (Feb. 2013, e-published Dec. 4, 2012). "Reversible RNA adenosine methylation in biological regulation," *Trends Genet* 29(2):108-115.
Li, Z. et al. (Jan. 9, 2017, e-published Dec. 22, 2016). FTO Plays an Oncogenic Role in Acute Myeloid Leukemia as a N(6)-Methyladenosine RNA Demethylase. *Cancer Cell* 31(1):127-141.
Li, Z. et al. (Oct. 22, 2015, e-published Sep. 11, 2015). "Overexpression and knockout of miR-126 both promote leukemogenesis," *Blood* 126(17):2005-2015.
Liu, J. et al. (Aug. 25, 2018, e-published Jun. 2, 2018). "m(6)A demethylase FTO facilitates tumor progression in lung squamous cell carcinoma by regulating MZF1 expression," *Biochem Biophys Res Commun* 502(4):456-464.
Niu, Y. et al. (Mar. 28, 2019). "RNA N6-methyladenosine demethylase FTO promotes breast tumor progression through inhibiting BNIP3," *Mol Cancer* 18(1):46.
Padariya, M. et al. (Oct. 2016, e-published Sep. 13, 2016). "Structure-based design and evaluation of novel N-pheny1-1H-indo1-2-amine derivatives for fat mass and obesity-associated (FTO) protein inhibition," *Comput Biol Chem* 64:414-425.
PubChem CID 5351322, Create Date: Mar. 27, 2005, Modify Date: Sep. 19, 2020, 23 pages.
Shen, X-P. et al. (Dec. 2018). "Low expression of microRNA-1266 promotes colorectal cancer progression via targeting FTO," *Rev Med Pharmacol Sci* 22(23):8220-8226.
Singh, B. et al. (Jul. 8, 2016). "Important Role of FTO in the Survival of Rare Panresistant Triple-Negative Inflammatory Breast Cancer Cells Facing a Severe Metabolic Challenge," *PLoS One* 11(7):e0159072.
Su, R. et al. (Jan. 11, 2018, e-published Dec. 14, 2017). "R-2HG Exhibits Anti-tumor Activity by Targeting FTO/m 6 A/MYC/CEBPA Signaling," *Cell* 172(1-2):90-105.
Tang, X. et al. (Feb. 2019, e-published Dec. 28, 2018). "The role of the fat mass and obesity-associated protein in the proliferation of pancreatic cancer cells," *Oncol Lett* 17(2):2473-2478.
Toh, J.D.W. et al. (Jan. 1, 2015, e-published Sep. 22, 2014). "A strategy based on nucleotide specificity leads to a subfamily-selective and cell-active inhibitor of N6-methyladenosine demethylase FTO," *Chem. Sci.* 6(1):112-122.
Wang, T. et al. (Nov. 4, 2015). "Fluorescein Derivatives as Bifunctional Molecules for the Simultaneous Inhibiting and Labeling of FTO Protein," *J Am Chem Soc* 137(43): 13736-13739.
Ward, P.S. et al. (Mar. 16, 2010, e-published Feb. 18, 2010). "The common feature of leukemia-associated IDH1 and IDH2 mutations is a neomorphic enzyme activity converting alpha-ketoglutarate to 2-hydroxyglutarate," *Cancer Cell* 17(3):225-234.
Written Opinion mailed on Dec. 9, 2020, for PCT Application No. PCT/US2020/043294, filed Jul. 23, 2020, 12 pages.
Wunderlich, M. et al. (Mar. 21, 2013, e-published Jan. 24, 2013). "AML cells are differentially sensitive to chemotherapy treatment in a human xenograft model," *Blood* 121(12):e90-97.
Xu, D. et al. (Oct. 2017, e-published Aug. 14, 2017). "FTO expression is associated with the occurrence of gastric cancer and prognosis," *Oncology Reports* 38(4):2285-2292.
Yan, F. et al. (Nov. 2018, e-published Oct. 8, 2018). "A dynamic N(6)-methyladenosine methylome regulates intrinsic and acquired resistance to tyrosine kinase inhibitors," *Cell Res* 28(11):1062-1076 (2018).
Yang, H. et al. (Jun. 2014, e-published Nov. 25, 2013). "Expression of PD-L1, PD-L2, PD-1 and CTLA4 in myelodysplastic syndromes is enhanced by treatment with hypomethylating agents," *Leukemia* 28(6):1280-1288.
Zheng, G. et al. (Aug. 20, 2014, e-published Jun. 5, 2014). "Synthesis of a FTO inhibitor with anticonvulsant activity," *ACS Chemical Neuroscience* 5(8):658-665.

* cited by examiner

FIG. 5G1
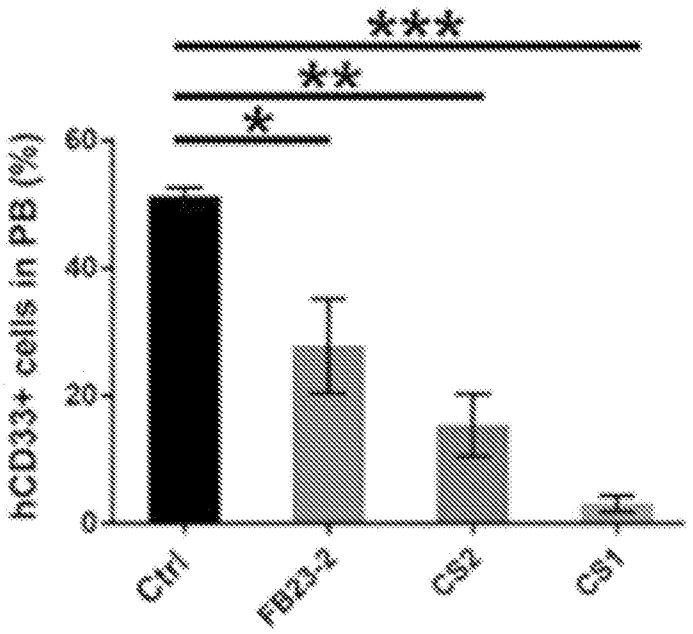
FIG. 5G2
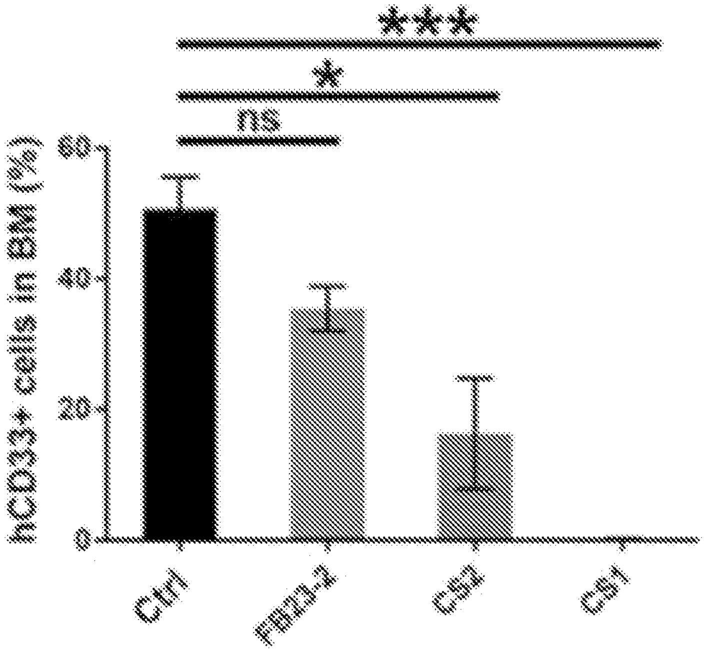

FIG. 5G3
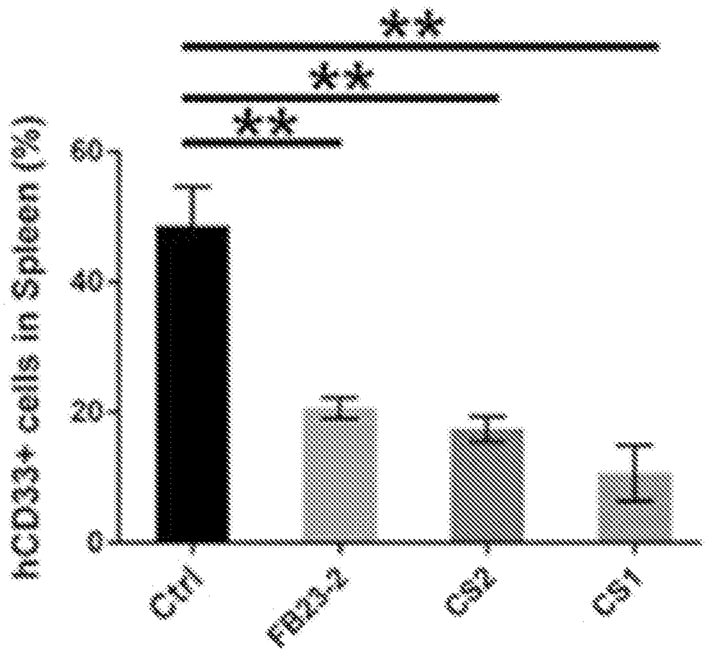
FIG. 5H
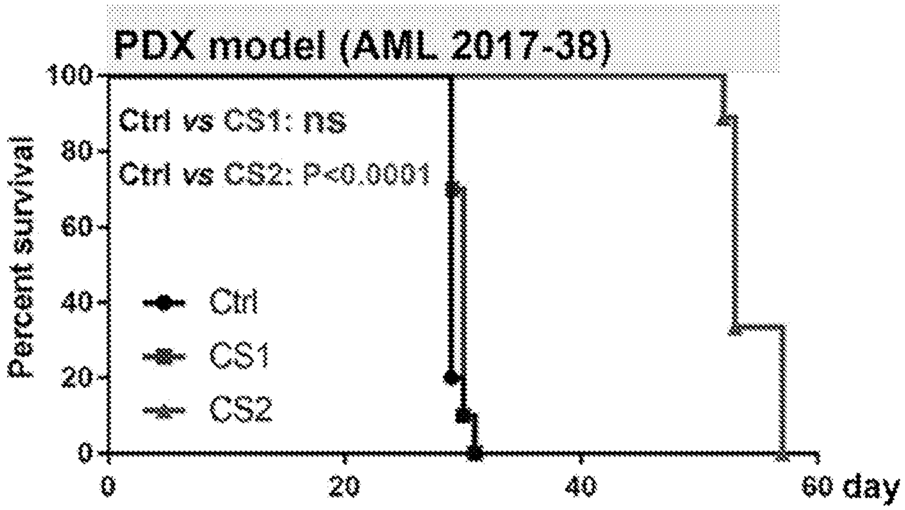

METHODS AND COMPOSITIONS FOR TREATING CANCER

This application claims the benefit of priority to U.S. Provisional Application No. 62/877,444, filed on Jul. 23, 2019, which is incorporated herein by reference in its entirety.

STATEMENT AS TO RIGHTS TO INVENTIONS MADE UNDER FEDERALLY SPONSORED RESEARCH AND DEVELOPMENT

This invention was made with government support under R01 CA243386 R01, and R01 CA214965 awarded by the National Institutes of Health. The government has certain rights in the invention.

BACKGROUND

Among the over 170 modified RNA nucleotides, N6-methyladenosine ($m^6A$) represents the most abundant and prevalent internal modification in eukaryotic mRNA (1,2). Fat mass and obesity-associated protein (FTO) was identified as the first RNA demethylase that can remove $m^6A$ from RNA through an α-Ketoglutarate (α-KG) and Fe(II)-dependent mechanism (3), suggesting that $m^6A$ is a reversible and dynamic RNA modification that may impact biological regulation analogous to other well-studied reversible epigenetic changes such as DNA and histone modifications (4). FTO is known to be robustly associated with increased body mass and obesity in humans (5). Epidemiology studies have recently demonstrated a strong association amongst FTO single nucleotide polymorphisms (SNPs), overweight/obesity and the risk of various types of cancers (e.g., breast, prostate, kidney and pancreatic cancers, as well as hematopoietic malignancies including myeloma, lymphoma and leukemia) (6, 7).

It was recently discovered that FTO is highly expressed in acute myeloid leukemia (AML) patients, especially those with t(11q23)/MLL-rearrangements, t(15;17)/PML-RARA, FLT3-ITD and/or NPM1 mutations, and plays a critical oncogenic role in leukemogenesis as an $m^6A$ demethylase (8). Subsequently, it was shown that FTO is a target of R-2-hydroxyglutarate (R-2HG; a metabolite produced at high levels by IDH1/2 mutants (9,10)) and by suppression of FTO activity, R-2HG displays intrinsic and broad anti-leukemia effects (11). In addition, the aberrant overexpression and potential oncogenic role of FTO have also been reported in multiple solid tumors (including breast, lung, pancreatic, colorectal and gastric cancer) (12-16). Moreover, data suggests that FTO is likely a master mediator of drug response, and pharmacological inhibition or genetic depletion of FTO could significantly sensitize cancer cells to other therapeutic agents (11,17). Accordingly, FTO seems to play oncogenic role in various types of cancers and is a promising drug target for cancer therapy.

A set of specific and non-specific FTO inhibitors has been recently identified (11,18-25). However, all these small molecules are limited in clinical study due to mild biological function and low sensitivity and/or specificity (26). Thus, there is a need in the art for improved cancer treatment options. Provided herein are solutions to these problems and other problems in the art.

BRIEF SUMMARY

Provided herein, inter alia, are methods and compositions for treating cancer. In an aspect, provided herein is a method of treating cancer in a subject in need thereof, the method comprising administering a therapeutically effective amount of an FTO inhibitor, wherein the subject has an elevated level of FTO when compared to a control.

In another aspect, provided herein is a compound of formula Ia or Ib (CS1-3 or CS1-7 respectively), or an enantiomer or mixture of enantiomers thereof, or a pharmaceutically acceptable salt, solvate, hydrate, co-crystal, clathrate, or polymorph thereof:

(Ia)

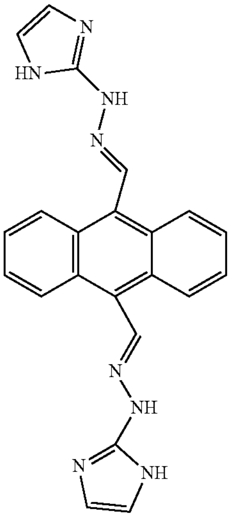

or (Ib)

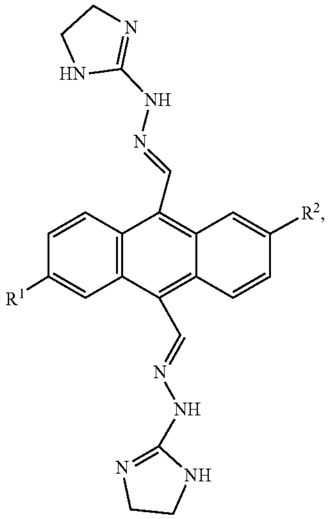

wherein $R^1$ and $R^2$ are independently hydrogen, halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and wherein at least one of $R^1$ or $R^2$ is not hydrogen.

In another aspect, provided herein is a compound of formula IIa (CS2-2) or an enantiomer or mixture of enantiomers thereof, or a pharmaceutically acceptable salt, solvate, hydrate, co-crystal, clathrate, or polymorph thereof:

(IIa)

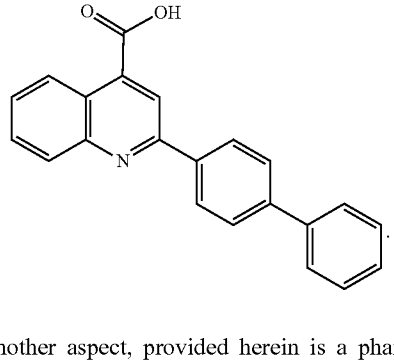

In another aspect, provided herein is a pharmaceutical composition comprising a compound of formula (Ia), (Ib) or (IIa), or an enantiomer or mixture of enantiomers thereof, or a pharmaceutically acceptable salt, solvate, hydrate, co-crystal, clathrate, or polymorph thereof, and a pharmaceutically acceptable excipient.

In another aspect, provided herein is a method of determining whether a cancer patient expresses high FTO levels, the method comprising: (i) obtaining a biological sample from the patient; and (ii) measuring the FTO levels in the biological sample; wherein if the FTO level is elevated when compared to a control, the subject is identified as responsive to the FTO inhibitor and wherein if the FTO level is elevated when compared to a control, the subject is selected for treatment with the FTO inhibitor.

BRIEF DESCRIPTION OF THE DRAWINGS

FIG. 2A compares cell viability of AML cells with high FTO expression (MONOMAC 6 (MM6), NOMO-1, MV4-11, ML-2, MA9.3ITD and U937) and low FTO expression (K562 and TF-1) following 72 hour treatment with compound of formula (I) (CS1). FIG. 2B compares cell viability of AML cells with high FTO expression (MONOMAC 6 (MM6), NOMO-1, MV4-11, ML-2, MA9.3ITD and U937) and low FTO expression (K562 and TF-1) following 72 hour treatment with compound of formula (II) (CS2). FIG. 2C compares cell viability of NOMO-1 AML cells, with and without FTO knockdown, following treatment with compound of formula (I) (CS1). FIG. 2D compares cell viability of NOMO-1 AML cells, with and without FTO knockdown, following treatment with compound of formula (II) (CS2). FIG. 2E compares cell viability of primary cells ($CD34^+$ cells) isolated from AML patients and healthy donors following 48 hour treatment with compound of formula (I) (CS1) (100 nM). FIG. 2F compares cell viability of primary cells ($CD34^+$ cells) isolated from AML patients and healthy donors following 48 hour treatment with compound of formula (II) (CS2) (200 nM).

FIG. 2G compares the effects of inhibition of previously reported FTO inhibitors (FB23-2 and MO-I-500) to FTO inhibitors of formula (I) (CS1) and (II) (CS2) on viability of MM6 cells. FIG. 2H compares the effects of inhibition of previously reported FTO inhibitors (FB23-2 and MO-I-500) to FTO inhibitors of formula (I) (CS1) and (II) (CS2) on viability of NB4 cells.

FIG. 3A shows FTO demethylase activity following treatment of cell-free system with compound of formula (I) (CS1). FIG. 3B shows FTO demethylase activity following treatment of cell-free system with compound of formula (II) (CS2). FIG. 3C shows inhibitory effects of compounds of formula (I) (CS1) and (II) (CS2) on FTO demethylase activity in cell-free system.

FIG. 4A shows dose-dependent cell apoptosis of AML cell lines following 48 hour treatment with compound of formula (I) (CS1). FIG. 4B shows dose-dependent cell apoptosis of AML cell lines following 48 hour treatment with compound of formula (II) (CS2). FIG. 4C shows cell cycle arrest in G0/G1 and S/G2/M stages of NOMO-1 cells following 48 hour treatment with DMSO (panel 1), compound of formula (I) (CS1) (panel 2) or compound of formula (II) (CS2) (panel 3) (detected by PI staining). FIG. 4D shows cell cycle arrest in G0/G1 and S/G2/M stages of NOMO-1 cells following 48 hour treatment with DMSO (panel 1), compound of formula (I) (CS1) (panel 2) or compound of formula (II) (CS2) (panel 3) (detected by Hochest 33342/pyronin Y staining). FIG. 4E compares the effects on myeloid differentiation in NB4 cells, following treatment with ATRA, compound of formula (I) (CS1), and combined treatment of ATRA and compound of formula (I) (CS1). FIG. 4F compares the effects on myeloid differentiation in NB4 cells, following treatment with ATRA, compound of formula (II) (CS2), and combined treatment of ATRA and compound of formula (II) (CS2). FIG. 4G shows relative abundance of surface CD34 and intracellular FTO in AML patient-derived LSCs ($CD34^+$ cells enriched from bone marrow mononuclear cells of AML patients) and normal HSPCs (healthy control). FIG. 4H shows statistical results showing the expression of CD34 marker and abundance of FTO in healthy control and AML patients. FIG. 4I shows the abundance of FTO protein in $CD34^-$ and $CD34^+$ hematopoietic stem/progenitor cells HSPCs (healthy controls) or LSCs (AML patients).

FIGS. 5A-I show effects of compounds of formula (I) (CS1) and (II) (CS2) on leukemia progression and survival of AML mice. FIG. 5A shows effect of treatment with compound of formula (I) (CS1) on colony forming ability of primary murine MLL-AF9 (MA9) leukemic cells in vitro. FIG. 5B shows effect of treatment with compound of formula (II) (CS2) on colony forming activity of primary murine MLL-AF9 (MA9) leukemic cells in vitro. FIG. 5C shows effect of treatment with compound of formula (I) (CS1) on colony forming ability of murine FLT3ITD/$NPM1^{mut}$ leukemic cells in vitro. FIG. 5D shows effect of treatment with compound of formula (II) (CS2) on colony forming ability of murine FLT3ITD/NPM1$^{mut}$ leukemic cells in vitro. FIG. 5E shows Kaplan-Meier survival curves of xenograft mouse model with MA9.3ITD AML cells following 48 hour treatment with previously reported FTO inhibitor FB23-2, compound of formula (I) (CS1) or compound of formula (II) (CS2) (at 100 nM). FIG. 5F shows Kaplan-Meier survival curves of xenograft mouse model with NOMO-1 AML cells following 48 hour treatment with compound of formula (I) (CS1) or (II) (CS2) (at 100 nM). FIG. 5G1 shows engraftment of human MA9.3ITD (hCD33 positive) cells into peripheral blood (PB) of NRGS mice at the end point of each mouse. FIG. 5G2 shows engraftment of human MA9.3ITD (hCD33 positive) cells into bone marrow (BM) of NRGS mice at the end point of each mouse. FIG. 5G3 shows engraftment of human MA9.3ITD (hCD33 positive) cells into spleen of NRGS mice at the end point of each mouse. FIG. 5H shows Kaplan-Meier survival curves of AML PDX mouse models following treatment with compound of formula (I) (CS1) or (II) (CS2) (administered via i.p. injection). FIG. 5I shows engraftment of AML patient cells into bone marrow of recipient NRGS mice from PDX mouse model following treatment with compound of formula (I) (CS1) or (II) (CS2) (administered via i.p. injection).

FIG. 6A shows the polymeric micelles of methoxy poly(ethyleneglycol)-b-poly(D,L-lactide) (mPEG-b-PLA) and pi-cyclodextrin used for delivery of compound of formula (I) (CS1) during the in vivo study. FIG. 6B shows Kaplan-Meier survival curves of AML PDX mouse models following treatment with compound of formula (I) (CS1), the compound is administered free (via i.p. injection) or in micelle (via i.v. injection). FIG. 6C shows Kaplan-Meier survival curves of secondary bone marrow transplantation with MA9 leukemic cells following treatment with compound of formula (I) (CS1) or (II) (CS2), the compound of formula (I) (CS1) is administered free (via i.p. injection) or in micelle (via i.v. injection). FIG. 6D shows engraftment of (CD45.2+) cells, following treatment with compound of formula (I) (CS1) in micelles or compound of formula (II) (CS2), into peripheral blood of CD45.1 recipients, secondary bone marrow transplantation with MA9 murine cells. FIG. 6E shows Kaplan-Meier survival curves of PDX model with AML cells after treatment with control, compound of formula (I) (CS1) in micelles, compound of formula (II) (CS2), or FB23-2. FIG. 6F shows Kaplan-Meier survival curves of xenograft mouse model with MA9.3ITD cells after treatment with control, compound of formula (II) (CS2), or β-cyclodextrin enclosed compound of formula (I) (CS1).

FIG. 7A shows synergistic effects, between compounds of formula (I) (CS1) or (II) (CS2) (FTO inhibitor) and 5-azacytidine (AZA, a DNMT inhibitor), on cell proliferation in NOMO-1. FIG. 7B shows synergistic effects, between compounds of formula (I) (CS1) or (II) (CS2) (FTO inhibitors) and 5-aza-2'-deoxycytidine (DAC, a DNMT inhibitor), on cell proliferation in NOMO-1. FIG. 7C shows synergistic effects, between compounds of formula (I) (CS1) or (II) (CS2) (FTO inhibitors) and 5-azacytidine (AZA, a DNMT inhibitor), on cell growth in NB4. FIG. 7D shows synergistic effects, between compounds of formula (I) (CS1) or (II) (CS2) (FTO inhibitors) and 5-aza-2'-deoxycytidine (DAC, a DNMT inhibitor), on cell growth in NB4. FIG. 7E shows synergistic effects, between compounds of formula (I) (CS1) (FTO inhibitor) and 5-aza-2'-deoxycytidine (DAC, a DNMT inhibitor), on colony forming ability (repeated 3 times). FIG. 7F shows dose dependent effect of 5-aza-2'-deoxycytidine (DAC) on expression of PD-L1 and PD-L-2 in MONOMAC 6 cells. FIG. 7G shows effect of compounds of formula (I) (CS1) and (II) (CS2) on expression of PD-L1 and PD-L-2 in NOMO-1 AML cells. FIG. 7H shows effect of 5-azacytidine (AZA) and 5-aza-2'-deoxycytidine (DAC) on AML cells (MONOMAC 6) on cell proliferation, with and without pretreatment of the cells with compounds of formula (I) (CS1) and (II) (CS2). FIG. 7I shows Kaplan-Meier survival curves of secondary bone marrow transplantation with MA9 leukemic cells following treatment with 5-aza-2'-deoxycytidine (DAC), compound of formula (I) (CS1)-micelle, compound of formula (II) (CS2), or a combined treatment of 5-aza-2'-deoxycytidine (DAC) with compound of formula (I) (CS1)-micelle or 5-aza-2'-deoxycytidine (DAC) with compound of formula (II) (CS2).

FIG. 8A shows expression of FTO in various types of cancer as adopted from cBioPortal for cancer Genomics (http://www.cbioportal.org/). FIG. 8B shows anti-tumor effects of compounds of formula (I) (CS1) and (II) (CS2) on pancreatic cancers. FIG. 8C shows anti-tumor effects of compounds of formula (I) (CS1) and (II) (CS2) on breast tumors. FIG. 8D shows anti-tumor effects of compounds of formula (I) (CS1) and (II) (CS2) on gliomas.

FIG. 9A shows structures of the 6 analogs of compound of formula (I) (CS1) and their effects on proliferation of MONOMAC 6 AML cells. FIG. 9B shows structures of the 4 analogs of compound of formula (II) (CS2) and their effects on proliferation of MONOMAC 6 AML cells. FIG. 9C shows effect of compound of formula (IIa) (CS2-2), 5-aza-2'-deoxycytidine (DAC), 5-azacytidine (AZA), and the combined effect of compound of formula (IIa) (CS2-2) with 5-azacytidine (AZA) or 5-aza-2'-deoxycytidine (DAC), on proliferation of HONO-1 AML cells. FIG. 9D shows effect of compound of formula (IIa) (CS2-2), 5-aza-2'-deoxycytidine, 5-azacytidine, and the combined effect of compound of formula (IIa) (CS2-2) with 5-azacytidine or 5-aza-2'-deoxycytidine, on proliferation of NB4 AML cells. FIG. 9E shows effects of compounds of formula (II) (CS2) and (IIa) (CS2-2) on colony forming ability in MA9 murine cells. FIG. 9F shows effects of compounds of formula (II) (CS2) and (IIa) (CS2-2) on colony forming ability in FLT3ITD/NPM1$^{mut}$ murine cells.

DETAILED DESCRIPTION

I. Definitions

Figure 1:
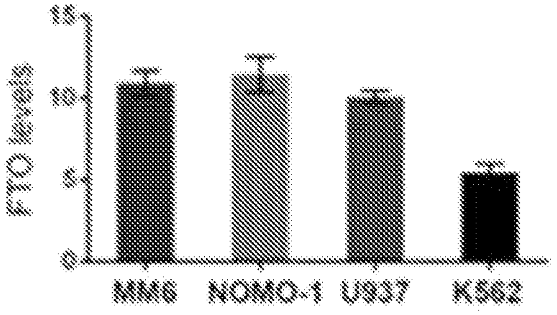
FIG. 1 shows the levels of FTO expression in various AML cells (MONOMAC 6 (MM6), NOMO-1, U937, and K562).

All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "∿" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —$S(O_2)$—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "cycloalkyl," "heterocycloalkyl," "aryl," and "heteroaryl")

includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")=NR"", —NR—C(NR'R")=NR', —S(O)R', —$S(O)_2$R', —$S(O)_2$NR'R", —NR$SO_2$R', —NR'NR"R'", —ONR'R", —NR'C(O)NR"NR'"R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R', —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")=NR"", —NR—C(NR'R")=NR'", —S(O)R', —$S(O)_2$R', —$S(O)_2$NR'R", —NR$SO_2$R', —NR'NR"R'", —ONR'R", —NR'C(O)NR"NR'"R"", —CN, —$NO_2$, —R', —$N_3$, —CH$(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$-U-, wherein T and U are independently —NR—, —O—, —CRR'—, or a single bond, and q is an integer of from 0 to 3.

Alternatively, two of the substituents on adjacent atoms of the aryl or heteroaryl ring may optionally be replaced with a substituent of the formula -A-$(CH_2)_r$-B-, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C"R"R'")_d$—, where s and d are independently integers of from 0 to 3, and X' is —O—, —NR'—, —S—, —S(O)—, —$S(O)_2$—, or —$S(O)_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

In this disclosure, "comprises," "comprising," "containing" and "having" and the like can have the meaning ascribed to them in U.S. Patent law and can mean "includes," "including," and the like. "Consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Disease control rate" refers to the patients that had a reduction in tumor size or volume; no change in tumor size or volume; and a confirmed tumor growth of <20% in the sum of the longest dimensions of their assessed target tumor lesions.

"Objective response rate" refers to the patients that had greater than 30% reduction in the sum of the longest dimensions of their assessed target tumor lesions.

"Partial response" refers to at least a 30% reduction in tumor size or volume (e.g., in the sum of the longest dimensions of their assessed target tumor lesions).

"FTO" is used according to its plain and ordinary meaning and refers to fat mass and obesity-associated protein which is a $N^6$-methyladenosine ($m^6A$) demethylase. FTO is the first RNA demethylase that can remove $m^6A$ from RNA through an α-Ketoglutarate (α-KG) and Fe(II)-dependent mechanism. There is a strong association amongst FTO single nucleotide polymorphisms (SNPs), overweight/obesity and the risk of various types of cancers, (e,g., breast, prostate, kidney and pancreatic cancers, as well as hematopoietic malignancies including myeloma, lymphoma and leukemia). In embodiment, the FTO is a human FTO or homolog thereof. In embodiment, the human FTO accession number is NG_012969.

"FTO levels" as referred to herein is the level of FTO expressed by a cancer cell or a tumor. In embodiments, the FTO level is the level of FTO expressed by a tumor or portion thereof. In embodiments, the FTO level is the level of FTO expressed by a tumor. The levels can be measured by genes, mRNA, or proteins in a biological sample.

"An elevated level of FTO" as referred to herein is an elevated level of FTO expressed by a tumor in a subject when compared to a control. FTO levels can be measured from biological samples, such as a tumor sample (e.g., resected, biopsy) or a blood sample (e.g., peripheral blood), obtained from a subject. A tumor can be a primary tumor or a metastasic tumor. A tumor as provided herein is a cellular mass including cancer cells and non-cancer cells. The non-cancer cells forming part of a tumor may be stromal cells, and immune cells (e.g., T cells, dendritic cells, B cells, macrophages). Thus, the elevated level of FTO may be expressed by a non-cancer cell (e.g., a stromal cell) or a cancer cell (e.g., a malignant T cell).

The term "inhibitor," "inhibition," "inhibit," "inhibiting" and the like in reference to a protein-inhibitor (e.g., FTO inhibitor) interaction means negatively affecting (e.g., decreasing) the activity or function of the protein (e.g., decreasing the activity of FTO protein) relative to the activity or function of the protein in the absence of the inhibitor (e.g., FTO inhibitor). In some embodiments, inhibition refers to reduction of a disease or symptoms of disease (e.g., cancer). Thus, inhibition includes, at least in part, partially or totally blocking stimulation, decreasing, preventing, or delaying activation, or inactivating, desensitizing, or down-regulating signal transduction or enzymatic activity or the amount of a protein (e.g., FTO protein). Similarly an "inhibitor" is a compound or protein that inhibits an FTO protein, e.g., by binding, partially or totally blocking, decreasing, preventing, delaying, inactivating, desensitizing, or down-regulating activity (e.g., FTO enzymatic activity).

In embodiments, an "inhibitor" is a compound or small molecule that inhibits the DNA repair pathway e.g., by binding, partially or totally blocking stimulation of the DNA repair pathway, decrease, prevent, or delay activation of the DNA repair pathway, or inactivate, desensitize, or down-regulate signal transduction, gene expression or enzymatic activity of the DNA repair pathway. In embodiments, the DNA repair pathway inhibitor inhibits DNA repair activity or expression of DNA repair proteins. In embodiments, the DNA repair pathway inhibitor is a compound or a small molecule. In embodiments, the DNA repair pathway inhibitor is an antibody. In embodiments, the DNA repair pathway inhibitor is an antisense nucleic acid.

The term "FTO inhibitor" refers to a substance capable of detectably lowering expression or enzymatic activity level of FTO compared to a control. The inhibited expression or activity of the FTO can be 10%, 20%, 30%, 40%, 50%, 60%, 70%, 80%, 90% or less than the expression or enzymatic activity in the absence of the FTO inhibitor. In certain instances, the inhibition is 1.5-fold, 2-fold, 3-fold, 4-fold, 5-fold, 10-fold, or more in comparison to the expression or enzymatic activity in the absence of the FTO inhibitorl. In embodiments, the FTO inhibitor is a compound or a small molecule. In embodiments, the FTO inhibitor is a compound of Formula (I), Formula (II), Formula (Ia), Formula (Ib), Formula (IIb), or a pharmaceutically acceptable salt of any of the foregoing.

A "PD-1 protein" or "PD-1" as referred to herein includes any of the recombinant or naturally-occurring forms of the Programmed cell death protein 1 (PD-1) also known as cluster of differentiation 279 (CD 279) or variants or homologs thereof that maintain PD-1 protein activity (e.g. within at least 50%, 80%, 90%, 95%, 96%, 97%, 98%, 99% or 100% activity compared to PD-1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto. In embodiments, the PD-1 protein is substantially identical to the protein identified by the UniProt reference number Q02242 or a variant or homolog having substantial identity thereto.

A "PD-L1" or "PD-L1 protein" as referred to herein includes any of the recombinant or naturally-occurring forms of programmed death ligand 1 (PD-L1) also known as cluster of differentiation 274 (CD 274) or variants or homologs thereof that maintain PD-L1 activity (e.g. within at least 50%, 80%, 90%, 95%, 96%, 97%, 98%, 99% or 100% activity compared to PD-L1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-L1 protein. In embodiments, the PD-L1 protein is substantially identical to the protein identified by the UniProt reference number Q9NZQ7 or a variant or homolog having substantial identity thereto.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

The term "aptamer" refers to an oligonucleotide or peptide molecule that binds to a specific target molecule.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

An "antisense nucleic acid" as referred to herein is a nucleic acid (e.g., DNA or RNA molecule) that is complementary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, *Scientific American,* 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In embodiments, the antisense nucleic acid hybridizes to the target nucleic acid in vitro. In embodiments, the antisense nucleic acid hybridizes to the target nucleic acid in a cell. In embodiments, the antisense nucleic acid hybridizes to the target nucleic acid in an organism. In embodiments, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and -anomeric sugar-phosphate, backbone modified nucleotides.

In embodiments, in the cell, the antisense nucleic acids hybridize to the corresponding RNA forming a double-stranded molecule. In embodiments, the antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is disclosed for example, in Marcus-Sakura, *Anal. Biochem.,* 172:289, (1988). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

"Biological sample" refers to any biological sample taken from a subject. Biological samples include blood, plasma, serum, tumors, tissue, cells, marrow, and the like. In embodiments, the biological sample is a blood sample. In embodiments, the biological sample is a peripheral blood sample. In embodiments, the biological sample is a tumor sample. In embodiments, the biological sample is a primary tumor sample. In embodiments, the biological sample is a metastatic tumor sample. In embodiments, the biological sample is a resected tumor sample. In embodiments, the biological sample is a tumor biopsy sample. In embodiments, the biological sample is a resected tumor sample from a primary tumor. In embodiments, the biological sample is a resected tumor sample from a metastisic tumor. In embodiments, the biological sample is a tumor biopsy sample from a primary tumor. In embodiments, the biological sample is a tumor biopsy sample from a metastisic tumor. Biological samples can be taken from a subject by methods known in the art, and can be analyzed by methods known in the art.

A "control" sample or value refers to a sample that serves as a reference, usually a known reference, for comparison to a test sample. For example, a test sample can be taken from a patient suspected of having a given disease (cancer) and compared to samples from a known cancer patient, or a known normal (non-disease) individual. A control can also represent an average value (e.g. mean or median) gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. In embodiments, a control is a negative control. In embodiments, such as some embodiments relating to detecting the level of expression or infiltration, a control comprises the average amount of expression (e.g., protein or mRNA) of infiltration (e.g., number or percentage of cells in a population of cells) in a population of subjects (e.g., with cancer) or in a healthy or general population. In embodiments, the control comprises an average amount (e.g. percentage or number of infiltrating cells or amount of expression) in a population in which the number of subjects (n) is 5 or more, 6 or more, 7 or more, 8 or more, 9 or more, 10 or more, 25 of more, 50 or more, 100 or more, 1000 or more, 5000 or more, or 10000 or more. In embodiments, the control is a standard control. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant. In embodiments, the control is a non-cancer tissue or non-cancer cell. In embodiments, the control is a subject that does not have cancer.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety. The terms "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "disease" or "condition" refer to a state of being or health status of a patient or subject capable of being treated with a compound, pharmaceutical composition, or method provided herein. In embodiments, the disease is cancer.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer (e.g., squamous cell carcinoma of the head and neck), kidney cancer (e.g., renal cell carcinoma), myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiform, glioma, melanoma, liver cancer, castration-resistant prostate cancer, metastatic castration resistant prostate cancer, breast cancer, triple negative breast cancer, glioblastoma, ovarian cancer, lung cancer, squamous cell carcinoma (e.g., head, neck, or esophagus), colorectal cancer (e.g., microsatellite instable colorectal cancer), leukemia, acute myeloid leukemia, acute lymphoblastic leukemia, chronic myelogenous leukemia, chronic lymphocytic leukemia, myeloproliferative neoplasms, myelodysplastic syndromes, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiform, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

As used herein, the terms "metastasis," "metastatic," "metastatic tumor," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, the anti-cancer agent is not a FTO inhibitor. In embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, Isocitrate Dehydrogenase (IDH) inhibitors (e.g., ivosidenib, vorasidenib, or olutasidenib); MYC inhibitors (e.g., BRD4, CDK7, CDK9, USP7, AURKA, or PLK1 inhibitors); MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), hypomethylating agents (HMAs) or DNA methyltransferase (DNMT) inhibitors (e.g., 5-azacytidine or decitabine); anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (GLEEVEC™), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+peitazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; MYC; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; FLT3 inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; anthracycline; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide;

floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. paclitaxel), Taxotere™, compounds comprising the taxane skeleton, Erbulozole (i.e. R-55104), Dolastatin 10 (i.e. DLS-10 and NSC-376128), mivobulin isethionate (i.e. as CI-980), vincristine, NSC-639829, discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (IRESSA™), erlotinib (TARCEVA™), cetuximab (ERBUTUX™), lapatinib (TYKERB™), panitumumab (VECTIBIX™), vandetanib (CAPRELSA™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

A "patient" or "subject" includes both humans and other animals, particularly mammals. Thus, the methods are applicable to both human therapy and veterinary applications. In embodiments, the patient is a mammal. In embodiments, the patient is a companion animal, such as a dog or a cat. In embodiments, the patient is human.

As used herein, and unless otherwise specified, the term "relapsed" refers to a situation where a subject or a mammal, which has had a remission of cancer after therapy has a return of cancer cells.

As used herein, and unless otherwise specified, the term "refractory or resistant" refers to a circumstance where a subject or a mammal, even after intensive treatment, has residual cancer cells in his body.

As used herein, and unless otherwise specified, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, and unless otherwise specified, the term "sensitivity" and "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least a 5%, or more, in the effectiveness of the tumor treatment.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

II. Compounds

In an aspect, provided herein is a compound of structural formula Ta or Ib (CS1-3 or CS1-7 respectively), or an enantiomer or mixture of enantiomers thereof, or a pharmaceutically acceptable salt, solvate, hydrate, co-crystal, clathrate, or polymorph thereof:

(Ia)

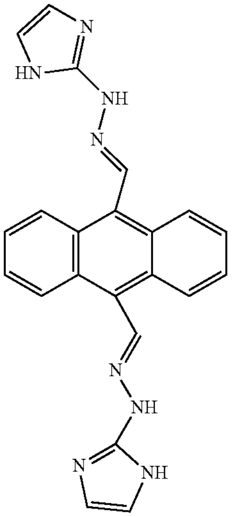

or (Ib)

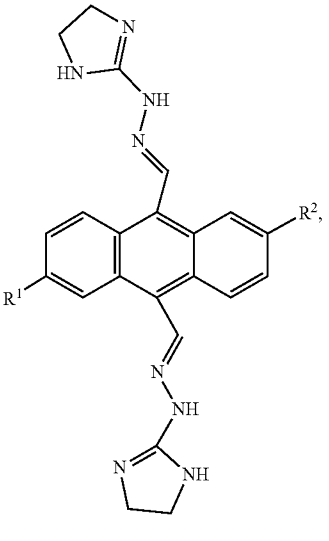

wherein $R^1$ and $R^2$ are independently hydrogen halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and wherein at least one of $R^1$ or $R^2$ is not hydrogen.

In embodiments, $R^1$ and $R^2$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ and $R^2$ are independently substituted or unsubstituted alkyl. In embodiments, $R^1$ and $R^2$ are independently unsubstituted alkyl. In embodiments, $R^1$ and $R^2$ are independently substituted alkyl.

In embodiments, $R^1$ and $R^2$ are independently unsubstituted alkyl (e.g., $C_1$-$C_8$alkyl, $C_1$-$C_6$ alkyl, or $C_1$-$C_4$ alkyl). In embodiments, $R^1$ and $R^2$ are independently methyl, ethyl, propyl, butyl, or pentyl. In embodiments, $R^1$ and $R^2$ are independently methyl.

In embodiments, $R^1$ and $R^2$ are independently substituted alkyl. In embodiments, $R^1$ and $R^2$ are independently substituted alkyl (e.g., $C_1$-$C_8$ alkyl, $C_1$-$C_6$ alkyl, or $C_1$-$C_4$ alkyl). In embodiments, $R^1$ is $R^{10}$-substituted alkyl (e.g., $C_1$-$C_8$alkyl, $C_1$-$C_6$ alkyl, or $C_1$-$C_4$ alkyl). In embodiments, $R^1$ is $R^{10}$-substituted alkyl (e.g., $C_1$-$C_4$ alkyl).

In embodiments, $R^{10}$ is halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, $CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is $R^{20}$-substituted alkyl (e.g., $C_1$-$C_8$ alkyl, $C_1$-$C_6$ alkyl, or $C_1$-$C_4$ alkyl). In embodiments, $R^2$ is $R^{20}$-substituted alkyl (e.g., $C_1$-$C_4$ alkyl).

In embodiments, $R^{20}$ is halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, provided herein is a compound of structural formula Ic, or an enantiomer or mixture of enantiomers thereof, or a pharmaceutically acceptable salt, solvate, hydrate, co-crystal, clathrate, or polymorph thereof:

(Ic)

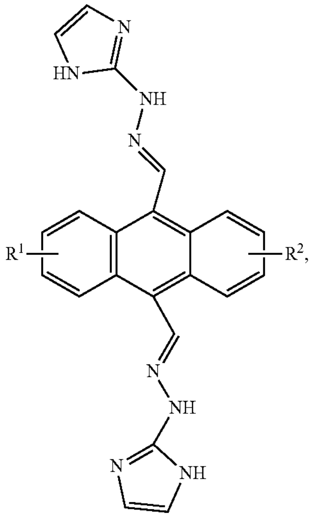

wherein $R^1$ and $R^2$ are independently hydrogen halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OC_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and wherein at least one of $R^1$ or $R^2$ is not hydrogen.

In embodiments, $R^1$ and $R^2$ are independently halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ and $R^2$ are independently substituted or unsubstituted alkyl. In embodiments, $R^1$ and $R^2$ are independently unsubstituted alkyl. In embodiments, $R^1$ and $R^2$ are independently substituted alkyl.

In embodiments, $R^1$ and $R^2$ are independently unsubstituted alkyl (e.g., $C_1$-$C_8$ alkyl, $C_1$-$C_6$ alkyl, or $C_1$-$C_4$ alkyl). In embodiments, $R^1$ and $R^2$ are independently methyl, ethyl, propyl, butyl, or pentyl. In embodiments, $R^1$ and $R^2$ are independently methyl.

In embodiments, $R^1$ and $R^2$ are independently substituted alkyl. In embodiments, $R^1$ and $R^2$ are independently substituted alkyl (e.g., $C_1$-$C_8$alkyl, $C_1$-$C_6$ alkyl, or $C_1$-$C_4$ alkyl).

In embodiments, $R^1$ is $R^{10}$-substituted alkyl (e.g., $C_1$-$C_8$ alkyl, $C_1$-$C_6$ alkyl, or $C_1$-$C_4$ alkyl). In embodiments, $R^1$ is $R^{10}$-substituted alkyl (e.g., $C_1$-$C_4$ alkyl).

In embodiments, $R^{10}$ is halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is $R^{20}$-substituted alkyl (e.g., $C_1$-$C_8$ alkyl, $C_1$-$C_6$ alkyl, or $C_1$-$C_4$ alkyl). In embodiments, $R^2$ is $R^{20}$-substituted alkyl (e.g., $C_1$-$C_4$ alkyl).

In embodiments, $R^{20}$ is halogen, $—CCl_3$, $—CBr_3$, $—CF_3$, $—CI_3$, $—CH_2Cl$, $—CH_2Br$, $—CH_2F$, $—CH_2I$, $—CHCl_2$, $—CHBr_2$, $—CHF_2$, $—CHI_2$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCBr_3$, $—OCF_3$, $—OCI_3$, $—OCH_2Cl$, $—OCH_2Br$, $—OCH_2F$, $—OCH_2I$, $—OCHCl_2$, $—OCHBr_2$, $—OCHF_2$, $—OCHI_2$, unsubstituted alkyl, unsubstituted heteroalkyl, unsubstituted cycloalkyl, unsubstituted heterocycloalkyl, unsubstituted aryl, or unsubstituted heteroaryl.

In an aspect, provided herein is a compound of structural formula IIa (CS2-2), or an enantiomer or mixture of enantiomers thereof, or a pharmaceutically acceptable salt, solvate, hydrate, co-crystal, clathrate, or polymorph thereof:

(IIa)

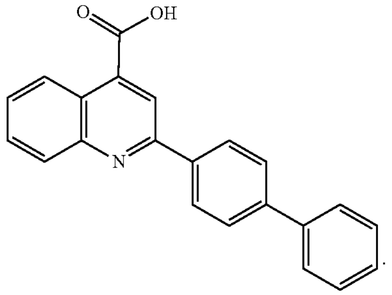

III. Pharmaceutical Compositions

In an aspect, provided herein are pharmaceutical compositions comprising a compound as described herein, or a pharmaceutically acceptable salt thereof, including embodiments (e.g., structural formulae (I), (Ia), (Ib), (Ic), (II) or (IIa)), and a pharmaceutically acceptable excipient. In an aspect, provided herein are pharmaceutical compositions comprising a compound as described herein, or a pharmaceutically acceptable salt thereof, including embodiments (e.g., structural formulae (Ia), (Ib), or (IIa)), and a pharmaceutically acceptable excipient. The provided compositions are suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

In embodiments, the pharmaceutical composition includes an effective amount of the compound, including embodiments (e.g., structural Formulae (I), (Ia), (Ib), (Ic), (II) or (IIa)), for treating cancer. In embodiments, the pharmaceutical composition includes a therapeutically effective amount of the compound, including embodiments (e.g., structural Formulae (I), (Ia), (Ib), (Ic), (II) or (IIa)), for treating cancer.

In embodiments, the pharmaceutical composition includes an effective amount of the compound, including embodiments (e.g., structural Formulae (I), (Ia), (Ib), (Ic), (II) or (IIa)), for treating cancer, wherein the cancer is modulated by FTO inhibitors. In embodiments, the pharmaceutical composition includes a therapeutically effective amount of the compound, including embodiments (e.g., structural Formulae (I), (Ia), (Ib), (Ic), (II) or (IIa)), for treating cancer wherein the cancer is modulated by FTO inhibitors.

In embodiments, the pharmaceutical composition includes an effective amount of the compound, including embodiments (e.g., structural Formulae (Ia), (Ib), or (IIa)), for treating cancer. In embodiments, the pharmaceutical composition includes a therapeutically effective amount of the compound, including embodiments (e.g., structural Formulae (Ia), (Ib), or (IIa)), for treating cancer.

In embodiments, the pharmaceutical composition includes an effective amount of the compound, including embodiments (e.g., structural Formulae (Ia), (Ib), or (IIa)), for treating cancer wherein the cancer is modulated by FTO inhibitors. In embodiments, the pharmaceutical composition includes a therapeutically effective amount of the compound, including embodiments (e.g., structural Formulae (Ia), (Ib), or (IIa)), for treating cancer wherein the cancer is modulated by FTO inhibitors.

In embodiments, the pharmaceutical composition includes an effective amount of the compound, including embodiments (e.g., structural Formulae (Ia), (Ib), or (IIa)), for treating cancer modulated by FTO inhibitors wherein the cancer is leukemia, myelodysplastic syndromes (MDS), myeloproliferative neoplasms (MPN), myeloma, lymphoma, brain tumor, breast cancer, lung cancer, pancreatic cancer, kidney cancer, prostate cancer, liver cancer, or colon cancer. In embodiments, the pharmaceutical composition includes a therapeutically effective amount of the compound, including embodiments (e.g., structural Formulae (Ia), (Ib), or (IIa)), for treating cancer modulated by FTO inhibitors wherein the cancer is leukemia, myelodysplastic syndromes (MDS), myeloproliferative neoplasms (MPN), myeloma, lymphoma, brain tumor, breast cancer, lung cancer, pancreatic cancer, kidney cancer, prostate cancer, liver cancer, or colon cancer.

In embodiments, the pharmaceutical composition includes an effective amount of the compound, including embodiments (e.g., structural Formulae (Ia), (Ib), or (IIa)), for treating leukemia wherein the leukemia is acute myeloid leukemia (AML). In embodiments, the leukemia is T-cell leukemia. In embodiments, the leukemia is chronic myelogenous leukemia (CML). In embodiments, the leukemia is chronic lymphocytic leukemia (CLL). In embodiments, the leukemia is acute lymphoblastic leukemia (ALL). In embodiments, the leukemia is chronic myelomonocytic leukemia (CMML).

In embodiments, the pharmaceutical composition includes a therapeutically effective amount of the compound, including embodiments (e.g., structural Formulae (Ia), (Ib), or (IIa)), for treating leukemia wherein the leukemia is acute myeloid leukemia (AML). In embodiments, the leukemia is T-cell leukemia. In embodiments, the leukemia is chronic myelogenous leukemia (CML). In embodiments, the leukemia is chronic lymphocytic leukemia (CLL). In embodiments, the leukemia is acute lymphoblastic leukemia (ALL). In embodiments, the leukemia is chronic myelomonocytic leukemia (CMML).

In embodiments, the pharmaceutical composition includes an effective amount of the compound, including embodiments (e.g., structural Formulae (Ia), (Ib), or (IIa)), for treating cancer modulated by FTO inhibitors, wherein the cancer is relapsed and/or refractory. In embodiments, the pharmaceutical composition includes a therapeutically effective amount of the compound, including embodiments (e.g., structural Formulae (Ia), (Ib), or (IIa)), for treating cancer modulated by FTO inhibitors, wherein the cancer is relapsed and/or refractory.

In embodiments, the pharmaceutical composition includes an effective amount of the compound, including embodiments (e.g., structural Formulae (Ia), (Ib), or (IIa)), for treating leukemia, wherein leukemia is a relapsed leukemia. In embodiments, the pharmaceutical composition includes a therapeutically effective amount of the compound, including embodiments (e.g., structural Formulae (Ia), (Ib), or (IIa)), for treating leukemia, wherein leukemia is a relapsed leukemia.

Amounts effective for this use will depend upon the severity of the disease and the general state of the patient's health. Single or multiple administrations of the compositions may be administered depending on the dosage and frequency as required and tolerated by the patient. Determination of a therapeutically effective amount of a compound described herein is well within the capabilities of those skilled in the art, especially in light of the detailed disclosure herein.

In embodiments, the pharmaceutical composition is formulated as a tablet, a powder, a capsule, a pill, a cachet, or a lozenge as described herein. The pharmaceutical composition may be formulated as a tablet, capsule, pill, cachet, or lozenge for oral administration. The pharmaceutical composition may be formulated for dissolution into a solution for administration by such techniques as, for example, intravenous administration. The pharmaceutical composition may be formulated for oral administration, suppository administration, topical administration, intravenous administration, intraperitoneal administration, intramuscular administration, intralesional administration, intrathecal administration, intranasal administration, subcutaneous administration, implantation, transdermal administration, or transmucosal administration as described herein.

The compositions for administration will commonly include a compound as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary, and will be selected primarily based on fluid volumes, viscosities, body weight and the like in accordance with the particular mode of administration selected and the subject's needs.

Solutions of the compounds (described herein) as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

In embodiments, the pharmaceutical composition may include optical isomers, diastereomers, enantiomers, isoforms, polymorphs, hydrates, solvates or products, or pharmaceutically acceptable salts of the compound described herein. The compound described herein (including pharmaceutically acceptable salts thereof) included in the pharmaceutical composition may be covalently attached to a carrier moiety, as described above. In embodiments, the compound described herein (including pharmaceutically acceptable salts thereof) included in the pharmaceutical composition is not covalently linked to a carrier moiety. A combination of covalently and not covalently linked compound described herein may be in a pharmaceutical composition herein.

In embodiments, the pharmaceutical composition includes one or more additional agent. In embodiments, the pharmaceutical composition includes one or more additional anti-cancer agent. In embodiments, the additional agent is an anti-cancer agent. In embodiments, the pharmaceutical composition includes an additional agent in a therapeutically effective amount.

In embodiments of the pharmaceutical compositions described herein, the subject is administered a therapeutically effective amount of an FTO inhibitor described herein, but is not administered or treated with any other active agents. In embodiments of the pharmaceutical compositions described herein, the subject is administered therapeutically effective amount of: (i) an FTO inhibitor described herein, and (ii) an anti-cancer agent.

In the provided pharmaceutical compositions, additional therapeutic agents can be used that are suitable to the disease (e.g., cancer) being treated. Suitable additional therapeutic agents include, but are not limited to Isocitrate Dehydrogenase Inhibitors (IDHs) (e.g., ivosidenib, vorasidenib, or olutasidenib); MYC inhibitors (e.g., BRD4, CDK7, CDK9, USP7, AURKA, or PLK1); MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), hypomethylating agents (HMAs) or DNA methyltransferase (DNMT) inhibitors (e.g., 5-azacytidine or decitabine); anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (GLEEVEC™), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; MYC; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; FLT3 inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; anthracycline; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefmgol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-ia; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. paclitaxel), Taxotere™, compounds comprising the taxane skeleton, Erbulozole (i.e. R-55104), Dolastatin 10 (i.e. DLS-10 and NSC-376128), mivobulin isethionate (i.e. as CI-980), vincristine, NSC-639829, discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, isoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}In$, $^{90}Y$, or $^{131}I$, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (IRESSA™), erlotinib (TARCEVA™), cetuximab (ERBUTUX™), lapatinib (TYKERB™), panitumumab (VECTIBIX™), vandetanib (CAPRELSA™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, and the like. The choice of agent and dosage can be determined readily by one of skill in the art based on the given disease being treated.

In embodiments, the anti-cancer agent is cytarabine, anthracycline, temozolomide, hypomethylating agent (HMA) or DNA methyltransferase (DNMT) inhibitor (e.g., 5-azacytidine or decitabine), tyrosine kinase inhibitors (TKIs), FLT3 inhibitors, Isocitrate Dehydrogenase (IDH) inhibitors (e.g., ivosidenib, vorasidenib, or olutasidenib), or MYC inhibitor (e.g., BRD4, CDK7, CDK9, USP7, AURKA, or PLK1 inhibitor).

In embodiments, the anti-cancer agent is cytarabine, anthracycline, temozolomide, hypomethylating agent (HMA), tyrosine kinase inhibitor (TKI), FLT3 inhibitor, Isocitrate Dehydrogenase (IDH) inhibitor, or MYC inhibitor.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

The combined administration contemplates co-administration, using separate formulations or a single pharmaceutical formulation, and consecutive administration in either order, wherein preferably there is a time period while both (or all) active agents simultaneously exert their biological activities.

IV. Methods of Use

In an aspect, provided herein is a method of treating cancer in a subject in need thereof, comprising administering a therapeutically effective amount of an FTO inhibitor, wherein the subject has an elevated level of FTO when compared to a control.

FTO levels may be detected at either the protein or the gene expression level. For example, FTO expression can be upregulated by certain oncogenic proteins (e.g., MLL-fusion proteins, PMLRARA, FLT3-ITD, and NPM1 mutant) and thereby FTO is aberrantly upregulated in certain subtypes of AMLs, e.g., t(11q23)/MLL-rearranged, t(15;17), FLT3-ITD, and/or NPM1-mutated AMLs. FTO expression can be quantified by multiple platforms such as quantitative real-time polymerase chain reaction (qPCR), semi-quantitative PCR, western blot, ELISA (enzyme-linked immunosorbent assay), dot blot, flow cytometry or mass spectrometry. One skilled in the art will understand the importance of selecting a threshold of FTO expression that constitutes elevated levels of FTO, such as any levels higher than the level of FTO in a particular control sample or than the medium level (e.g. average, median or mean) of FTO in a set of control samples. Controls are also valuable for determining the significance of data. For example, if values for a given parameter are widely variant in controls, variation in test samples will not be considered as significant. In some examples of the disclosed methods, when the expression level of FTO is assessed, the FTO level is compared with a control expression level of FTO.

In embodiments, the control expression level is the expression level of FTO from a sample or subject lacking cancer. In embodiments, the control expression level is the expression level of FTO from a sample or subject at a selected stage of cancer or cancer state. In embodiments, the control expression level is the expression level of FTO from a subject that has not received a therapeutic agent. In embodiments, the control expression level is the expression level of FTO from a sample of subject that has cancer. In embodiments, the control expression level is the expression level of FTO from a sample of subject that has stage 1 cancer. In embodiments, the control expression level is the expression level of FTO from a sample of subject that has stage 2 cancer. In embodiments, the control expression level is the expression level of FTO from a sample of subject that has stage 3 cancer. In embodiments, the control expression level is the expression level of FTO from a sample of subject that has stage 4 cancer.

In embodiments, the control level comprises a known amount of FTO. In embodiments, such a known amount of FTO correlates with an average level (e.g. median or mean) of subjects lacking cancer. In embodiments, such a known amount of FTO correlates with an average level of subjects at a selected stage of cancer or cancer state. In embodiments, such a known amount of FTO correlates with an average level of subjects in the absence of a particular variable such as a therapeutic agent.

In embodiments, a control level also includes the expression level of FTO from one or more selected samples or subjects as described herein. In embodiments, a control level is an expression level of FTO in a sample from a subject that does not have cancer. In embodiments, a control level is an expression level of FTO in a sample from a subject that is at a selected stage of cancer or cancer state. In embodiments, a control level is an expression level of FTO in a sample from a subject that has cancer but have not yet received treatment for the cancer. In embodiments, the control level is an expression level of FTO in samples taken from multiple subjects that do not have cancer. In embodiments, the control level is an expression level of FTO in samples taken from multiple subjects that are at a selected stage of cancer. In embodiments, the control level is an expression level of FTO in samples taken from multiple subjects that have cancer but have not yet received treatment for the cancer.

The elevated level of FTO may be determined using standard methods commonly known in the art. For example, the elevated level of FTO may be determined using quantitative real-time polymerase chain reaction (qPCR). To determine a threshold for elevated FTO, one skilled in the art could assess FTO levels in a control group of samples (e.g., samples of healthy subjects) and select the 10th percentile of FTO expression. In embodiments, the 20th percentile of FTO expression is selected as a threshold for elevated FTO. In embodiments, the 25th percentile of FTO expression is selected as a threshold for elevated FTO. In embodiments, the 30th percentile of FTO expression is selected as a threshold for elevated FTO. In embodiments, the 40th percentile of FTO expression is selected as a threshold for elevated FTO. In embodiments, the 50th percentile of FTO expression is selected as a threshold for elevated FTO. In embodiments, the 60th percentile of FTO expression is selected as a threshold for elevated FTO. In embodiments, the 70th percentile of FTO expression is selected as a threshold for elevated FTO. In embodiments, the 75th percentile of FTO expression is selected as a threshold for elevated FTO. In embodiments, the 80th percentile of FTO expression is selected as a threshold for elevated FTO. In embodiments, the 90th percentile of FTO expression is selected as a threshold for elevated FTO.

In embodiments, the method of treating cancer in a subject in need thereof, comprises administering a therapeutically effective amount of an FTO inhibitor, wherein the subject has an elevated activity level of FTO when compared to a control.

In embodiments, the FTO activity levels can be detected using $m^6A$ dot blot, mass spectrometry, or ELISA assays to assess the $m^6A$ demethylase activity. In embodiments, the FTO demethylase activity level can be detected using $m^6A$ dot blot. In embodiments, the FTO demethylase activity level can be detected using mass spectrometry. In embodiments, the FTO demethylase activity level can be detected using ELISA assays.

One skilled in the art will understand the importance of selecting a threshold of FTO activity level that constitutes elevated activity level of FTO, such as any activity higher than the activity level of FTO in a particular control sample or than the medium activity level of FTO in a set of control samples. Controls are also valuable for determining the significance of data. For example, if values for a given parameter are widely variant in controls, variation in test samples will not be considered as significant. In some examples of the disclosed methods, when the activity level of FTO is assessed, the FTO activity level is compared with a control activity level of FTO.

In embodiments, the control activity level is the activity level of FTO from a sample or subject lacking cancer. In embodiments, the control activity level is the activity level of FTO from a sample or subject at a selected stage of cancer or cancer state. In embodiments, the cancer is an IDH1- or IDH2-mutant cancer. In embodiments, the control activity level is the activity level of FTO from a subject that has not received a therapeutic agent.

In embodiments, the control level comprises a known amount of FTO. In embodiments, such a known amount of FTO correlates with an average level of subjects lacking cancer. In embodiments, such a known amount of FTO correlates with an average level of subjects at a selected stage of cancer or cancer state. In embodiments, the cancer is an IDH1- or IDH2-mutant cancer. In embodiments, such a known amount of FTO correlates with an average level of subjects in the absence of a particular variable such as a therapeutic agent.

In embodiments, a control level also includes the activity level of FTO from one or more selected samples or subjects as described herein. In embodiments, a control level is an activity level of FTO in a sample from a subject that does not have cancer. In embodiments, a control level is an activity level of FTO in a sample from a subject that is at a selected stage of cancer or cancer state. In embodiments, a control level is an activity level of FTO in a sample from a subject that has cancer but have not yet received treatment for the cancer. In embodiments, the control level is an activity level of FTO in samples taken from multiple subjects that do not have cancer. In embodiments, the control level is an activity level of FTO in samples taken from multiple subjects that are at a selected stage of cancer. In embodiments, the control level is an activity level of FTO in samples taken from multiple subjects that have cancer but have not yet received treatment for the cancer.

In embodiments, the FTO inhibitor has the structural formula I or II (CS1 or CS2 respectively), (I)

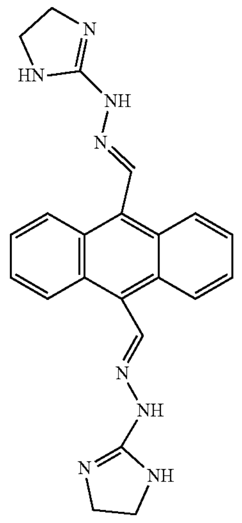

(II)

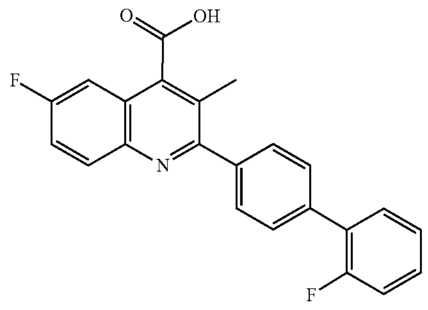

or an enantiomer or mixture of enantiomers thereof, or a pharmaceutically acceptable salt, solvate, hydrate, co-crystal, clathrate, or polymorph thereof.

In embodiments, the FTO inhibitor has the structural formula I (CS1)

(I)

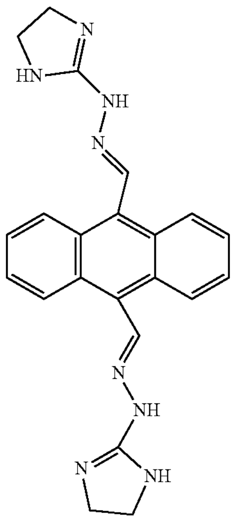

or an enantiomer or mixture of enantiomers thereof, or a pharmaceutically acceptable salt, solvate, hydrate, co-crystal, clathrate, or polymorph thereof.

In embodiments, the FTO inhibitor has the structural formula I (CS1)

(I)

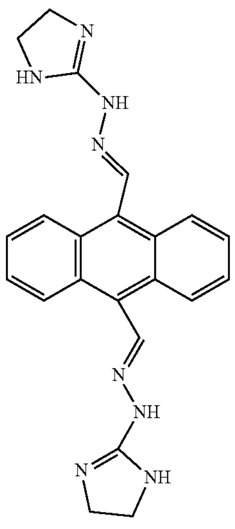

or a pharmaceutically acceptable salt thereof.

In embodiments, the FTO inhibitor has the structural formula II (CS2)

(II)

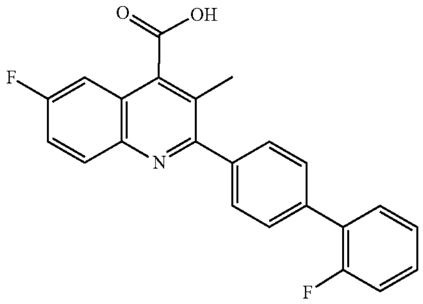

or an enantiomer or mixture of enantiomers thereof, or a pharmaceutically acceptable salt, solvate, hydrate, co-crystal, clathrate, or polymorph thereof.

In embodiments, the FTO inhibitor has the structural formula II (CS2)

(II)

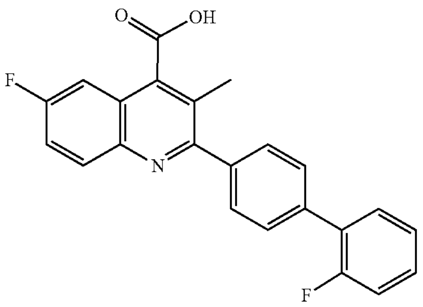

or a pharmaceutically acceptable salt thereof.

In embodiments, the method of treating cancer in a subject in need thereof, further comprises measuring an FTO level in a biological sample obtained from the subject.

In embodiments, the biological sample is a tumor sample. In embodiments, the biological sample is a resected tumor sample. In embodiments, the biological sample is a resected tumor sample from a primary tumor. In embodiments, the biological sample is a resected tumor sample from a metastisic tumor. In embodiments, the biological sample is a tumor biopsy sample. In embodiments, the biological sample is a tumor biopsy sample from a primary tumor. In embodiments, the biological sample is a tumor biopsy sample from a metastisic tumor.

In embodiments, the biological sample is a blood sample. In embodiments, the biological blood sample is a peripheral blood sample.

In embodiments, the biological sample is a normal tissue sample, such as a normal bone marrow, brain, breast, lung, pancreatic, kidney, prostate, liver, or colon tissue sample. In embodiments, the biological sample is a normal tissue sample. In embodiments, the normal tissue sample is a normal bone marrow sample. In embodiments, the normal tissue sample is a normal brain tissue sample. In embodiments, the normal tissue sample is a normal breast tissue sample. In embodiments, the normal tissue sample is a normal lung tissue sample. In embodiments, the normal tissue sample is a normal pancreatic tissue sample. In embodiments, the normal tissue sample is a normal kidney tissue sample. In embodiments, the normal tissue sample is a normal prostate tissue sample. In embodiments, the normal tissue sample is a normal liver tissue sample. In embodiments, the normal tissue sample is a normal colon tissue sample.

In embodiments, the FTO inhibitor has the formula Ia, Ib or IIa:

(Ia)

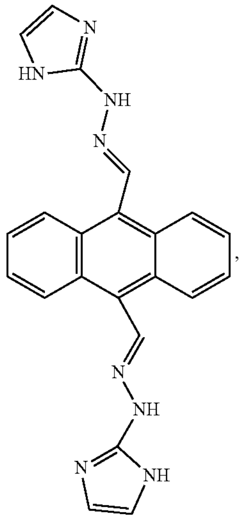

(Ib)

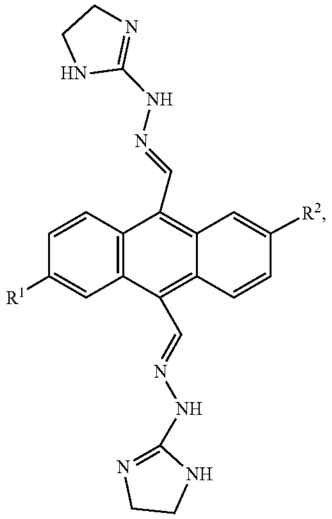

(IIa)

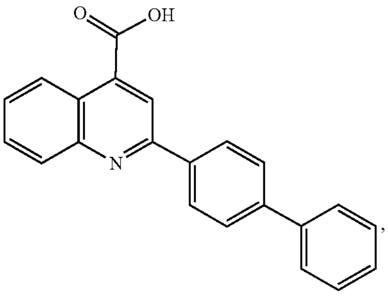

or an enantiomer or mixture of enantiomers thereof, or a pharmaceutically acceptable salt, solvate, hydrate, co-crystal, clathrate, or polymorph thereof; and wherein $R^1$ and $R^2$ are independently hydrogen halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and wherein at least one of $R^1$ or $R^2$ is not hydrogen.

In embodiments, $R^1$ and $R^2$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ and $R^2$ are independently substituted or unsubstituted alkyl. In embodiments, $R^1$ and $R^2$ are independently unsubstituted alkyl. In embodiments, $R^1$ and $R^2$ are independently substituted alkyl.

In embodiments, $R^1$ and $R^2$ are independently unsubstituted alkyl (e.g., $C_1$-$C_8$ alkyl, $C_1$-$C_6$ alkyl, or $C_1$-$C_4$ alkyl). In embodiments, $R^1$ and $R^2$ are independently methyl, ethyl, propyl, butyl, or pentyl. In embodiments, $R^1$ and $R^2$ are independently methyl.

In embodiments, $R^1$ and $R^2$ are independently substituted alkyl. In embodiments, $R^1$ and $R^2$ are independently substituted alkyl (e.g., $C_1$-$C_8$alkyl, $C_1$-$C_6$ alkyl, or $C_1$-$C_4$ alkyl).

In embodiments, $R^1$ is $R^{10}$-substituted alkyl (e.g., $C_1$-$C_8$ alkyl, $C_1$-$C_6$ alkyl, or $C_1$-$C_4$ alkyl). In embodiments, $R^1$ is $R^{10}$-substituted alkyl (e.g., $C_1$-$C_4$ alkyl).

In embodiments, $R^{10}$ is halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is $R^{20}$-substituted alkyl (e.g., $C_1$-$C_8$ alkyl, $C_1$-$C_6$ alkyl, or $C_1$-$C_4$ alkyl). In embodiments, $R^2$ is $R^{20}$-substituted alkyl (e.g., $C_1$-$C_4$ alkyl).

In embodiments, $R^{20}$ is halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, the FTO inhibitor has the formula Ic:

(Ic)

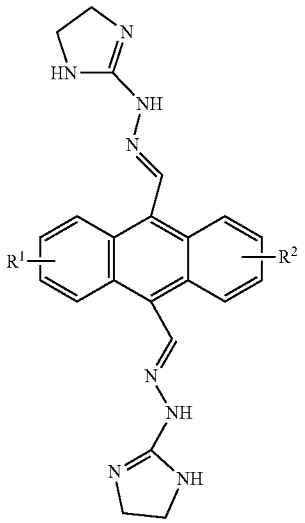

or an enantiomer or mixture of enantiomers thereof, or a pharmaceutically acceptable salt, solvate, hydrate, co-crystal, clathrate, or polymorph thereof; and wherein $R^1$ and $R^2$ are as described herein.

In embodiments, the FTO inhibitor has the formula Ic:

(Ic)

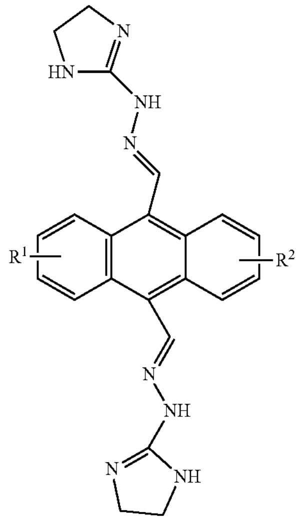

or a pharmaceutically acceptable salt, wherein $R^1$ and $R^2$ are as described herein.

In embodiments, the FTO inhibitor has the formula Ia or Tb, or an enantiomer or mixture of enantiomers thereof, or a pharmaceutically acceptable salt, solvate, hydrate, co-crystal, clathrate, or polymorph thereof:

(Ia)

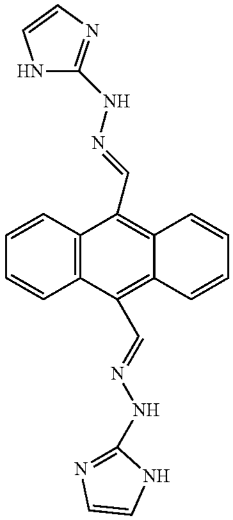

or (Ib)

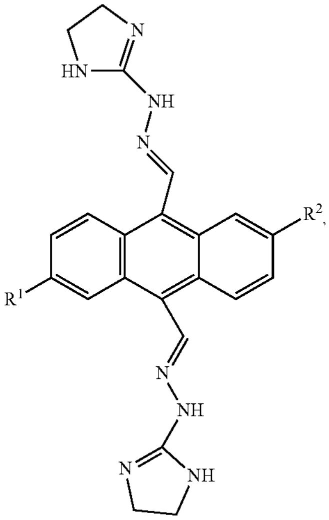

and $R^1$ and $R^2$ are as described herein.

In embodiments, the FTO inhibitor has the formula Ia, (Ia)

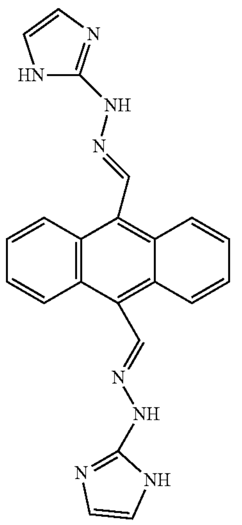

or an enantiomer or mixture of enantiomers thereof, or a pharmaceutically acceptable salt, solvate, hydrate, co-crystal, clathrate, or polymorph thereof.

In embodiments, the FTO inhibitor has the formula Ia, (Ia)

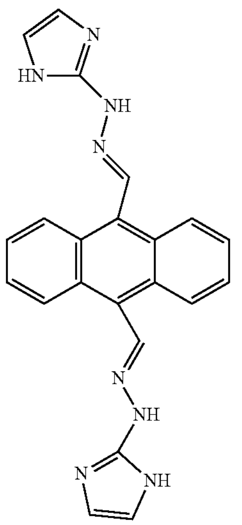

or a pharmaceutically acceptable salt thereof.

In embodiments, the FTO inhibitor has the formula Ib, (Ib)

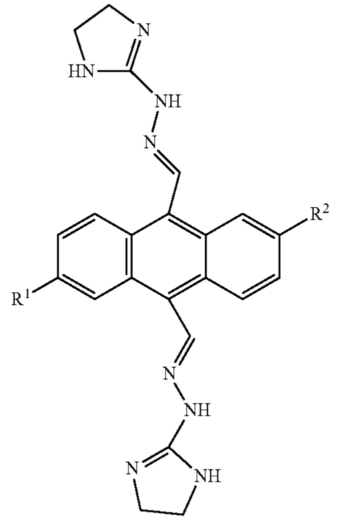

or an enantiomer or mixture of enantiomers thereof, or a pharmaceutically acceptable salt, solvate, hydrate, co-crystal, clathrate, or polymorph thereof; and wherein $R^1$ and $R^2$ are independently hydrogen halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, $NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and wherein at least one of R' or $R^2$ is not hydrogen.

In embodiments, $R^1$ and $R^2$ are independently halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments; $R^1$ and $R^2$ are independently substituted or unsubstituted alkyl. In embodiments, $R^1$ and $R^2$ are independently unsubstituted alkyl. In embodiments, R and $R^2$ are independently substituted alkyl.

In embodiments, $R^1$ and $R^2$ are independently unsubstituted alkyl (e.g., $C_1$-$C_8$ alkyl, $C_1$-$C_6$ alkyl, or $C_1$-$C_4$ alkyl). In embodiments, $R^1$ and $R^2$ are independently methyl, ethyl, propyl, butyl, or pentyl. In embodiments, $R^1$ and $R^2$ are independently methyl.

In embodiments, $R^1$ and $R^2$ are independently substituted alkyl. In embodiments, $R^1$ and $R^2$ are independently substituted alkyl (e.g., $C_1$-$C_8$ alkyl, $C_1$-$C_6$ alkyl, or $C_1$-$C_4$ alkyl).

In embodiments, $R^1$ is $R^{10}$-substituted alkyl (e.g., $C_1$-$C_8$ alkyl, $C_1$-$C_6$ alkyl, or $C_1$-$C_4$ alkyl). In embodiments, $R^1$ is $R^{10}$-substituted alkyl (e.g., $C_1$-$C_4$ alkyl).

In embodiments, $R^{10}$ is halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ is $R^{20}$-substituted alkyl (e.g., $C_1$-$C_8$ alkyl, $C_1$-$C_6$ alkyl, or $C_1$-$C_4$ alkyl). In embodiments, $R^2$ is $R^{20}$-substituted alkyl (e.g., $C_1$-$C_4$ alkyl).

In embodiments, $R^{20}$ is halogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, the FTO inhibitor has the formula Ib, (Ib)

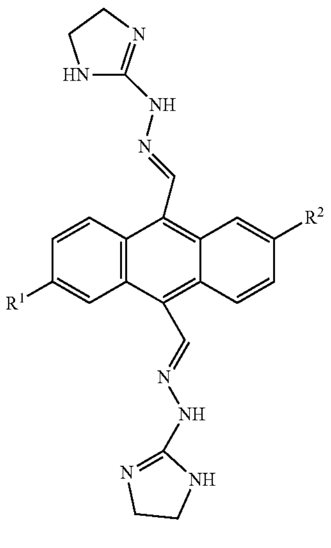

or a pharmaceutically acceptable salt thereof, wherein $R^1$ and $R^2$ are as described herein.

In embodiments, the FTO inhibitor has the formula IIa, (IIa)

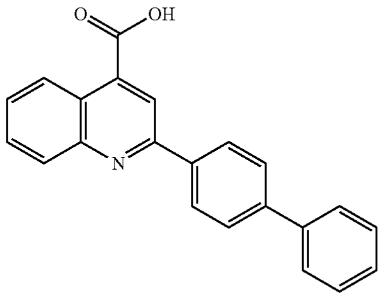

or an enantiomer or mixture of enantiomers thereof, or a pharmaceutically acceptable salt, solvate, hydrate, co-crystal, clathrate, or polymorph thereof.

In embodiments, the FTO inhibitor has the formula IIa, (IIa)

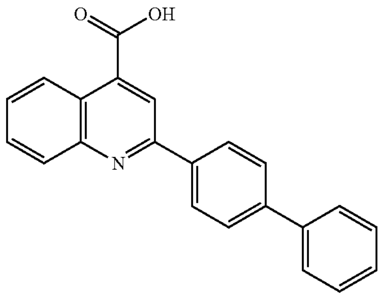

or a pharmaceutically acceptable salt thereof.

In embodiments, the FTO inhibitor is a compound or small molecule that inhibits the DNA repair pathway e.g., by binding, partially or totally blocking stimulation of the DNA repair pathway, decrease, prevent, or delay activation of the DNA repair pathway, or inactivate, desensitize, or down-regulate signal transduction, gene expression or enzymatic activity of the DNA repair pathway. In embodiments, the DNA repair pathway inhibitor inhibits DNA repair activity or expression of DNA repair proteins. In embodiments, the DNA repair pathway inhibitor is a compound or a small molecule. In embodiments, the DNA repair pathway inhibitor is an antibody. In embodiments, the DNA repair pathway inhibitor is an antisense nucleic acid.

In embodiments, the DNA repair pathway inhibitor is a peptide, small molecule, nucleic acid, antibody or aptamer. In embodiments, the DNA repair pathway inhibitor is a peptide. In embodiments, the DNA repair pathway inhibitor is a small molecule. In embodiments, the DNA repair pathway inhibitor is a nucleic acid. In embodiments, the DNA repair pathway inhibitor is an antibody. In embodiments, the DNA repair pathway inhibitor is an aptamer.

In embodiments, the FTO inhibitor is a FTO antagonist. Thus, in embodiments, the FTO inhibitor inhibits FTO activity or expression. In embodiments, the FTO inhibitor is an antibody (e.g. an anti-FTO antibody). In some embodiments, the FTO inhibitor binds to a FTO receptor (e.g. an anti-FTO receptor antibody). Thus, the FTO inhibitor may be a FTO antagonist. In some embodiments, the FTO inhibitor is a small molecule inhibitor. In other embodiments, the FTO inhibitor is a FTO antibody, for example a polyclonal or monoclonal antibody. In embodiments, the antibody is a polyclonal antibody. In embodiments, the antibody is a monoclonal antibody.

In embodiments, a FTO inhibitor may refer to a substance capable of detectably lowering expression of or activity level of the FTO signaling pathway compared to a control. The inhibited expression or activity of the FTO signaling pathway can be 10%, 20%, 30%, 40%, 50%, 60%, 70%, 80%, 90% or less than that in a control. In certain instances, the inhibition may be 1.5-fold, 2-fold, 3-fold, 4-fold, 5-fold, 10-fold, or more in comparison to a control. In embodiments, the inhibitor may inhibit the FTO signaling pathway e.g., by binding, partially or totally blocking stimulation of the FTO signaling pathway, decrease, prevent, or delay activation of the FTO signaling pathway, or inactivate, desensitize, or down-regulate signal transduction, gene expression or enzymatic activity of the FTO signaling pathway. In embodiments, the FTO signaling pathway inhibitor inhibits FTO activity or expression. In embodiments, the FTO signaling pathway inhibitor is a compound or a small molecule. In embodiments, the FTO signaling pathway inhibitor is an antibody. In embodiments, the FTO signaling pathway inhibitor is an antisense oligonucleotide.

In embodiments, the FTO inhibitor is an antibody. In embodiments, the FTO inhibitor is a nucleic acid (e.g., DNA or RNA) that is complementary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. In embodiments, the nucleic acid is a synthetic antisense nucleic acid (e.g. oligonucleotide). In embodiments, the oligonucleotide is between 15 and 25 bases in length. In embodiments, the antisense nucleic acid hybridizes to the target nucleic acid in vitro. In embodiments, the antisense nucleic acid hybridizes to the target nucleic acid in a cell. In embodiments, the antisense nucleic acid hybridizes to the target nucleic acid in an organism. In embodiments, the antisense nucleic acid hybridizes to the target nucleic acid under physiological conditions. In embodiments, antisense nucleic acids may comprise naturally occurring nucleotides or modified nucleotides such as, e.g., phosphorothioate, methylphosphonate, and -anomeric sugar-phosphate, backbone modified nucleotides.

In embodiments, antisense nucleic acid is a single stranded nucleic acid. In embodiments, antisense nucleic acid is a double stranded nucleic acid. In embodiments, antisense nucleic acid is siRNA (including its derivatives or pre-cursors, such as nucleotide analogs), short hairpin RNA (shRNA), micro RNA (miRNA), saRNA (small activating RNAs) or small nucleolar RNAs (snoRNA) or certain of their derivatives or pre-cursors. In embodiments, antisense nucleic acid is siRNA (including its derivatives or pre-cursors, such as nucleotide analogs). In embodiments, antisense nucleic acid is a short hairpin RNA (shRNA). In embodiments, antisense nucleic acid is a micro RNA (miRNA). In embodiments, antisense nucleic acid is a saRNA (small activating RNA). In embodiments, antisense nucleic acid is a small nucleolar RNA (snoRNA).

In embodiments, the FTO inhibitor is an aptamer that binds to FTO or an FTO receptor. In embodiments, the FTO inhibitor is a protein. In embodiments the FTO inhibitor is a natural ligand of the FTO or an FTO receptor. In embodiments, the FTO inhibitor is a biomolecule. In embodiments, the FTO inhibitor is a nucleic acid or derivative thereof. In embodiments, the FTO inhibitor is a flavonoid natural product. In embodiments, the FTO inhibitor is rhein.

In embodiments, the FTO inhibitors that can be employed by the methods described herein include, but are not limited to, acyl hydrazines with m3T-binding components, acyl hydrazines with 2OG-binding components, succinate hydrazide, maleate hydrazide, fumarate hydrazide, rhein, fluorescein derivatives, N-(5-chloro-2,4-dihydroxyphenyl)-1-phenylcyclobutane carboxamide (N-CDPCB), αKG analogs, {N-(3,4-dihydroxy-5-(4-chlorophenyl)-2-furanyl)ethane-sulfanamide}, meclofenamic acid and its derivatives, R-2-hydroxyglutaramate (R-2HG), derivatives of N-phenyl-1H-indol-2-amine, chemical mimics of chelators of iron, inhibitors of 2-oxoglutarate-dependent hydrolases (2OG) and ascorbic acid.

In embodiments, the inhibitor binds to the FTO or an FTO receptor with a Kd of less than 1 mM, less than 500 nM, less than 100 nM, less than 50 nm, less than 10 nM, less than 1 nM, less than 500 pM, less than 100 pM, or less than 50 pM. In a particular embodiment, the inhibitor binds to the FTO or an FTO receptor with a Kd of less than 1 mM. In a particular embodiment, the inhibitor binds to the FTO or an FTO receptor with a Kd of less than 500 nM. In a particular embodiment, the inhibitor binds to the FTO or an FTO receptor with a Kd of less than 100 nM. In a particular embodiment, the inhibitor binds to the FTO or an FTO receptor with a Kd of less than 50 nM. In a particular embodiment, the inhibitor binds to the FTO or an FTO receptor with a Kd of less than 10 nM. In a particular embodiment, the inhibitor binds to the FTO or an FTO receptor with a Kd of less than 1 nM. In a particular embodiment, the inhibitor binds to the FTO or an FTO receptor with a Kd of less than 500 pM. In a particular embodiment, the inhibitor binds to the FTO or an FTO receptor with a Kd of less than 100 pM. In a particular embodiment, the inhibitor binds to the FTO or an FTO receptor with a Kd of less than 50 pM.

In embodiments, the inhibitor of the FTO or an FTO receptor is a specific inhibitor. In embodiments, the inhibitor of the FTO or an FTO receptor is a non specific inhibitor.

In embodiments, provided herein is a method of treating cancer. In embodiments, provided herein are methods of treating leukemia, myelodysplastic syndromes (MDS), myeloproliferative neoplasms (MPN), myeloma, lymphoma, brain tumor, breast cancer, lung cancer, pancreatic cancer, kidney cancer, prostate cancer, liver cancer, or colon cancer.

In embodiments, the leukemia is acute myeloid leukemia (AML). In embodiments, the leukemia is T-cell leukemia. In embodiments, the leukemia is chronic myelogenous leukemia (CML). In embodiments, the leukemia is chronic lymphocytic leukemia (CLL). In embodiments, the leukemia is acute lymphoblastic leukemia (ALL). In embodiments, the leukemia is chronic myelomonocytic leukemia (CMML).

In embodiments, the lymphoma is selected from the group consisting of Hodgkin's lymphoma, non-Hodgkin's lymphoma, AIDS-related lymphomas, anaplastic large-cell lymphoma, angioimmunoblastic lymphoma, blastic NK-cell lymphoma, Burkitt's lymphoma, Burkitt-like lymphoma, small non-cleaved cell lymphoma, small lymphocytic lymphoma, cutaneous T-cell lymphoma, diffuse large B-cell Lymphoma, enteropathy-type T-cell lymphoma, lymphoblastic lymphoma, mantle cell lymphoma, marginal zone lymphoma, nasal T-cell lymphoma, pediatric lymphoma, peripheral T-cell lymphomas, primary central nervous system lymphoma, transformed lymphomas, treatment-related T-cell lymphomas and Waldenstrom's macroglobulinemia.

In embodiments, the cancer is myeloma. In embodiments, the cancer is lymphoma. In embodiments, the cancer is brain tumor. In embodiments, the cancer is breast cancer. In embodiments, the cancer is lung cancer. In embodiments, the cancer is pancreatic cancer. In embodiments, the cancer is kidney cancer. In embodiments, the cancer is prostate cancer. In embodiments, the cancer is liver cancer. In embodiments, the cancer is colon cancer. In embodiments, the cancer is myelodysplastic syndromes (MDS). In embodiments, the cancer is myeloproliferative neoplasms (MPN).

In embodiments, the myelodysplastic syndrome (MDS) is refractory anemia. In embodiments, the myelodysplastic syndrome (MDS) is refractory anemia with ring sideroblasts (RARS). In embodiments, the myelodysplastic syndrome (MDS) is refractory anemia with excess blasts (RAEB). In embodiments, the myelodysplastic syndrome (MDS) is chronic myelomonocytic leukemia (CMML).

In embodiments, the myeloproliferative neoplass (MPN) is chronic myeloid leukemia (CML). In embodiments, the myeloproliferative neoplasm (MPN) is essential thrombocythemia. In embodiments, the myeloproliferative neoplasm (MPN) is polycythemia vera. In embodiments, the myeloproliferative neoplasm (MPN) is primary myelofibrosis.

In embodiments, the cancer is relapsed and/or refractory. In embodiments, the cancer is relapsed. In embodiments, the cancer is refractory. In embodiments, the cancer is relapsed and refractory.

In embodiments, the cancer is leukemia. In embodiments, leukemia is a relapsed leukemia.

In embodiments of the methods described herein, the subject is administered a therapeutically effective amount of: (i) an FTO inhibitor described herein, and (ii) an anti-cancer agent.

In the provided methods of treatment, additional therapeutic agents can be used that are suitable to the disease (e.g., cancer) being treated. Suitable additional therapeutic agents include, but are not limited to Isocitrate Dehydrogenase Inhibitors (IDHs) (e.g., ivosidenib, vorasidenib, or olutasidenib); MYC inhibitors (e.g., BRD4, CDK7, CDK9, USP7, AURKA, or PLK1); MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), hypomethylating agents (HMAs) or DNA methyltransferase (DNMT) inhibitors (e.g., 5-azacytidine or decitabine); anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (GLEEVEC™), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; MYC; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; FLT3 inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; anthracycline; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. paclitaxel), Taxotere™, compounds comprising the taxane skeleton, Erbulozole (i.e. R-55104), Dolastatin 10 (i.e. DLS-10 and NSC-376128), mivobulin isethionate (i.e. as CI-980), vincristine, NSC-639829, discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (IRESSA™), erlotinib (TARCEVA™), cetuximab (ERBUTUX™), lapatinib (TYKERB™), panitumumab (VECTIBIX™), vandetanib (CAPRELSA™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, and the like. The choice of agent and dosage can be determined readily by one of skill in the art based on the given disease being treated.

In embodiments, the anti-cancer agent is cytarabine, anthracycline, temozolomide, hypomethylating agent (HMA) or DNA methyltransferase (DNMT) inhibitor (e.g., 5-azacytidine or decitabine), tyrosine kinase inhibitors (TKIs), FLT3 inhibitors, Isocitrate Dehydrogenase (IDH) inhibitors (e.g., ivosidenib, vorasidenib, or olutasidenib), or MYC inhibitor (e.g., BRD4, CDK7, CDK9, USP7, AURKA, or PLK1 inhibitor).

In embodiments, the anti-cancer agent is cytarabine, anthracycline, temozolomide, hypomethylating agent (HMA), tyrosine kinase inhibitor (TKI), FLT3 inhibitor, Isocitrate Dehydrogenase (IDH) inhibitor, or MYC inhibitor.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

The combined administration contemplates co-administration, using separate formulations or a single pharmaceutical formulation, and consecutive administration in either order, wherein preferably there is a time period while both (or all) active agents simultaneously exert their biological activities.

In another aspect, provided herein is a method to identify a subject responsive to a FTO inhibitor, to select a subject for treatment with a FTO inhibitor, or a combination thereof, the method comprising: (i) obtaining a biological sample from the patient; and (ii) measuring the FTO levels in the biological sample; wherein if the FTO level is elevated when compared to a control, the subject is identified as responsive to the FTO inhibitor and wherein if the FTO level is elevated when compared to a control, the subject is selected for treatment with the FTO inhibitor.

In an aspect, provided herein are methods to identify subjects who will be responsive to a FTO inhibitor, where the method comprises: (i) obtaining a biological sample from the patient; and (ii) measuring FTO level in the biological sample; wherein if the FTO level is elevated when compared to a control, the subject is identified as responsive to the FTO inhibitor. In embodiments, the biological sample is a tumor sample. In embodiments, the biological sample is a resected tumor sample. In embodiments, the biological sample is a resected tumor sample from a primary tumor. In embodiments, the biological sample is a resected tumor sample from a metastisic tumor. In embodiments, the biological sample is a tumor biopsy sample. In embodiments, the biological sample is a tumor biopsy sample from a primary tumor. In embodiments, the biological sample is a tumor biopsy sample from a metastisic tumor. In embodiments, the biological sample is a blood sample. In embodiments, the biological sample is a peripheral blood sample. In embodiments, the biological sample is a normal tissue sample. In embodiments, the biological sample is a normal bone marrow tissue sample. In embodiments, the biological sample is a normal brain tissue sample. In embodiments, the biological sample is a normal breast tissue sample. In embodiments, the biological sample is a normal lung tissue sample. In embodiments, the biological sample is a normal pancreatic tissue sample. In embodiments, the biological sample is a normal kidney tissue sample. In embodiments, the biological sample is a normal prostate tissue sample. In embodiments, the biological sample is a normal liver tissue sample. In embodiments, the biological sample is a normal colon tissue sample.

In embodiments, provided herein are methods to identify subjects who will be responsive to a FTO inhibitor, where the method comprises: (i) obtaining a biological sample from the patient; and (ii) measuring FTO level in the biological sample; wherein if the FTO level is elevated when compared to a control, the subject is identified as responsive to the FTO inhibitor. In embodiments, the method further comprises the administration of a therapeutically effective amount of one or more additional anti-cancer agents. In embodiments, the anti-cancer agent is cytarabine. In embodiments, the anti-cancer agent is anthracycline. In embodiments, the anti-cancer agent is temozolomide. In embodiments, the anti-cancer agent is tyrosine kinase inhibitor (TKI). In embodiments, the anti-cancer agent is FLT3 inhibitor. In embodiments, the anti-cancer agent is Isocitrate Dehydrogenase (IDH) inhibitor. In embodiments, the anti-cancer agent is MYC inhibitor. In embodiments, the anti-cancer agent is hypomethylating agent (HMA). In embodiments, the hypomethylating agent is 5-azacytidine. In embodiments, the hypomethylating agent is decitabine.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

Embodiment 1. A method of treating cancer in a subject in need thereof, the method comprising administering a therapeutically effective amount of an FTO inhibitor, wherein the subject has an elevated level of FTO when compared to a control.

Embodiment 2. The method of embodiment 1, wherein the FTO inhibitor has the structural formula I or II, (I)

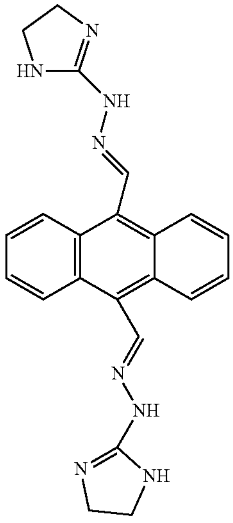

(II)

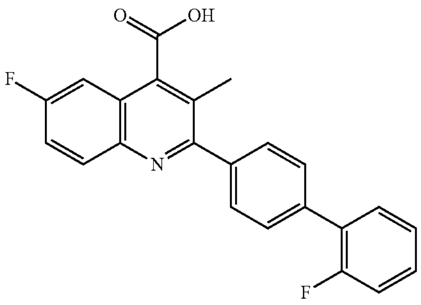

or an enantiomer or mixture of enantiomers thereof, or a pharmaceutically acceptable salt, solvate, hydrate, co-crystal, clathrate, or polymorph thereof.

Embodiment 3. The method of embodiment 1 or 2, further comprising measuring an FTO level in a biological sample obtained from the subject.

Embodiment 4. The method of any one of embodiments 1 to 3, wherein the biological sample is a tumor sample.

Embodiment 5. The method of any one of embodiments 1 to 4, wherein the tumor sample is a resected tumor sample or a tumor biopsy sample.

Embodiment 6. The method of any one of embodiments 1 to 5, wherein the tumor sample is from a primary tumor or a metastatic tumor.

Embodiment 7. The method of any one of embodiments 1 to 3, wherein the biological sample is a normal tissue sample, wherein the normal tissue sample is a bone marrow, brain, breast, lung, pancreatic, kidney, prostate, liver, or colon tissue sample.

Embodiment 8. The method of any one of embodiments 1 to 3, wherein the biological sample is a blood sample.

Embodiment 9. The method of any one of embodiments 1 to 3 and 8, wherein the blood sample is a peripheral blood sample.

Embodiment 10. The method of embodiment 1 or 2, wherein the FTO inhibitor has the formula Ia, Ib or IIa:

(Ia)

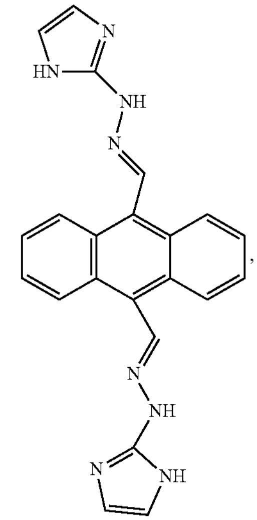

, (Ib)

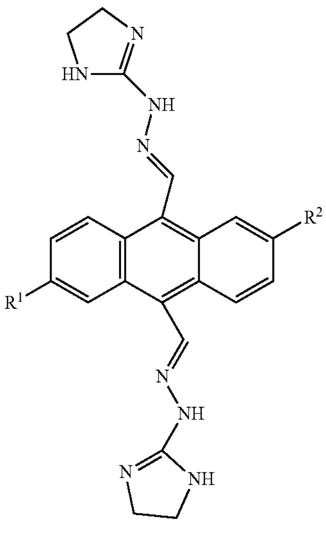

or (IIa)

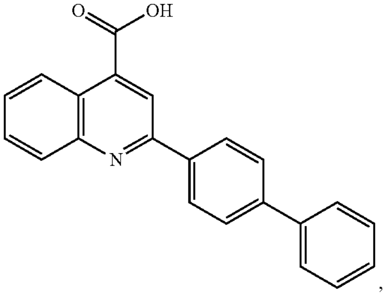

, or an enantiomer or mixture of enantiomers thereof, or a pharmaceutically acceptable salt, solvate, hydrate, co-crystal, clathrate, or polymorph thereof; and wherein $R^1$ and $R^2$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein at least one of $R^1$ or $R^2$ is not hydrogen.

Embodiment 11. A compound of formula Ia or Ib, or an enantiomer or mixture of enantiomers thereof, or a pharmaceutically acceptable salt, solvate, hydrate, co-crystal, clathrate, or polymorph thereof:

(Ia)

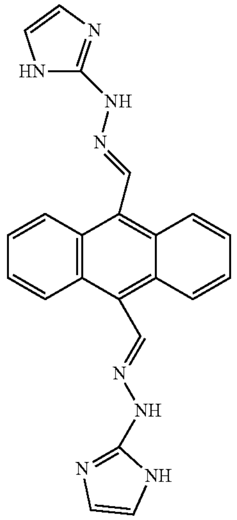

or (Ib)

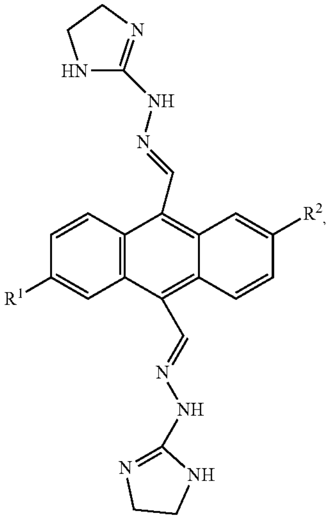

, wherein $R^1$ and $R^2$ are independently hydrogen, halogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein at least one of $R^1$ or $R^2$ is not hydrogen.

Embodiment 12. The compound of embodiment 11, wherein $R^1$ and $R^2$ are independently substituted or unsubstituted alkyl.

Embodiment 13. The compound of embodiment 11 or 12, wherein $R^1$ and $R^2$ are independently unsubstituted alkyl.

Embodiment 14. The compound of any one of embodiments 11 to 13, wherein $R^1$ and $R^2$ are independently methyl, ethyl, propyl, butyl, or pentyl.

Embodiment 15. The compound of any one of embodiments 11 to 14, wherein $R^1$ and $R^2$ are methyl.

Embodiment 16. A compound of formula IIa or an enantiomer or mixture of enantiomers thereof, or a pharmaceutically acceptable salt, solvate, hydrate, co-crystal, clathrate, or polymorph thereof:

(IIa)

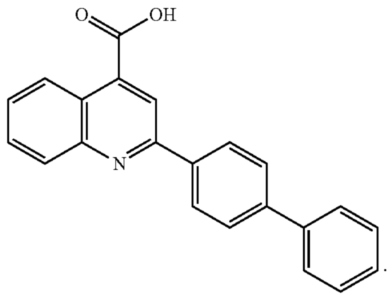

Embodiment 17. The method of any one of embodiments 1 to 10, wherein the cancer is leukemia, myelodysplastic syndromes (MDS), myeloproliferative neoplasms (MPN), myeloma, lymphoma, brain tumor, breast cancer, lung cancer, pancreatic cancer, kidney cancer, prostate cancer, liver cancer, glioblastoma (GBM), lung squamous cell carcinoma (LUSC), or colon cancer.

Embodiment 18. The method of any one of embodiments 1 to 10 and 17, wherein the cancer is relapsed and/or refractory.

Embodiment 19. The method of any one of embodiments 1 to 10, 17, and 18 wherein leukemia is acute myeloid leukemia (AML), acute lymphoblastic leukemia (ALL), chronic myelogenous leukemia (CML), or chronic lymphocytic leukemia (CLL).

Embodiment 20. The method of any one of embodiments 1 to 10 and 17 to 19, wherein leukemia is a relapsed leukemia.

Embodiment 21. A pharmaceutical composition comprising the compound of embodiment 11 or 16, and a pharmaceutically acceptable excipient.

Embodiment 22. The pharmaceutical composition of embodiment 21 for treating cancer, wherein the cancer is a cancer modulated by an FTO inhibitor.

Embodiment 23. The pharmaceutical composition of embodiment 21 or 22, wherein the cancer modulated by the FTO inhibitor is leukemia, myelodysplastic syndromes (MDS), myeloproliferative neoplasms (MPN), myeloma, lymphoma, brain tumor, breast cancer, lung cancer, pancreatic cancer, kidney cancer, prostate cancer, liver cancer, glioblastoma (GBM), lung squamous cell carcinoma (LUSC), or colon cancer.

Embodiment 24. The pharmaceutical composition of any one of embodiments 21 to 23, wherein the cancer is relapsed and/or refractory.

Embodiment 25. The pharmaceutical composition of any one of embodiments 21 to 24, wherein leukemia is acute myeloid leukemia (AML), acute lymphoblastic leukemia (ALL), chronic myelogenous leukemia (CML), or chronic lymphocytic leukemia (CLL).

Embodiment 26. The pharmaceutical composition of any one of embodiments 21 to 25 wherein leukemia is a relapsed leukemia.

Embodiment 27. The pharmaceutical composition of any one of embodiments 21 to 26 further comprising one or more additional anti-cancer agents.

Embodiment 28. A method of measuring FTO levels in a subject, the method comprising: (i) obtaining a biological sample from the subject; and (ii) measuring FTO levels in the biological sample; wherein if the FTO level is elevated when compared to a control, the subject is identified as responsive to the FTO inhibitor and wherein if the FTO level is elevated when compared to a control, the subject is selected for treatment with the FTO inhibitor.

Embodiment 29. The method of embodiment 28, wherein the subject has cancer.

Embodiment 30. The method of embodiment 28 or 29, wherein the biological sample is a tumor sample.

Embodiment 31. The method of any one of embodiments 28 to 30, wherein the tumor sample is a resected tumor sample or a tumor biopsy sample.

Embodiment 32. The method of any one of embodiments 28 to 31, wherein the tumor sample is from a primary tumor or a metastatic tumor.

Embodiment 33. The method of embodiment 28, wherein the biological sample is a normal tissue sample, wherein the normal tissue is a bone marrow, brain, breast, lung, pancreatic, kidney, prostate, liver, or colon tissue sample.

Embodiment 34. The method of embodiment 28, wherein the biological sample is a blood sample.

Embodiment 35. The method of embodiment 28 or 34, wherein the blood sample is a peripheral blood sample.

Embodiment 36. The method of any one of embodiments 1 to 10, 17 to 20, and 28 to 35, further comprising administering of a therapeutically effective amount of one or more additional anti-cancer agents.

Embodiment 37. The method of any one of embodiments 1 to 10, 17 to 20, and 28 to 36, wherein the additional anti-cancer agent is selected from the group consisting of cytarabine, anthracycline, temozolomide, a hypomethylating agent (HMA), a tyrosine kinase inhibitor (TKI), an FLT3 inhibitor, an isocitrate dehydrogenase inhibitors (IDH), and a MYC inhibitor.

Embodiment 38. The method of any one of embodiments 1 to 10, 17 to 20, and 28 to 37, wherein the hypomethylating agent (HMA) is 5-azacytidine or decitabine.

Embodiment 39. A method of measuring FTO levels in a subject wherein the subject has cancer, the method comprising: (i) obtaining a biological sample from the subject; and (ii) measuring FTO levels in the biological sample.

Embodiment 40. The method of embodiment 39, wherein the biological sample is a tumor sample.

Embodiment 41. The method of embodiment 39 or 40, wherein the tumor sample is a resected tumor sample or a tumor biopsy sample.

Embodiment 42. The method of any one of embodiments 39-41, wherein the tumor sample is from a primary tumor or a metastatic tumor.

Embodiment 43. The method of embodiment 39, wherein the biological sample is a blood sample.

Embodiment 44. The method of embodiment 43, wherein the blood sample is a peripheral blood sample.

Embodiment 45. A method of treating cancer in a subject in need thereof, the method comprising: (i) obtaining a biological sample from the subject; and (ii) measuring FTO levels in the biological sample; and (iii) administering a therapeutically effective amount of an FTO inhibitor.

Embodiment 46. The method of embodiment 45, wherein the cancer is leukemia, myelodysplastic syndromes (MDS), myeloproliferative neoplasms (MPN), myeloma, lymphoma, brain tumor, breast cancer, lung cancer, pancreatic cancer, kidney cancer, prostate cancer, liver cancer, glioblastoma (GBM), lung squamous cell carcinoma (LUSC), or colon cancer.

Embodiment 47. The method of embodiment 45 or 46, wherein the cancer is relapsed and/or refractory.

Embodiment 48. The method of any one of embodiments 45-47, wherein leukemia is acute myeloid leukemia (AML), acute lymphoblastic leukemia (ALL), chronic myelogenous leukemia (CML), or chronic lymphocytic leukemia (CLL).

Embodiment 49. The method of any one of embodiments 45-48, wherein leukemia is a relapsed leukemia.

Embodiment 50. The method of any one of embodiments 45-49, wherein the biological sample is a tumor sample.

Embodiment 51. The method of any one of embodiments 45-50, wherein the tumor sample is a resected tumor sample or a tumor biopsy sample.

Embodiment 52. The method of any one of embodiments 45-51, wherein the tumor sample is from a primary tumor or a metastatic tumor.

Embodiment 53. The method of embodiment 45, wherein the biological sample is a blood sample.

Embodiment 54. The method of embodiment 45 or 53, wherein the blood sample is a peripheral blood sample.

Embodiment 55. A method of preparing a sample from a subject having cancer, the method comprising:

(i) extracting a protein fraction or an RNA fraction from a sample from said subject; and (ii) detecting a level of FTO protein in said protein fraction or a level of FTO encoding RNA in said RNA fraction.

Embodiment 56. The method of embodiment 55 comprising extracting the protein fraction from the sample with a combination of RIPA buffer, Halt phosphatase inhibitor cocktail and Halt protease inhibitor cocktail, further comprising obtaining a protein extract, wherein said protein extract undergoes the Western Blot assay.

Embodiment 57. The method of embodiment 55 or 56 comprising the use of an FTO antibody, a GAPDH antibody, a PD-L1 antibody or a PD-L2 antibody in the Western Blot assay.

Embodiment 58. The method of any one of embodiments 55-57, comprising extracting the RNA fraction from the sample with a miRNeasy Mini Kit, further comprising a reverse transcription to obtain a cDNA.

Embodiment 59. The method of any one of embodiments 55-58 comprising the use of QuantiTect Rev. Transcription Kit to obtain the cDNA.

Embodiment 60. The method of any one of embodiments 55-59 comprising detecting the level of FTO protein in said protein fraction or a level of FTO encoding RNA in said RNA fraction further comprising the steps of:

a) labeling human primary cells with CD34 surface marker;

b) washing the cells with chilled phosphate-buffered saline;

c) re-suspending the cells in 4% paraformaldehyde at a density of $2\times10^6$ cells/ml;

d) incubating the cells at 4° C. for 20 min with rotation;

e) re-suspending the cells in 5× Permeabilization buffer;

f) staining the cells with anti-FTO (1:100) for one hour;

g) washing the cells twice with 1× Permeabilization buffer;

h) incubating the cells with an anti-rabbit IgG in 5× Permeabilization buffer for 30 min at room temperature; and i) storing the celles in FACS buffer for FTO analysis.

Embodiment 61. The method of embodiment 55, wherein the tumor sample is a resected tumor sample or a tumor biopsy sample.

Embodiment 62. The method of embodiment 55 or 61, wherein the tumor sample is from a primary tumor or a metastatic tumor.

Embodiment 63. The method of embodiment 55, wherein the biological sample is a blood sample.

Embodiment 64. The method of embodiment 55 or 63, wherein the blood sample is a peripheral blood sample.

EXAMPLES

Example 1: Structure-Based Virtual Screening Pipeline to Identify Specific Type IT Inhibitors of FTO Protein FTO is an alpha-ketoglutarate (α-KG) dependent dioxygenase with an iron atom and an α-KG molecule as catalytic center. There are two types of inhibitor to block the dioxygenaseactivity. For Type I inhibitor, it is α-KG-competitive, i.e., it replaces α-KGmolecule in the catalytic center to disable the hydroxylation reaction (27). It is the analog of α-KGmolecule, such as R-2HG, which may have no specification on α-KG-dependent dioxygenase proteins and α-KG-dependent demethylation proteins (e.g. Jumonji domain-containing protein family) (11). Type II inhibitor blocks the entrance of catalytic center and does not compete with the α-KG molecule (direct targeting of FTO protein). Type II inhibitor was designed herein.

The FTO protein three-dimensional structure was downloaded from RCBS Protein Data Bank (PDB id 4zs2) (22) by keeping the α-KG molecule and catalytic metal atom as the structure for docking. The in-house developed LvsPipe (Ligand Virtual Screening Pipeline) is employed to screen the NCI DTP compound library in silico to discover Type II FTO inhibitor. LvsPipe is a multiple-stage and full-coverage pipeline for virtual ligand screening. It utilizes the three precisions (HTVS, SP and XP) of Schrödinger Glide software (28) for docking in series, and docks every small molecule to cover the full compound library for screening. It can find lead compounds with $IC_{50}$ in micromolar range at a hit rate of more than 10% from none-specific compound library (29).

First, HTVS precision mode of Glide was implemented to dock the whole NCI DTP library with about 260,000 compounds. The 10,000 top-ranked compounds were docked and scored using the Glide standard precision (SP) mode. Then the 1,000 top-ranked compounds from SP precision docking were re-docked and re-scored by using the extra precision XP mode. The above multiple-stage docking pipeline was optimized to run efficiently on multiple CPU cores. The 1,000 compounds were further analyzed and filtered by Lipinski's rule of five (30), HTS frequent hitter (PAINS) (31), protein reactive chemicals such as oxidizer or alkylator (ALARM) (32), and maximized the molecule diversity by using UDScore (Universe Diversity Score, developed by us to measure library diversity which is independent of library size).

Among all the predicted hits, the biological function of the top 213 candidates with top-ranked XP docking scores, together with structure diversity analysis and docking pose visualization was tested in human MONOMAC 6 AMLcell line (with t(9;11)/MLL-AF9 mutation) via MTT cell proliferation/viability assay. There were 40 compounds that had $IC_{50}$ less than 50 μM, yielding a hit-rate of 18.8%. Top 20 compounds with prominent inhibitory effects on cell viability were chosen for further study.

The anti-leukemia effects of the top 20 compounds were re-evaluated in another two leukemia cell lines with high FTO abundance, NOMO-1 (carrying t(9;11)(q23;p22) alteration) and U937 (carrying t(10;11)(p13;q14) alteration. Additionally, the inhibitory effect of these compounds on the demethylation activity of FTO protein via $m^6A$ demethylase activity assay in cell free system was assessed. Based on the results derived from the biological functions in AML and the suppressive effects on FTO's demethylase activity, we focused on compounds of formula (I), (II), and their analogs.

Example 2: Anti-Leukemia Effects in AML Cells of Compounds of Formula (I) and (II) in Leukemia Cells with High and Low FTO Expression FTO levels in various leukemia cells including NOMO-1, MONOMAC 6 (MM6), U937, and K562 are shown in FIG. 1. NOMO-1, MONOMAC 6 (MM6), and U937 cells have higher FTO expression, and K562 cells have lower FTO expression. These levels were previously determined (8, 11).

Figure 2A:
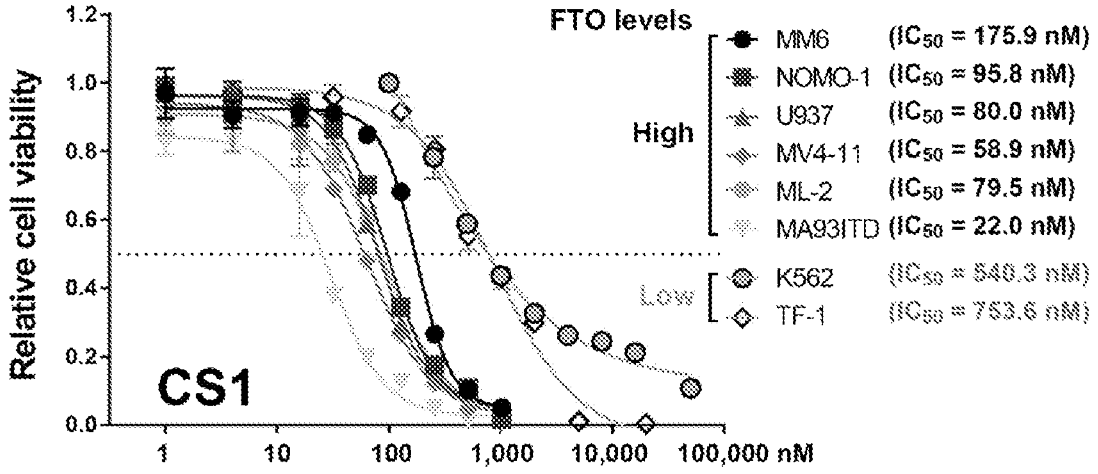
FIGS. 2A-F show effects of inhibition of compounds of formula (I) and (II) (CS1 and CS2 respectively) on viability of AML cells and healthy cells.
Figure 2B:
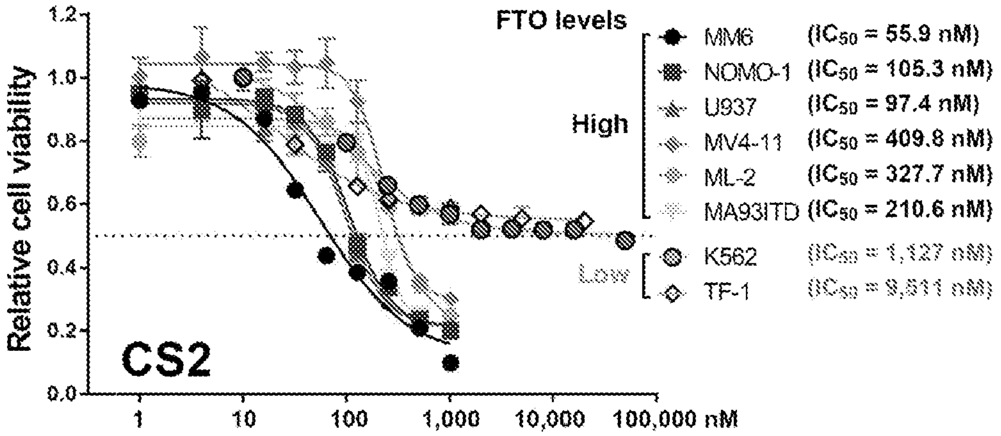

Inhibitory effect of compounds of formula (I) and (II) on cell growth/proliferation was measured. The $IC_{50}$ values of compounds of formula (I) and (II) in leukemia cells with higher FTO expression, including NOMO-1, MONOMAC 6 (MM6), MV4-11, ML-2, MA9.3ITD and U937, as well as the K562 and TF-1 cells with lower FTO expression, were determined. Analysis of $IC_{50}$ fitting curves revealed that the cells with high FTO expression always exhibited lower $IC_{50}$ values for compounds of formula (I) and (II), while cells with low FTO expression always exhibited higher $IC_{50}$ values (FIG. 2A, FIG. 2B). All the cells were treated with gradient inhibitors as indicated by the dots for 72 hours.

Figure 2C:
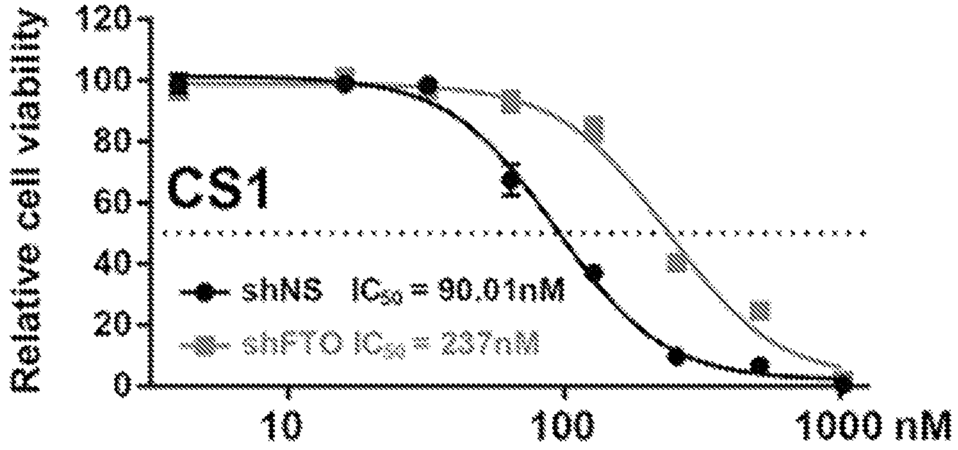
Figure 2D:
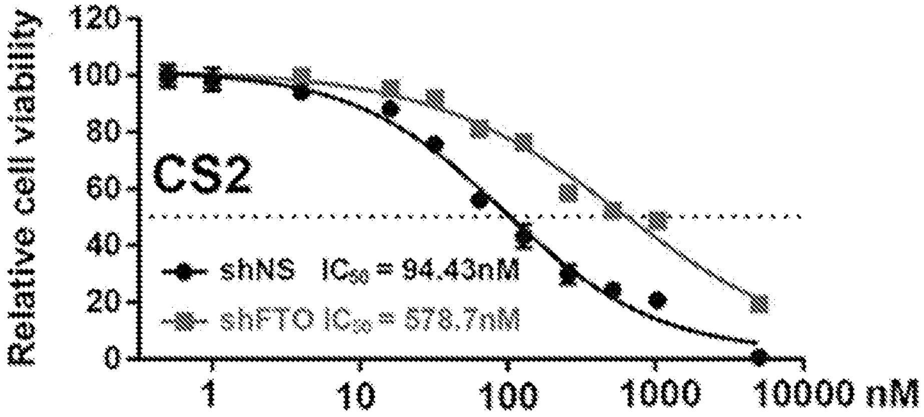

In addition, knockdown of FTO (shFTO) in AML cells with high FTO abundance (NOMO-1) decreased the sensitivity to compounds of formula (I) and (II) (FIG. 2C, FIG. 2D). These results suggest that the response to FTO inhibitors, compounds of formula (I) and (II), is dependent on FTO abundance in cellulo.

Figure 2E:
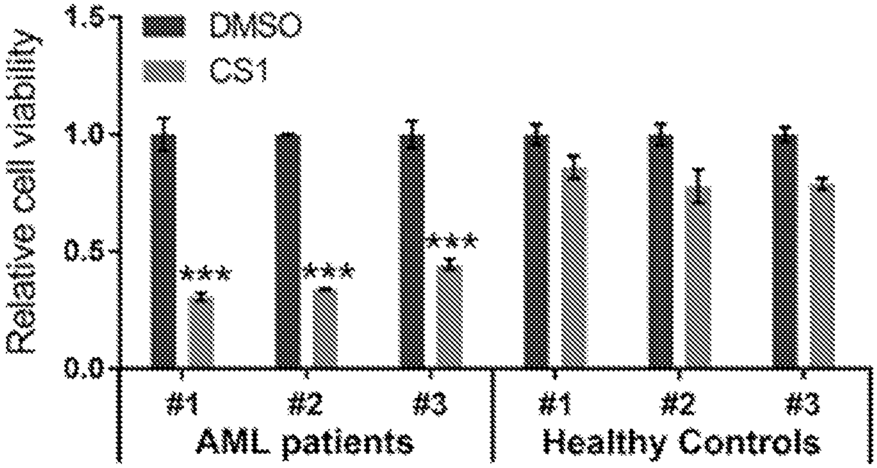
Figure 2F:
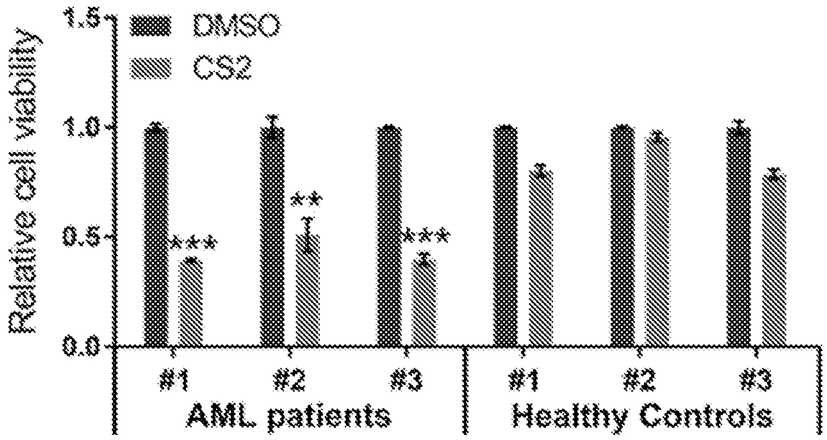
Figure 2G:
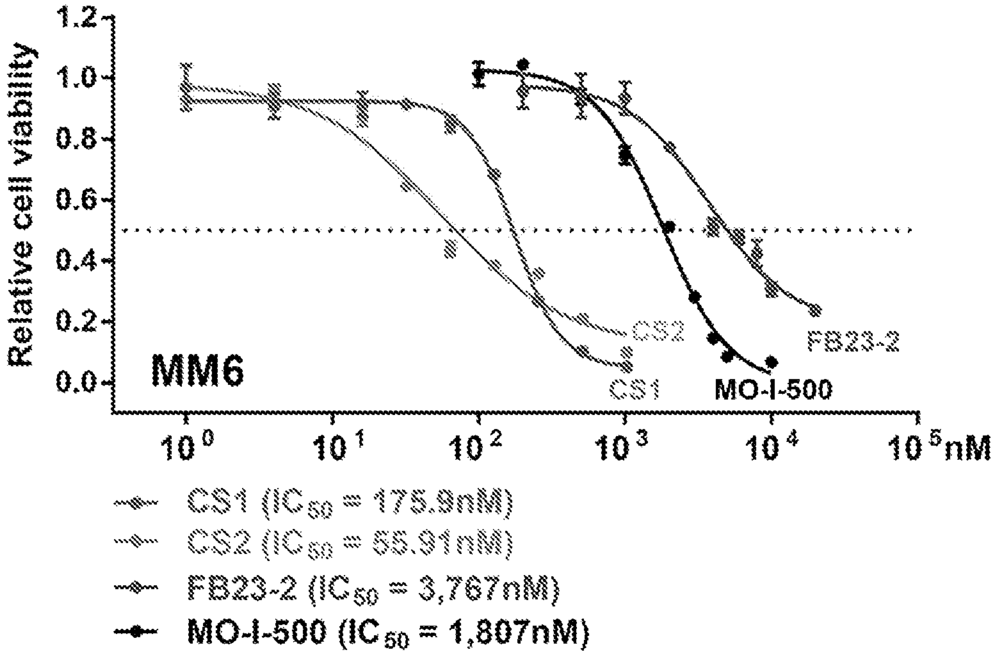
FIGS. 2G-H compares the effects of inhibition of previously reported FTO inhibitors (FB23-2 and MO-I-500) to FTO inhibitors of formula (I) (CS1) and (II) (CS2) on viability of AML cells.
Figure 2H:
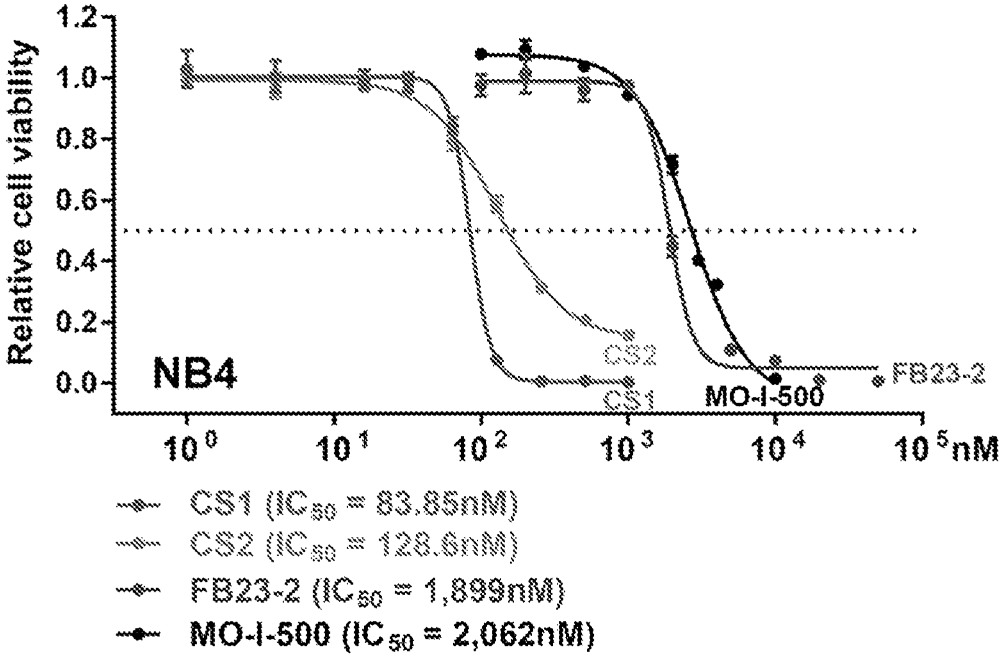

Compared with identified FTO inhibitors (e.g., FB23-2 and MO-I-500), compounds of formula (I) and (II) displayed much higher sensitivity for inhibiting cell viability. The $IC_{50}$ values of compounds of formula (I) and (II) are 10 to 30 times lower than that of FB23-2 or MO-I-500 (FIG. 2G, FIG. 2H), indicating the greatly improved therapeutic effects (in MM6 and NB4 cells).

Cell viability assays were also carried out to evaluate the effects of compounds of formula (I) and (II) on AML patient-derived and healthy donor-derived hematopoietic stem/progenitor cells ($CD34^+$ HSPCs). All the cells were treated with 100 nM compound of formula (I) and 200 nM compound of formula (II) for 48 hours. The two compounds significantly decreased cell viability of AML, but not in the healthy $CD34^+$ HSPCs (FIG. 2E, FIG. 2F), suggesting compounds of formula (I) and (II) display little obvious toxicity on normal cells. These data indicate that myeloid leukemia cells, in contrast to normal hematopoietic cells, are highly sensitive to small compounds mediated FTO inhibition.

Figure 3A:
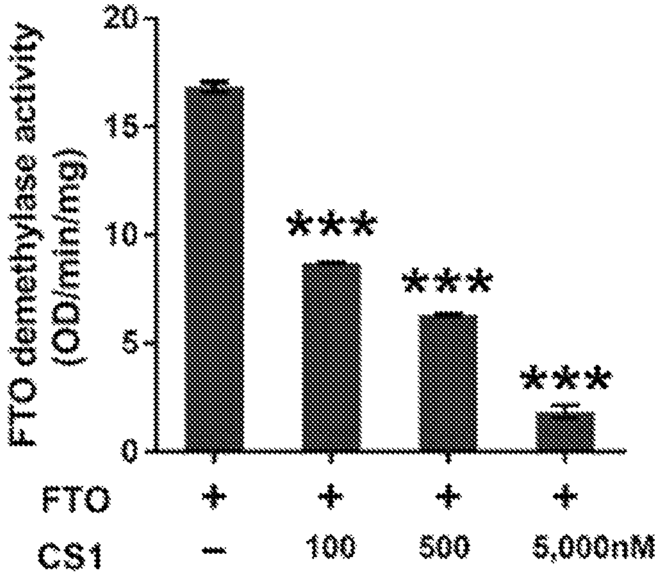
FIGS. 3A-C show the inhibitory effects of compounds of formula (I) (CS1) and (II) (CS2) on FTO demethylase activity in cell-free system (includes 1, 50, 100, 500, 1000, 5000 and 50000 nM concentrations of inhibitors). The experiments were done in triplicates to calculate the $IC_{50}$ values on inhibiting the demethylase activity of FTO protein.
Figure 3B:
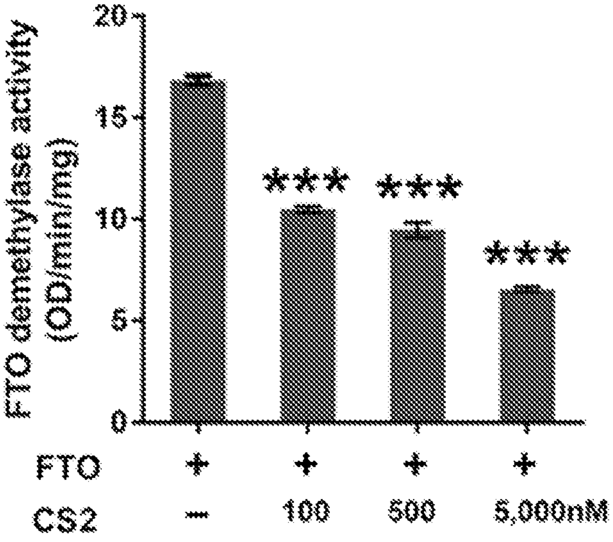
Figure 3C:
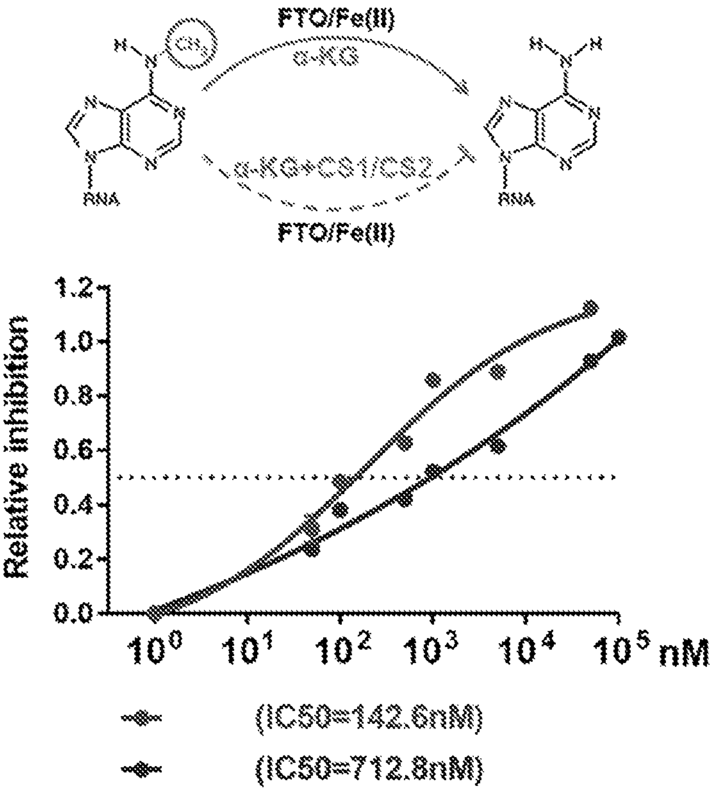

The demethylase activity of FTO with presence of compounds of formula (I) and (II) in cell-free system was assessed. In this study, 1, 50, 100, 500, 1000, 5000, and 50000 nM inhibitors were included. The experiments were repeated in triplicates to calculate the $IC_{50}$ values on inhibiting the demethylase activity of FTO protein. Both compounds of formula (I) and (II) suppressed the enzymatic activity of FTO protein (FIG. 3A, FIG. 3B), with $IC_{50}$ values at nanomolar levels (142.6 nM and 712.8 nM for compounds of formula (I) and (II) respectively, FIG. 3C). It was concluded that the therapeutic effects of potent FTO inhibitors, compounds of formula (I) and (II), in AML are dependent on their direct inhibition of the demethylase activity of FTO.

In contrast, treatment with compounds of formula (I) or (II) did not suppress the $m^6A$ demethylation activity of ALKBH5, another $m^6A$ demethylase, or the DNA demethylase activity of TET1, another α-KG-dependent dioxygenase, highlighting the selectivity of compounds of formula (I) and (II) as FTO inhibitors.

Example 3: Effects of Compounds of Formula (I) and (II) on AML Cell Apoptosis, Cell Cycle and Differentiation, as Well as on Self-Renewal of Leukemia Stem/Initiating Cells (LSCs/LICs)

AML is a heterogeneous disease with increased cell proliferation and impaired maturation of myeloid cells, and forced expression of FTO results in leukemogenesis via suppression of cell apoptosis and myeloid differentiation (8).

Figure 4A:
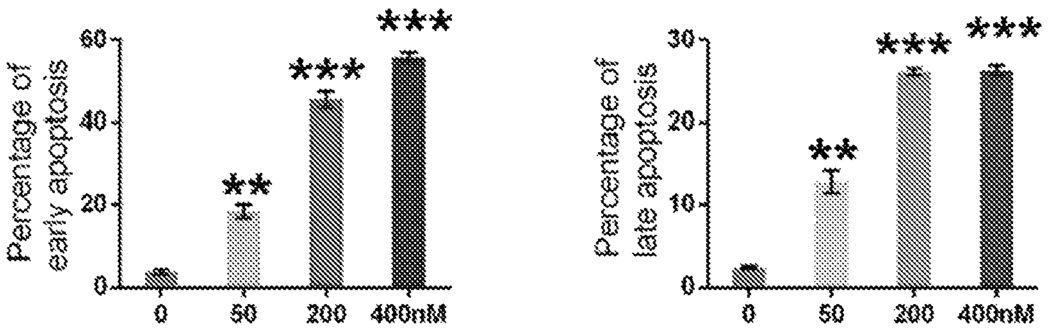
FIGS. 4A-I show effects of compounds of formula (I) (CS1) and (II) (CS2) on established leukemia cells and leukemia stem cells (LSCs).
Figure 4B:
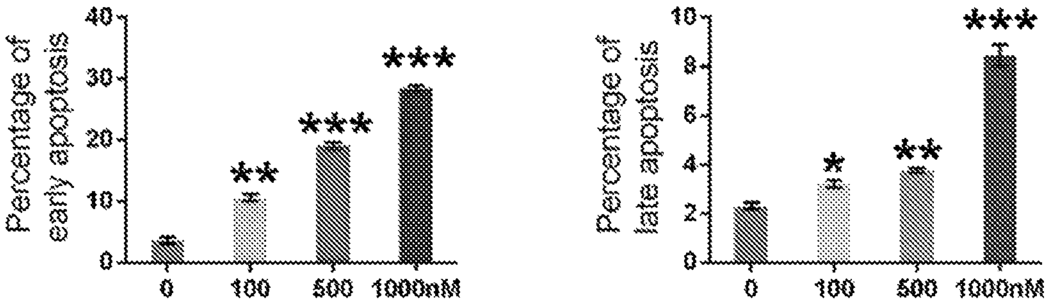
Figure 4C:
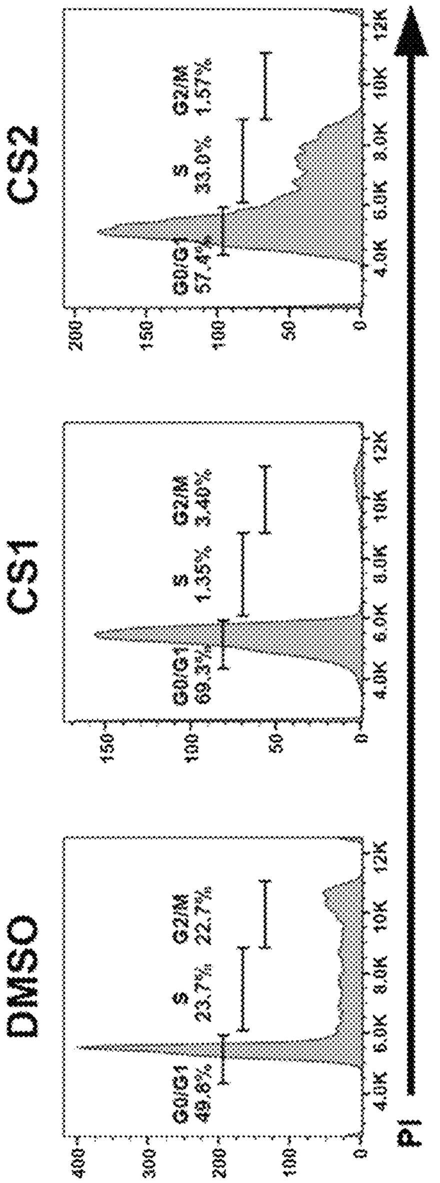
Figure 4D:
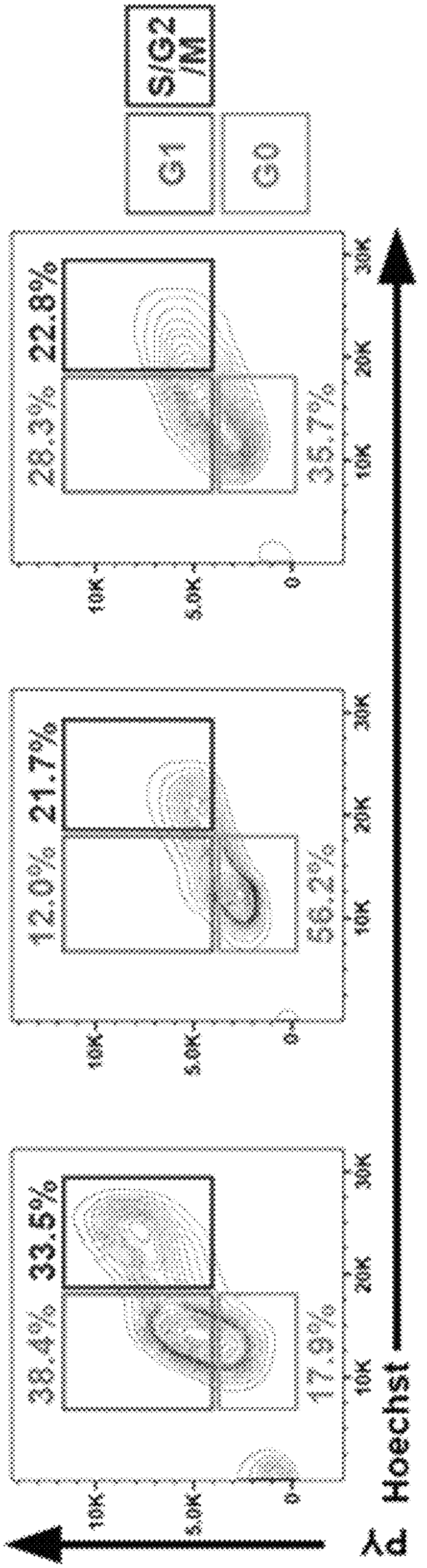

48 hour treatment with the two FTO inhibitors, compounds of formula (I) and (II), resulted in a dose-dependent increase in cell apoptosis of AML cell lines (NOMO-1 cells). The cells were treated with 50, 200, and 400 nM compound of formula (I) (FIG. 4A), or 100, 500, and 1000 nM compound of formula (II) (FIG. 4B). PI staining of NOMO-1 cells showed a reduction in the fraction of actively dividing cells (S/G2/M) and an increase in the fraction of quiescent cells (G0/G1), in other words cell cycle arrest was observed in G0/G1 and S stages (FIG. 4C). Cell cycle arrest in G0 phase was also detected by Hoechest 33342/Pyronin Y staining in NOMO-1 cells (FIG. 4D).

Figure 4E:
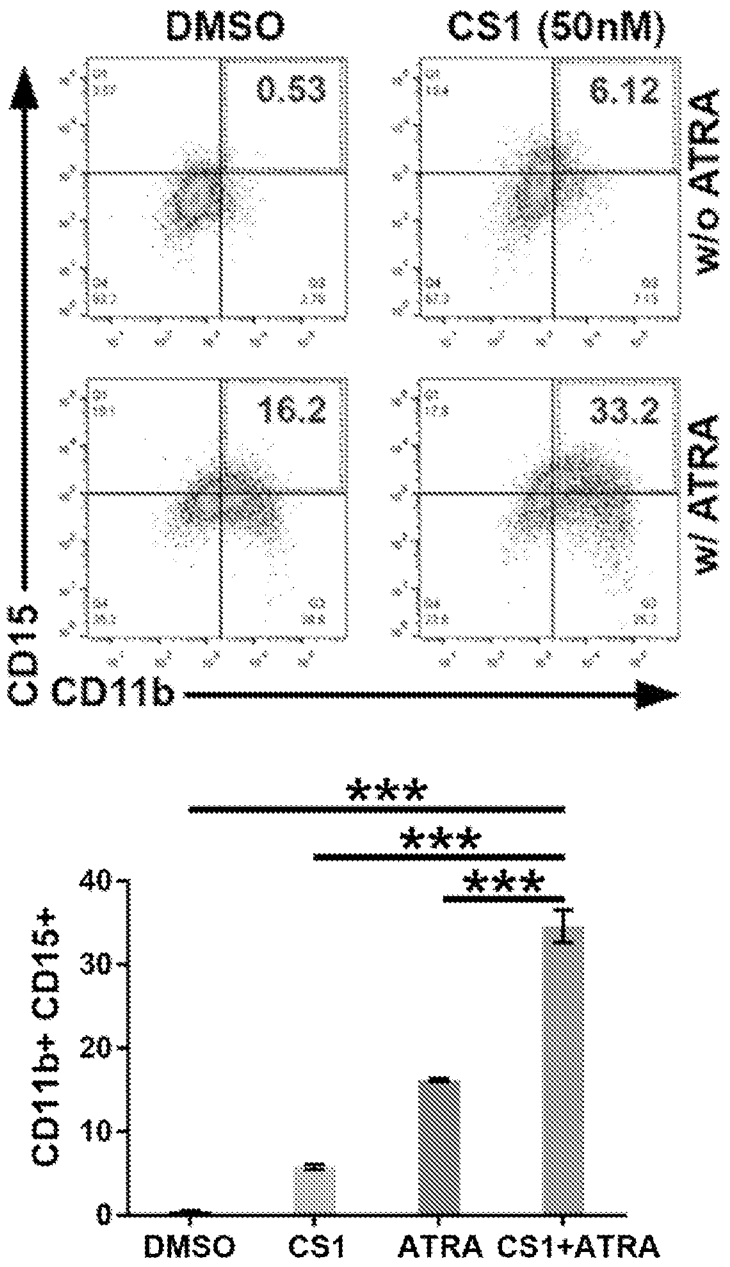
Figure 4F:
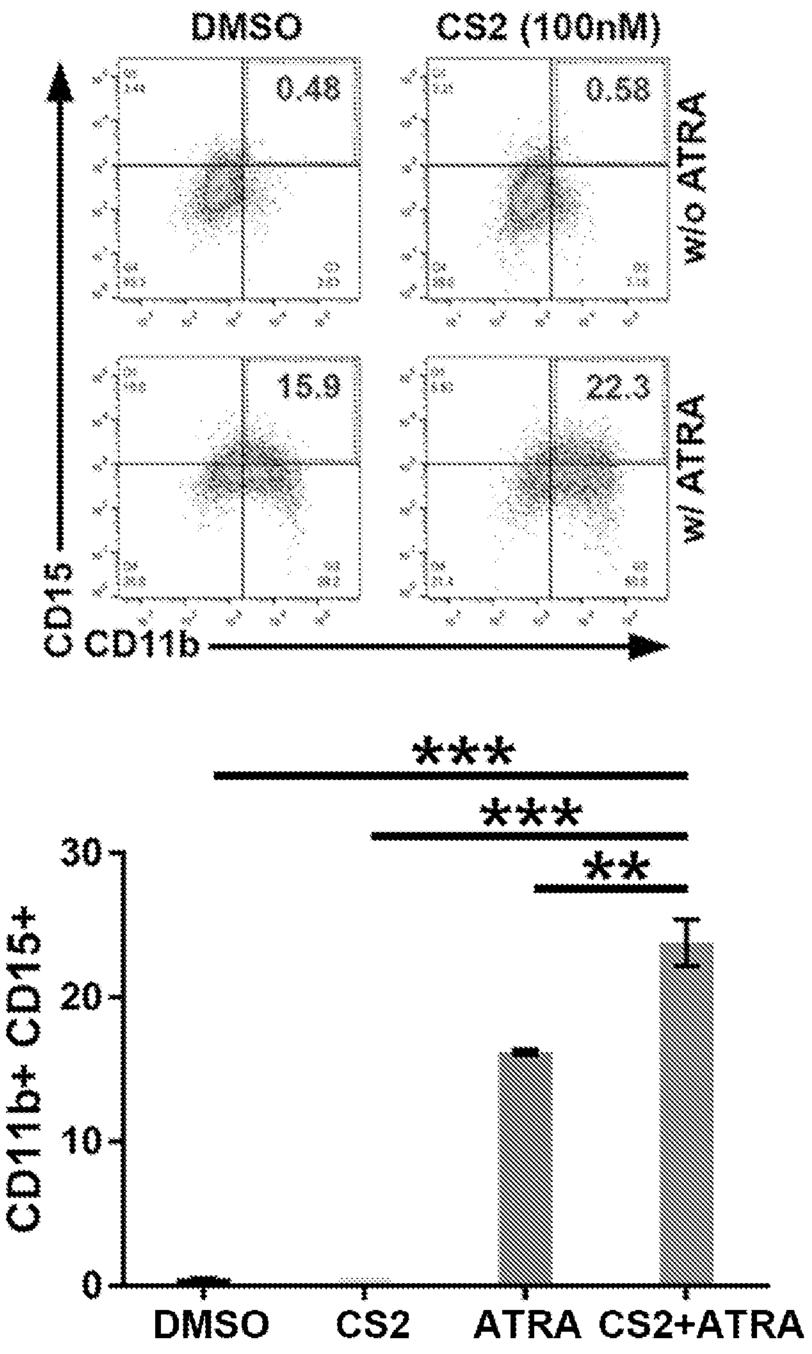

Additionally, both of the FTO inhibitors, compounds of formula (I) and (II), accelerated ATRA induced myeloid differentiation, in NB4 cells, via upregulating expression of myeloid differentiation markers, CD11b and CD14 (FIG. 4E, FIG. 4F). The cells were treated with 200 nM ATRA, 50 nM compound of formula (I) or 100 nM compound of formula (II) for 48 hours (All in vitro experiments were performed at least three times).

Unlike established leukemia cells, LSCs harbor the ability to self-renew and propagate disease upon serial transplantation, and are responsible for leukemia initiation and progression. Elimination or eradication of LSCs is necessary for curative therapy. Relative abundance of FTO protein in AML patient-derived LSCs ($CD34^+$ cells enriched from bone marrow mononuclear cells of AML patients) and normal hematopoietic stem and progenitor cells (HSPCs) was investigated to account for potential effects of FTO in LSCs.

Figure 4G:
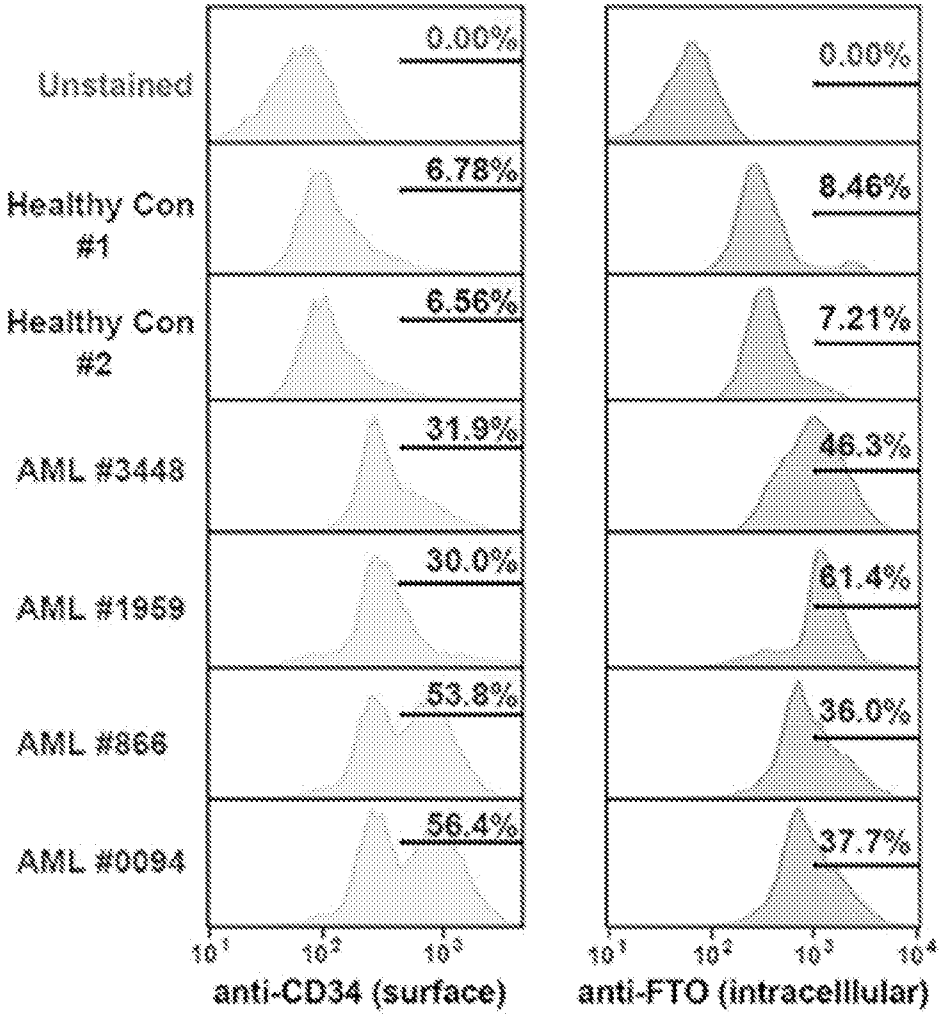
Figure 4H:
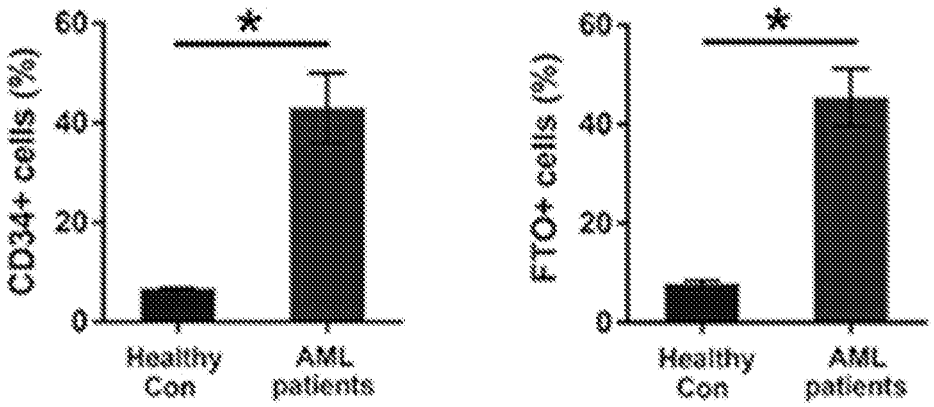
Figure 4I:
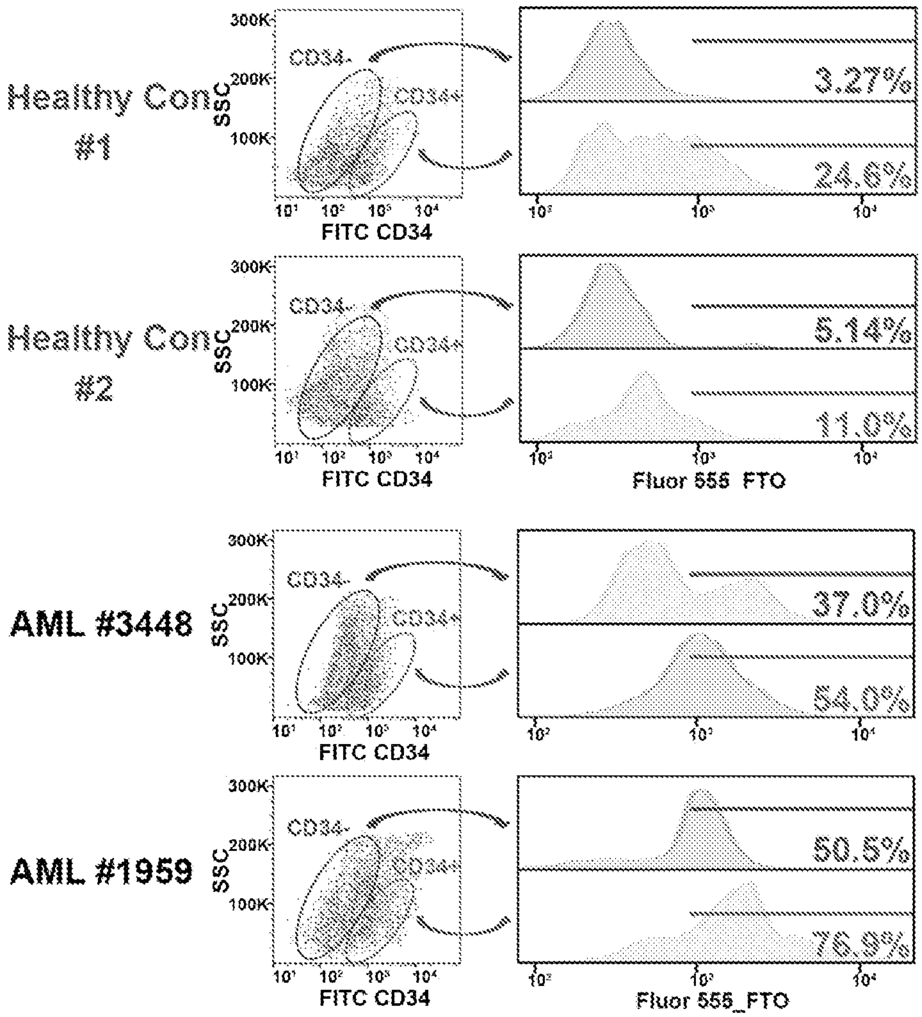

Via surface flow cytometry staining followed by intracellular staining, the aberrant high expression of FTO in AML patients compared with healthy donors was confirmed. Healthy controls represent the bone marrow monoclear cells (BMMNCs) from healthy donors; AML patient samples indicated BMMNCs from AML patients (FIG. 4G). Statistical results show the expression of CD34 marker and abundance of FTO in healthy control and AML patients (FIG. 4H). The whole population was then divided into two fractions, $CD34^+$ cells (representing LSCs, more immature blast AML cells) and $CD34^-$ cells (representing differentiated, bulk, leukemic cells), and abundance of FTO protein was determined, via intracellular staining, in $CD34^-$ cells and $CD34^+$ hematopoietic stem/progenitor cells in (HSPCs, healthy controls) or LSCs (AML patients). Relative higher expression of FTO in $CD34^+$ compared with $CD34^-$ cells was observed in all cells (FIG. 4I), while FTO level in $CD34^-$ AML cells was still higher than that in both healthy control $CD34^+$ and $CD34^-$ cells.

Given the increased abundance of FTO in AML cells and $CD34^+$ AML cells, we reasoned the critical oncogenic function of FTO both in established leukemic cells as well as in LSCs. The function of FTO on myeloid differentiation, cell apoptosis and colony forming activity of AML patients derived LSCs was evaluated. It was observed that leukemia differentiation following FTO knockdown is associated with increased cell apoptosis in AML patients. Knockdown of FTO also suppressed colony forming activity of AML primary cells, including decreased colony size and colony number, indicating the inhibitory effect of FTO knockdown on LSCs. In order to further interpret the effects of FTO on self-renew of LSCs, additional limiting dilution analysis experiments were performed with murine MLL-AF9 (MA9) and FLT3ITD/NPM1$^{mut}$ primary leukemic cells upon FTO knockdown and inhibition. shRNA mediated FTO knockdown or small compound induced FTO inhibition significantly suppressed self-renew activity of LSCs (Data not shown).

These results demonstrate that the oncogenic functions of FTO depend on its effects on both established leukemic cells and immature LSCs. Compounds of formula (I) or (II) mediated FTO inhibition results in myeloid differentiation, cell apoptosis, and cell cycle arrest in established leukemias, and attenuation on self-renewal activity of LSCs/LICs.

Example 4: Treatment with Compounds of Formula (I) and (II) Substantially Delayed Leukemia Progression and Improved Survival of AML Mice To evaluate whether FTO inhibition, mediated by compounds of formula (I) and (II), could delay onset of leukemia symptoms and prolong overall survival of AML mice, we exerted "human-in-mouse" xenograft mouse models with MA9.3ITD and NOMO-1 cells, AML Patient-derived Xenograft (PDX) model (xeno-transplanted with primary AML cells from a relapsed AML patient), and secondary bone marrow transplantation (BMT) with MA9 murine AML cells.

Figure 5A:
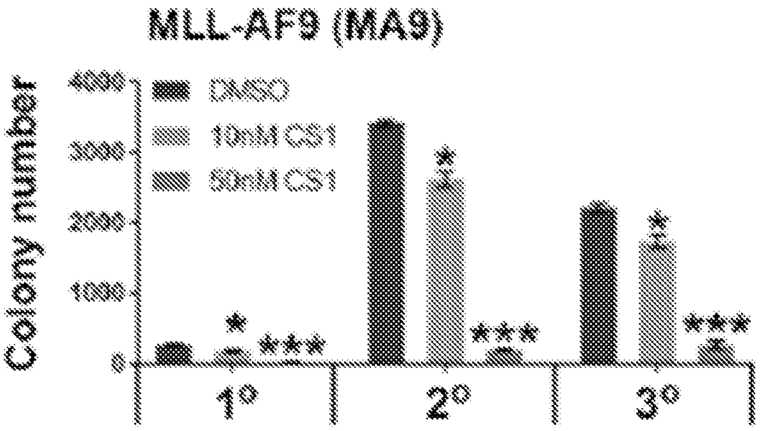
Figure 5B:
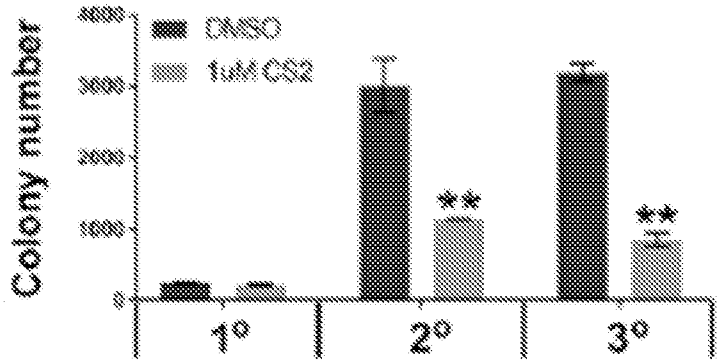
Figure 5C:
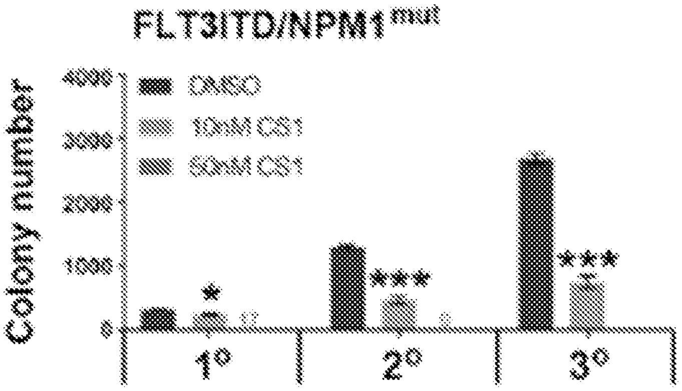
Figure 5D:
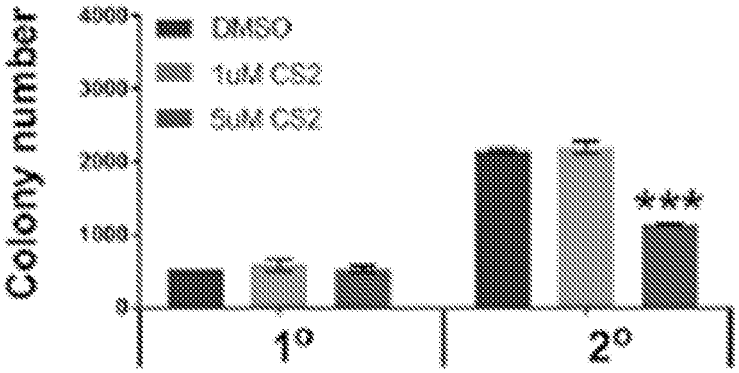

The effects of compounds of formula (I) and (II) in murine AML cells with high FTO expression, including MA9 and FLT3ITD/NPM1$^{mut}$ models, were evaluated. Colony forming assay (CFA) suggested that treatments with compounds of formula (I) or (II) decreased colony forming activity of MA9 and FLT3ITD/NPM1$^{mut}$ murine AML cells. 20,000 MA9 or FLT3ITD/NPM1$^{mut}$ leukemia cells were seeded for each generation and treated with DMSO or FTO inhibitors, compounds of formula (I) or (II). Treatment with compound of formula (I), at 10 nM and 50 nM, decreased the colony forming activity of primary murine MLL-AF9 (MA9) leukemic cells in vitro (FIG. 5A). Treatment with compound of formula (II), at 1 μM, decreased the colony forming activity of primary murine MLL-AF9 (MA9) leukemic cells in vitro (FIG. 5B). Treatment with compound of formula (I), at 10 nM and 50 nM, decreased the colony forming activity of murine FLT3ITD/NPM1$^{mut}$ leukemic cells (FIG. 5C). Treatment with compound of formula (II), at 1 μM and 5 μM, decreased the colony forming activity of murine FLT3ITD/NPM1$^{mut}$ leukemic cells (FIG. 5D).

Figure 5E:
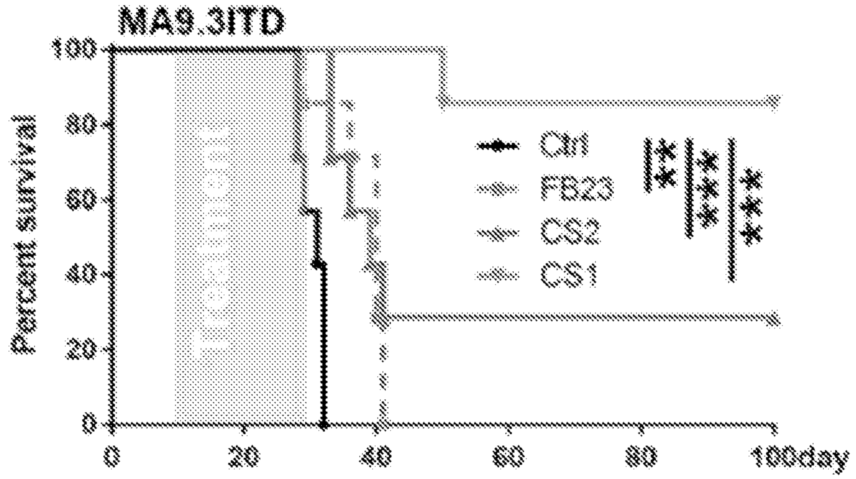
Figure 5F:
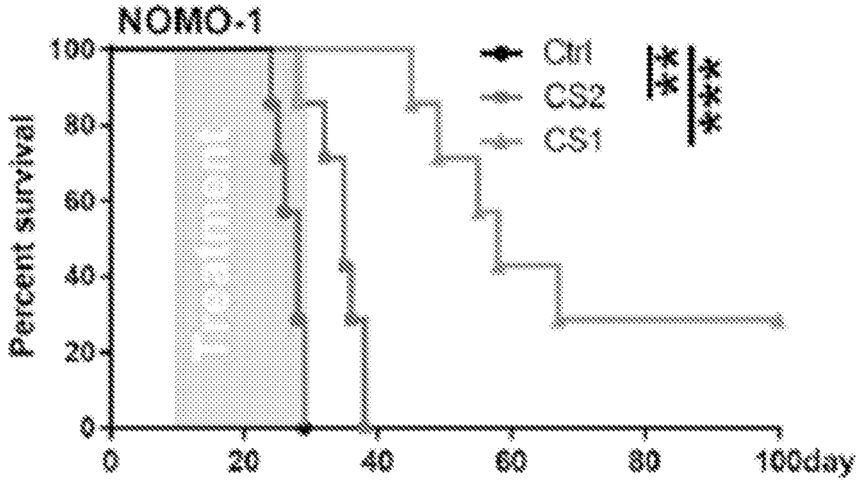

For xenograft AML models with NRGS mice, the leukemia AML cells, with high endogenous FTO expression, were pretreated with 100 nM FTO inhibitors for 48 hours before transplantation, and drug treatment was started at day 11 after transplantation. The FTO inhibitors, compounds of formula (I), (II), and FB23-2 were delivered (2 mg/kg/day) every other day by i.p. injection for a total of ten treatments. FIG. 5E depicts a Kaplan-Meier survival curve of xenograft mouse model transplanted with AML cells with high endogenous FTO expression (MA9.3ITD) which were pretreated with FTO inhibitors. FIG. 5F depicts a Kaplan-Meier survival curve of xenograft mouse model transplantated with AML cells with high endogenous FTO expression (NOMO-1) which were pretreated with FTO inhibitors. Results show that in xenograft mouse models transplanted with pretreated AML cells with high endogenous FTO expression, mice transplanted with AML cells pretreated with FTO inhibitors lived significantly longer than the control groups. Treatment with FTO inhibitors also relieved leukemia signs from peripheral blood and bone marrow, induced myeloid differentiation, and reduced splenomegaly.

Flow cytometry staining also confirmed that treatment with FTO inhibitors suppressed proliferation of human AML cells MA9.3ITD (hCD33 positive cells) in vivo and blocked engraftment of leukemia cells into peripheral blood, bone marrow, and spleen of NRGS recipient mice (FIG. 5G1, FIG. 5G2, FIG. 5G3). FB23-2, a previously reported FTO inhibitor with high sensitivity and specificity, was included in the in vivo study for comparison to with compounds of formula (I) and (II). Both compound of formula (I) and compound of formula (II) displayed much stronger anti-leukemic effects than FB23-2, as exhibited by improved overall survival, reduced spleen weight, and decreased engraftment (FIG. 5E, FIG. 5G1, FIG. 5G2, and FIG. 5G3). These findings attest to a high in vivo sensitivity of AML cells to FTO inhibitors, compounds of formula (I) and (II).

Figure 5I:
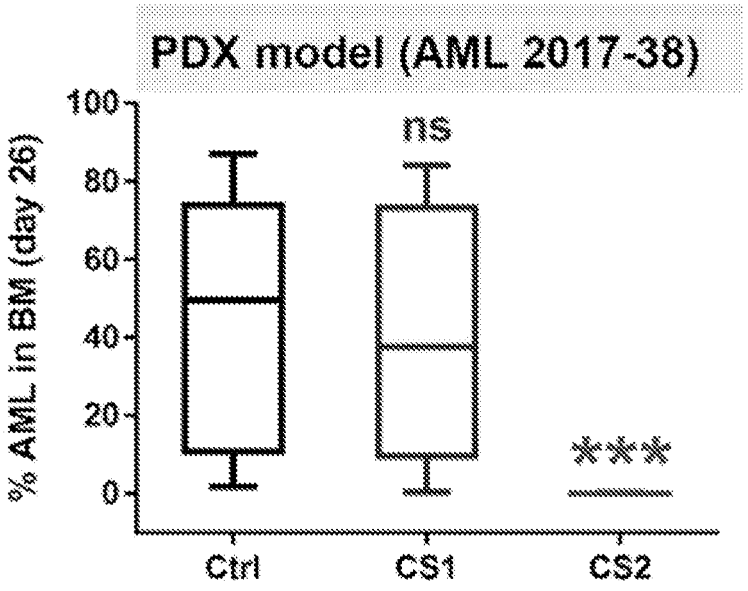

For AML PDX mouse model, $10^6$ cells were injected into NRGS mice and drug treatment (5 mg/kg/day, every other day treatment, 10 times in total) was started from day 8 after transplanatation. Both compound of formula (I) and compound of formula (II) were diluted in PBS and delivered into mice via i.p. injection. There was no pretreatment of AML patient cells with compounds of formula (I) and (II). FIG. 5H shows Kaplan-Meier survival curves of AML PDX mouse models upon treatment with compounds of formula (I) and (II). Curves show strong anti-leukemia effect of compound of formula (II), but unexpectedly not compound of formula (I). Additionally, engraftment of AML patient cells into bone marrow of recipient NRGS mice from PDX mouse model upon treatment with compounds of formula (I) and (II) (administered via i.p. injection) is depicted in FIG. 5I (the hCD45 and hCD33 positive cells were determined at day 26 after transplantation). Again, results show strong anti-leukemia effect of compound of formula (II), but not compound of formula (I). Previous studies have identified equal or even stronger anti-leukemia activity of compound of formula (I) compared with compound of formula (II).

Figure 6A:
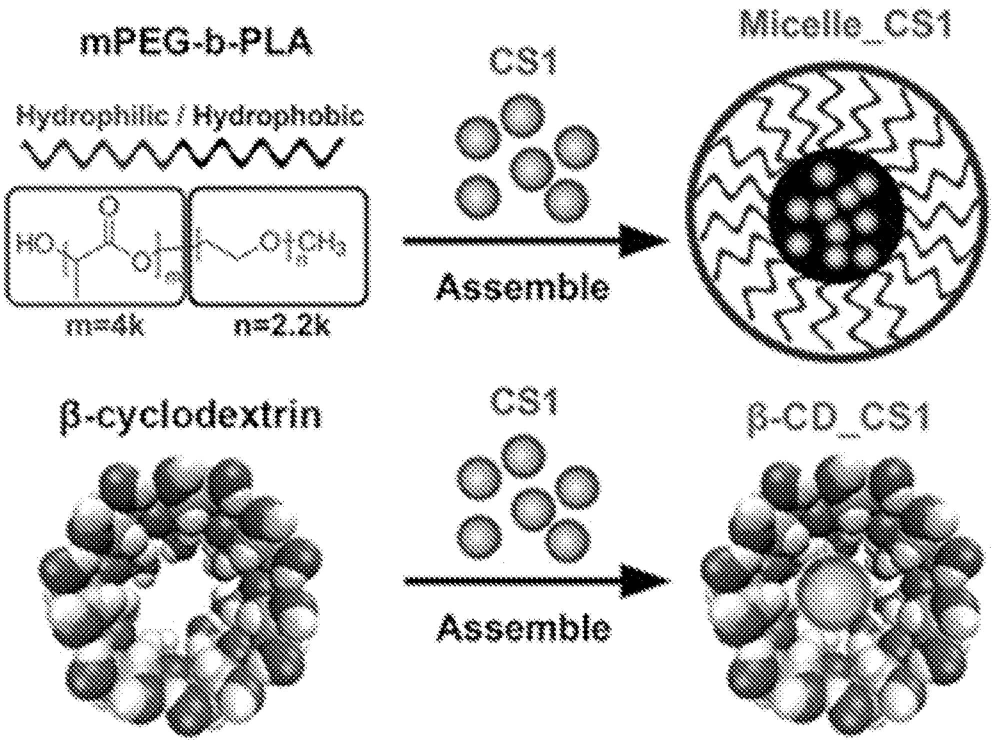
FIGS. 6A-F show effects of compound of formula (I) (CS1) on leukemia progression and survival of AML mice, when the compound is administered into mice inside micelles or β-cyclodextrin.

Example 5: Bioavailability of Compound of Formula (I) Greatly Increased when Delivered Inside Micelles or β-Cyclodextrin, Substantially Delaying Leukemia Progression and Improving Survival of AML PDX Mouse Models Mice from PDX mouse model were treated with compound of formula (I) via i.p. injection and later dissected. Multiple yellow/orange crystals were detected in their abdomen, indicating the extreme low solubility and uptake of compound of formula (I). To increase bioavailability of compound of formula (I), methoxy poly(ethyleneglycol)-b-poly(D,L-lactide) mPEG-b-PLA micelle or β-cyclodextrin was used to deliver the hydrophobic compound of formula (I) during in vivo study (FIG. 6A).

Figure 6B:
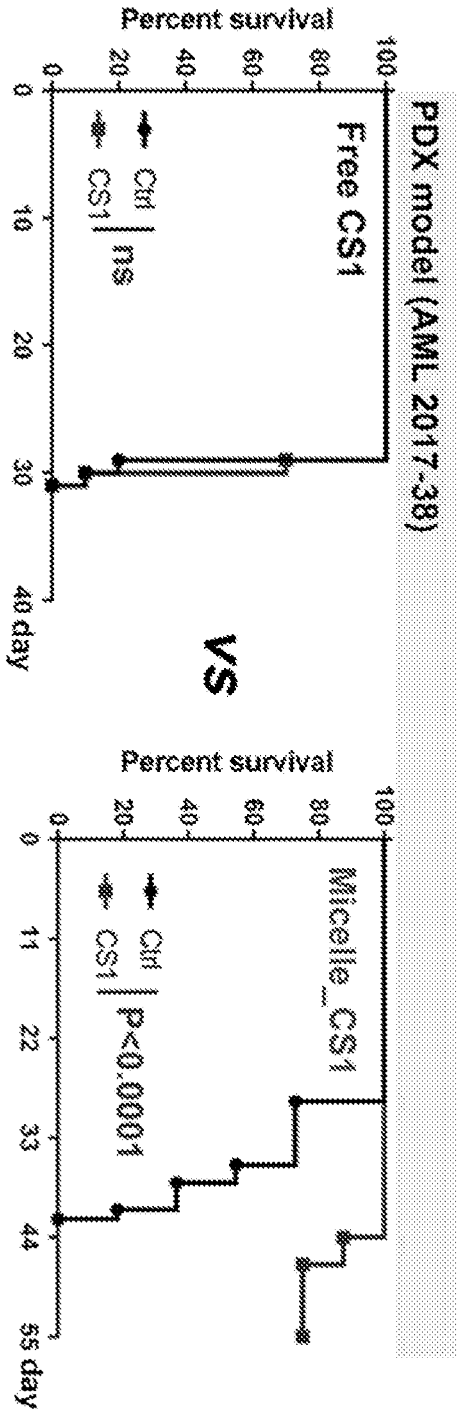
Figure 6C:
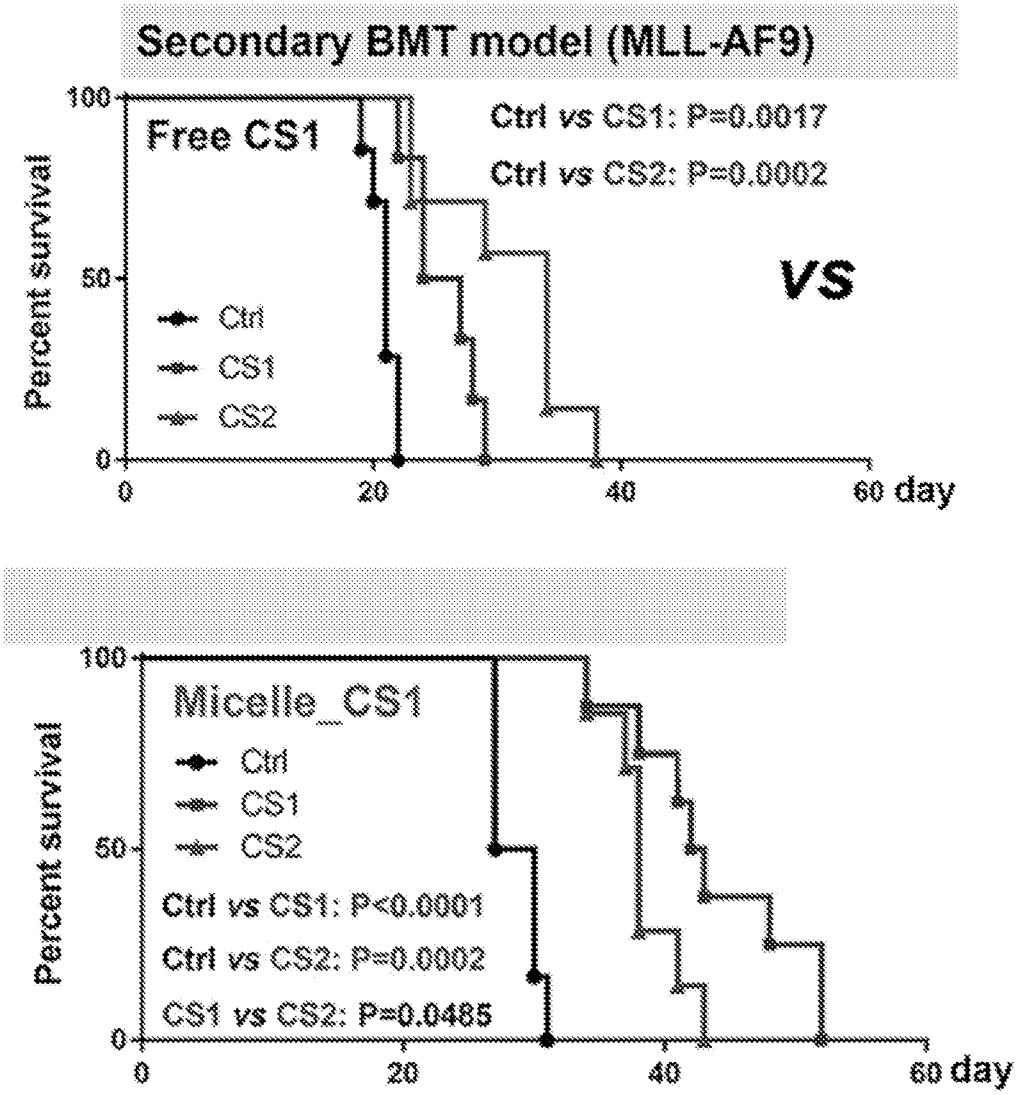
Figure 6D:
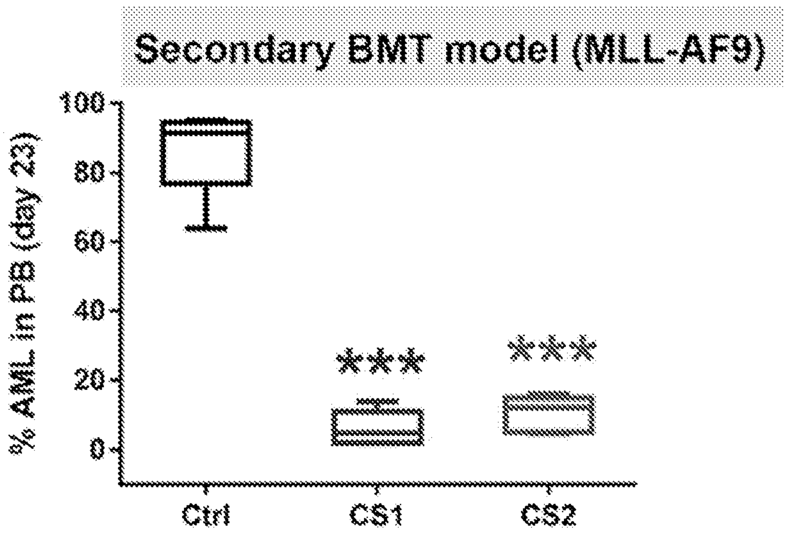
Figure 6E:
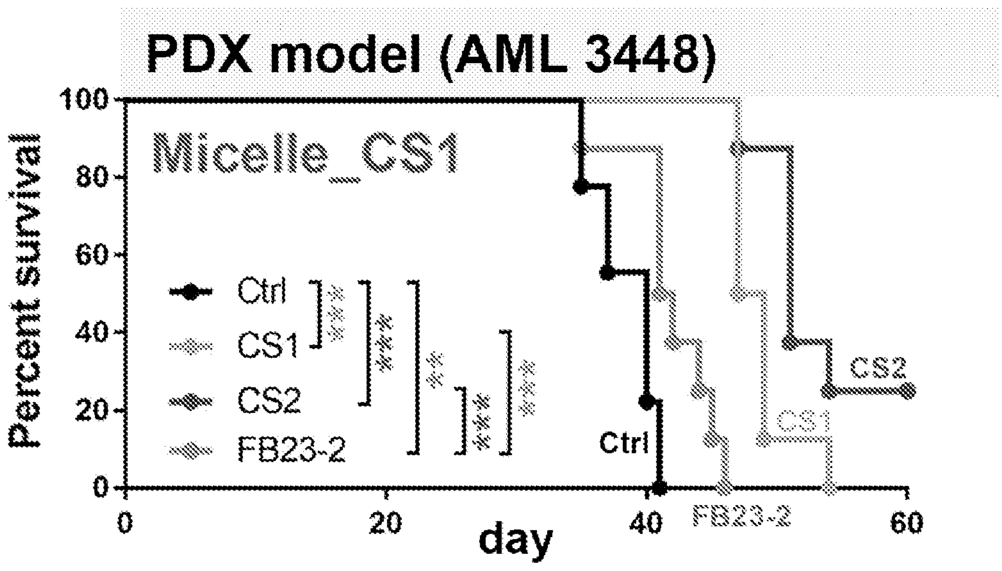
Figure 6F:
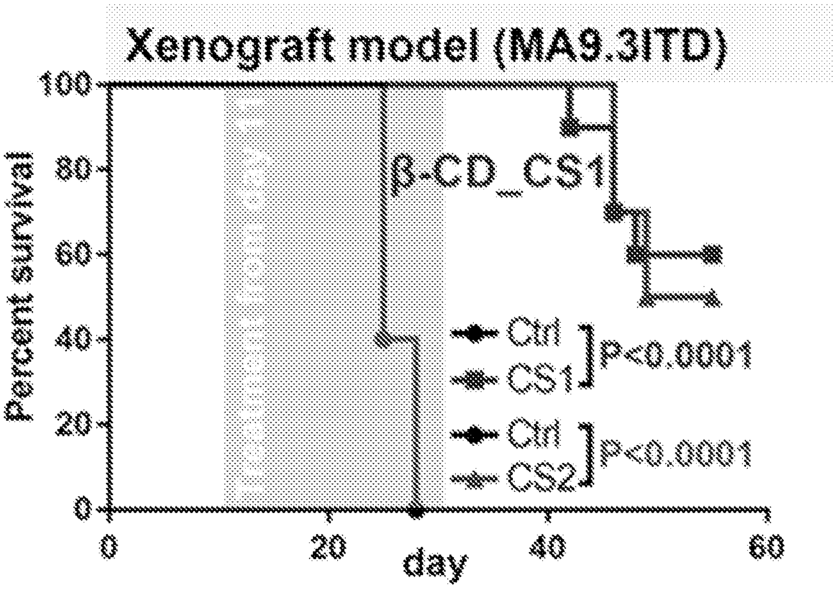

AML PDX mouse models were treated, via i.p. injection, with free compound of formula (I) and via i.v. injection with micelle enclosing the compound of formula (I). Kaplan-Meier survival curves show that delivery of compound of formula (I) enclosed within polymeric micelles of mPEG-b-PLA largely improved its anti-leukemia activity (FIG. 6B). The treatment strategy for both free compound of formula (I) and micelle enclosing the compound of formula (I) is the same as in FIG. 5H. The experiment was repeated with secondary BMT with MA9 leukemic cells. Anti-leukemia effects of compound of formula (II) were compared with free compound of formula (I), and micelle enclosed compound of formula (I). The compounds were delivered 7 days after transplanatation (5 mg/kg/day), every other day by i.p. injection (compound of formula (II) and free compound of formula (I)) and via i.v. injection (micelle enclosed compound of formula (I)) for a total of ten treatments. Kaplan-Meier survival curves of secondary BMT with MA9 leukemic cells from two repeated experiments after vehicle or FTO inhibitors treatment are shown in FIG. 6C. Secondary BMT with murine MA9 cells further showed the promising anti-leukemia effects of FTO inhibitors in delaying leukenogenesis and improving survival, and also identified that bioavailability of compound of formula (I) greatly increased when it was delivered inside micelles. FIG. 6D depicts the engrafting (CD45.2+ cells) of donor cells into peripheral blood of CD45.1 recipients, upon treatment with compound of formula (II) or micelles enclosing compound of formula (I), from secondary BMT with MA9 murine cells (the CD45.2+ cells were determined at day 29 after BMT). $1\times10^6$ mononuclear cells (MNCs) were isolated from bone marrow of the AML patients and transplanted into NRGS recipient mice. Drug treatment (5 mg/kg/day, every other day treatment, 10 times in total) was started from day 8 after transplantation. Kaplan-Meier survival curves of PDX model with AML cells after treatment with control, compound of formula (I) in micelles, compound of formula (II), or FB23-2 are shown in FIG. 6E. FIG. 6F shows Kaplan-Meier survival curves of xenograft mouse model with MA9.3ITD cells after treatment with control, compound of formula (II), or β-cyclodextrin enclosed compound of formula (I). Again, secondary BMT with murine MA9 cells showed the promising anti-leukemia effects of FTO inhibitors in delaying leukemogenesis, and increased bioavailability of compound of formula (I) when delivered in micelles or β-cyclodextrin.

Example 6: Compound of Formula (I) and (II) Induced FTO Inhibition, Increased Sensitivity to DNMT Inhibitors in AML Cells, Overcoming Hypomethylating Agents-Mediated Drug Resistance Besides maturation arrest and clonal proliferation of myeloid precursors, AML is also characterized by aberrant DNA methylation. DNMTs induced epigenetic silencing of crucial genes has been reported to contribute to leukemogenesis via disrupting cell apoptosis, cycle, and differentiation. Two DNMT inhibitors, azacitidine (5-azacytidine, AZA) and decitabine (5-aza-2'-deoxycytidine, DAC), are commonly used as single and standard chemotherapy agents to treat AML patients based on their ability to improve hematologic and quality of life parameters (27,28). However, in clinical trials, resistance to DNMT inhibitors, including primary resistance and secondary resistance, is almost a universal phenomenon, even though the related mechanism is far from complete. Recently, dynamic $m^6A$ modification has been reported to be an epigenetic driver of drug response, and deregulated FTO-$m^6A$ axis contributes to drug resistance in cancers, especially tyrosine kinase inhibitor (TKI)-induced drug resistance.

To evaluate whether combinational strategy with FTO inhibitors and hypomethylating agents could achieve much more powerful anti-leukemic effects than single treatment in human and murine AML cells with high FTO expression, compounds of formula (I) and (II) were combined with DNMT inhibitor (AZA or DAC).

Figure 7A:
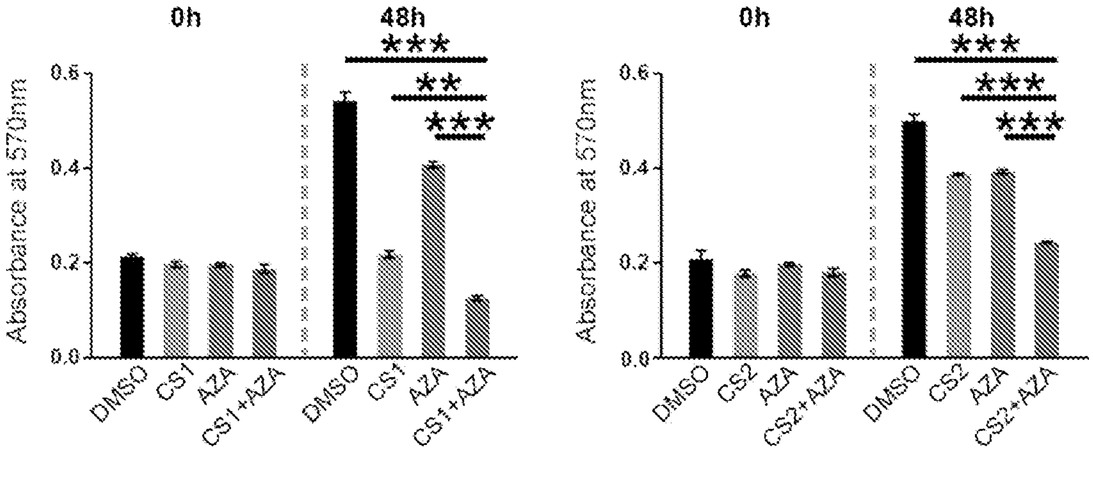
FIGS. 7A-I show effects of compound of formula (I) (CS1) and (II) (CS2) on hypomethylating agents mediated drug resistance.
Figure 7B:
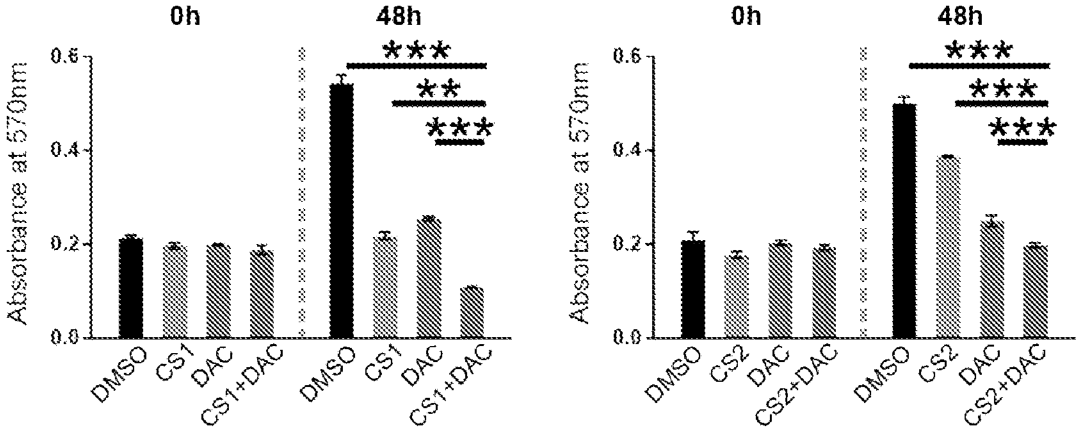
Figure 7C:
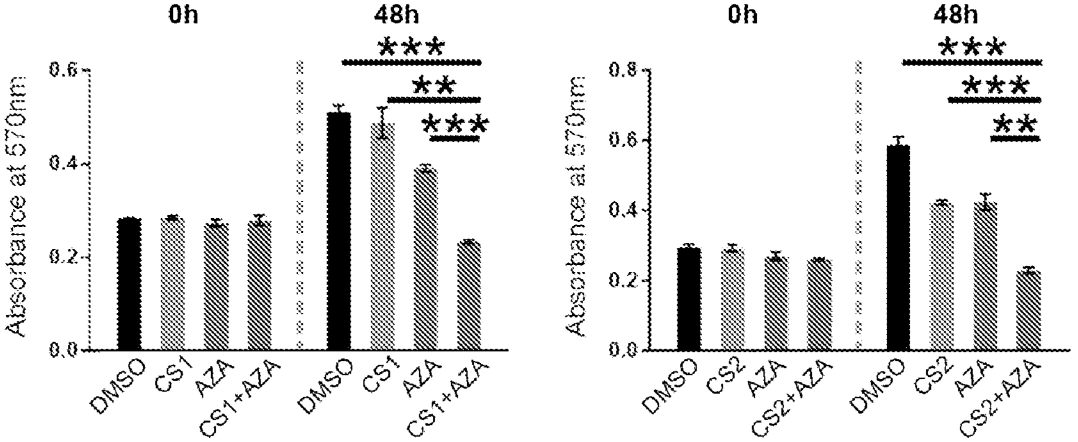
Figure 7D:
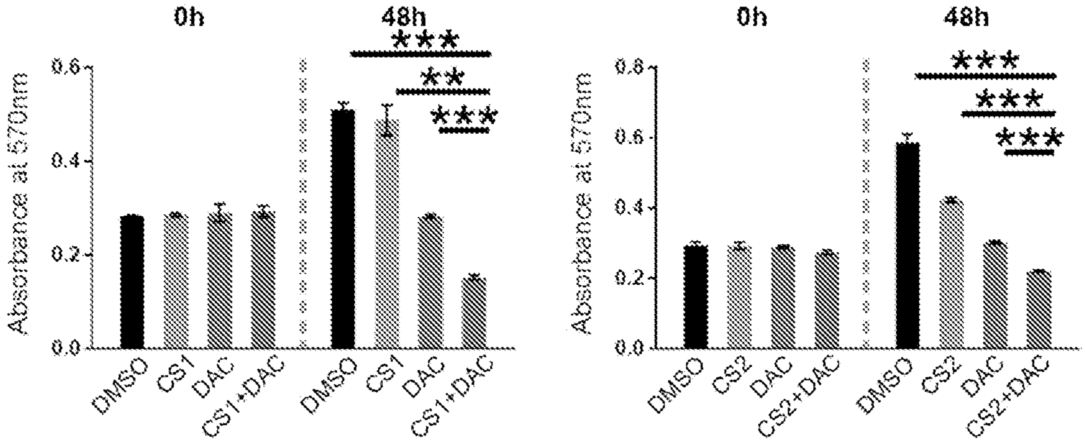

NOMO-1 cells were treated with 128 nM compound of formula (I), 256 nM compound of formula (II), 1000 nM AZA, 100 nM DAC, or their combinations for 48 hours. Cell proliferation was measured. FIG. 7A shows synergistic inhibitory effect on cell growth between compound of formula (I) or (II) and AZA. FIG. 7B shows synergistic inhibitory effect on cell growth between compound of formula (I) or (II) and DAC. This experiment was repeated with NB4 cells. FIG. 7C shows synergistic inhibitory effect on cell growth between compound of formula (I) or (II) and AZA. FIG. 7D shows synergistic inhibitory effect on cell growth between compound of formula (I) or (II) and DAC. Synergistic inhibitory effect of FTO inhibitor together with DNMT inhibitor on cell proliferation was observed.

Figure 7E:
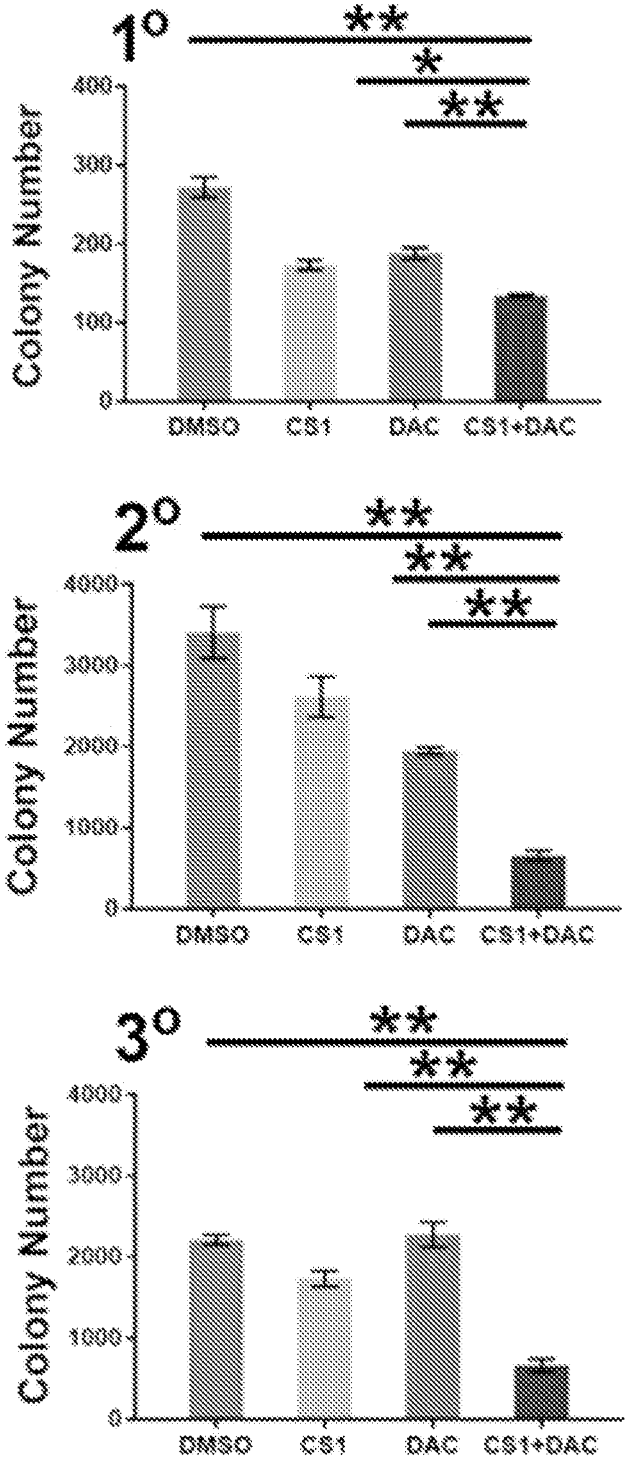

MA9 murine leukemic cells were used for colony forming assay. For each generation, 20,000 cells were seeded and treated with DMSO, 10 nM compound of formula (I), 20 nM DAC, and 10 nM compound of formula (I)+20 nM DAC. Combination of FTO inhibitor and DNMT inhibitor resulted in more significant efficacy on suppression of colony forming activity than either therapy alone (FIG. 7E). Serial colony forming assays demonstrated the synergistic effect between FTO inhibitor (compound of formula (I)) and DNMT inhibitor decitabine (DAC).

Although DNA hypomethylation is recognized to relieve repression of classic tumor suppressor genes, there are multiple evidences showing that DNMT inhibitor treatment induces expression of immune checkpoint genes (PD-L1, PD-L2, CTLA4, and PD-1) in AML or MDS cells, and in AML or MDS patients' peripheral blood mononuclear cells (PBMNCs) (29). Up-regulation of these immune suppressive molecules leads to immune evasion, which may contribute to drug resistance to hypomethylating agent.

Figure 7F:
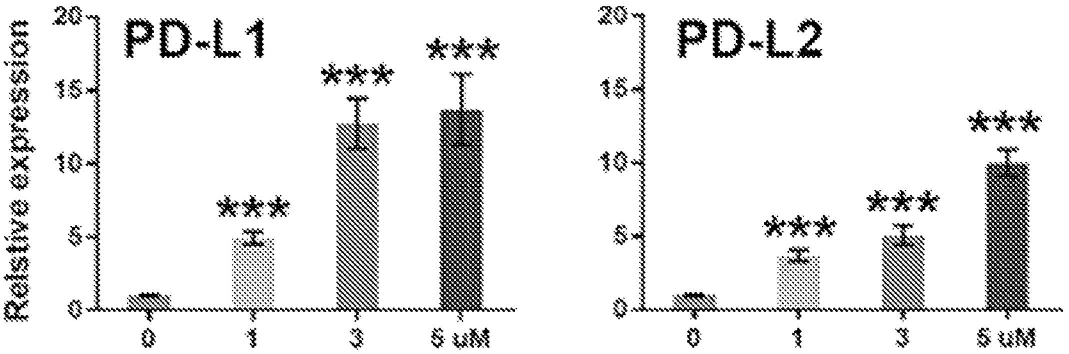
Figure 7G:
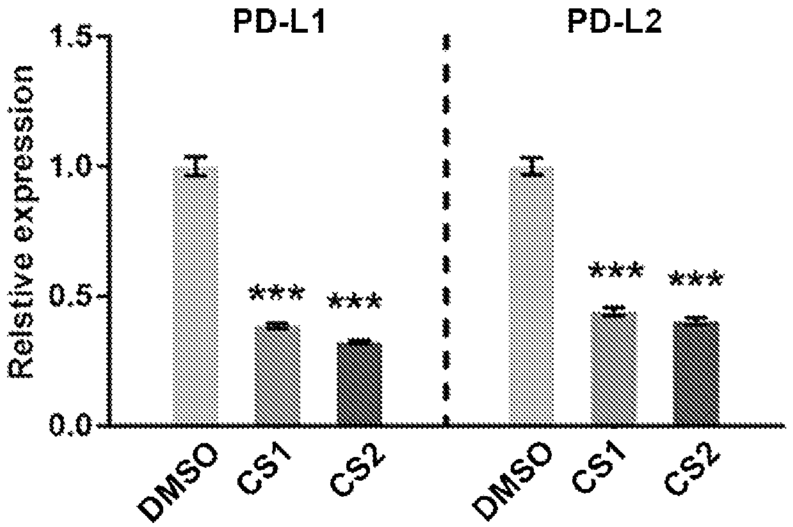

Expression of PD-L1, PD-L2, and $m^6A$ abundance upon DNMT inhibitor treatment in AML cells was analyzed. MONOMAC 6 cells were treated with PBS, 1 μM, 3 μM, and 5 μM DAC for 48 hours. DAC induced expression of PD-L1 and PD-L2 in a dose dependent manner i.e. the treatment induced up-regulation of immune checkpoint genes PD-L1 and PD-L2 (FIG. 7F). On the other hand, compound of formula (I) and (II) mediated FTO inhibition induced down-regulation of PD-L1 and PD-L2 levels in NOMO-1 AML cells (FIG. 7G). In other words, FTO inhibition dramatically suppressed PD-L1 and PD-L2 expression.

Figure 7H:
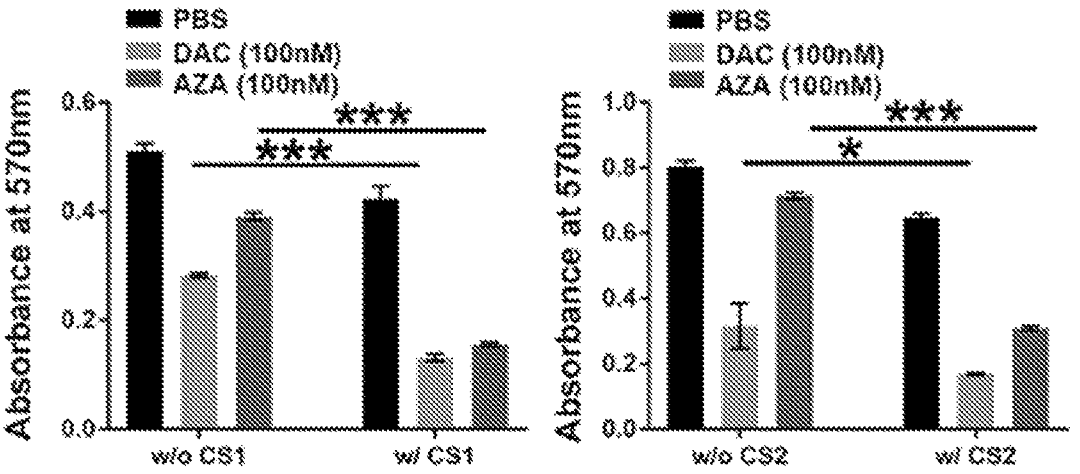

MONOMAC 6 cells were pretreated with 64 nM compounds of formula (I) or (II) for 48 hours. Response of the AML cells to 100 nM DAC or 100 nM AZA with or without pretreatment with compounds of formula (I) and (II) was measured. FIG. 7H shows increased inhibition in cell proliferation when cells are pretreated with either compound of formula (I) or (II). Thus, pretreatment of leukemia cells with compounds of formula (I) and (II) also sensitized them to DNMT inhibitors, which might depend on the inhibition of FTO.

Figure 7I:
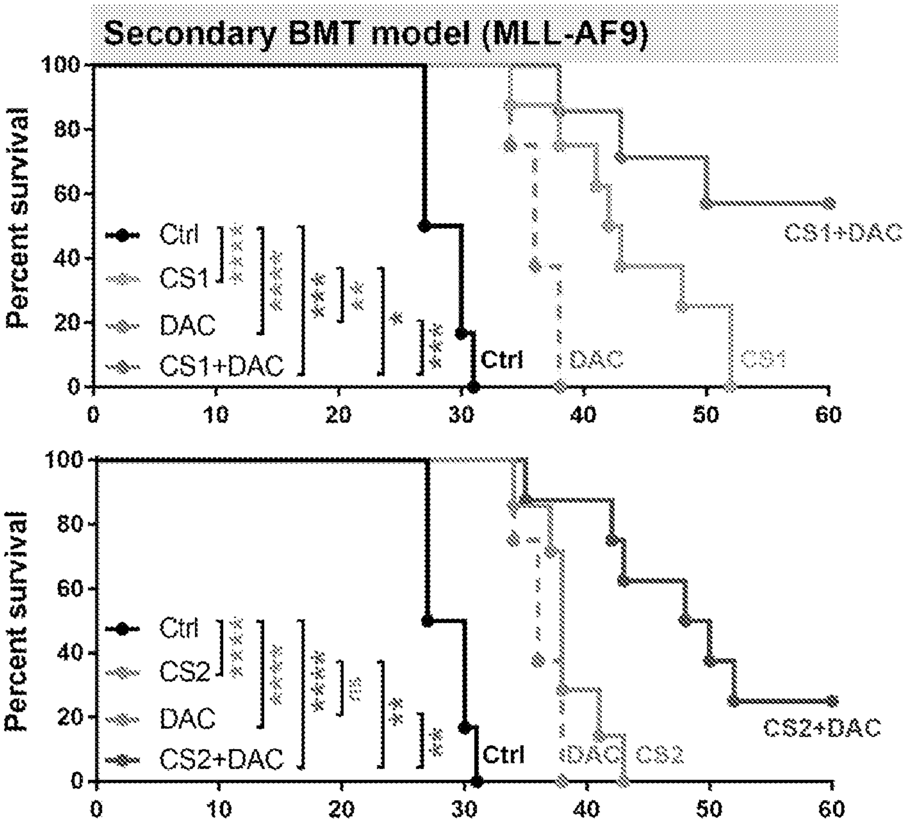

A study was carried out to examine the synergistic effects between FTO inhibitors and DNMT inhibitors in vivo. The study was done following secondary BMT with murine MA9 cells, where drug treatment was initiated 7 days after BMT. Treatment strategy for micelle enclosed compound of formula (I) and compound of formula (II): 5 mg/kg/day, every other day delivery, treatment for 10 times in total; i.v. injection for micelle enclosed compound of formula (I) and i.p. injection for compound of formula (II). Treatment strategy for DAC: 0.1 mg/kg/day, three times for one week, two weeks in total, i.p. injection. Kaplan-Meier survival curves of secondary bone marrow transplantation with MA9 leukemic cells following treatment with PBS (control), DAC, micelle enclosed compound of formula (I), compound of formula (II), or a combined treatment of—DAC with micelle enclosed compound of formula (I) or DAC with compound of formula (II) (FIG. 7I). This study further confirmed the synergistic effect between FTO inhibitors and DNMT inhibitors.

Chemotherapeutic therapy with DNMT inhibitors usually induces drug resistance via upregulating immune checkpoint genes, such as PD-L1 and PD-L2, and their elevated cellular levels confer acquired resistance to AZA and DAC (29). In AML, we observed that either DAC or AZA treatment resulted in upregulation of PD-L1/2, accompanied with increased expression of FTO, and decreased $m^6A$ abundance. Either small molecules induced FTO inhibition or shRNA mediated FTO knockdown could decrease PD-L1 or increase $m^6A$ abundance in dose dependent manner. Suppressed PD-L1 expression, reactivated immune response and prolonged overall survival of AML models. It was demonstrated that FTO inhibitors, compounds of formula (I) and (II), display synergistic effects with DNMT inhibitors when treating AML, and suppression of immune checkpoint genes by compounds of formula (I) and (II)⊣FTO⊣$m^6A$ axis could relieve universal drug resistance to DNMT inhibitors, probably due to inactivation of related immune inhibitory pathways.

Further studies were conducted to examine synergistic effects of compounds of formula (I) and (II) with other anti-cancer agents, and determine whether these compounds can sensitize cencer cells to other therapeutic agents and help overcome drug resistance. It was observed that compounds of formula (I) and (II) sensitize AML cells to all-trans retinoic acid (ATRA), daunorubincin (DNR), Cytarabine (Ara-C), 5-Azacytidine (Aza) and 5-aza-2'-deoxycytidine (DAC), and sensitize GBM cells to temozolomide (TMZ). In addition, it was observed that compounds of formula (I) and (II) overcome TKI resistance in TKI-resistant human KASUMI-1 and MV4-11 AML cell lines, and that compounds of formula (I) and (II) also synergize with TKI in inhibiting viability of human AML cells. Furthermore, it was observed that IDH-mutant AML cells collected from patients resistant to IDH inhibitors are also sensitive to treatment with compounds of formula (I) and (II). There is also a synergistic effect between compounds of formula (I) and (II) and IDH inhibitor in treating IDH-mutant AML cells. Such data collectively suggest that FTO is a master mediator of drug response and pharmacological inhibition of FTO can sensitize cancer cells to other therapeutic agents and overcome drug resistance.

Example 7: Therapeutic Effects of FTO Inhibitors in Solid Tumors

Figure 8A:
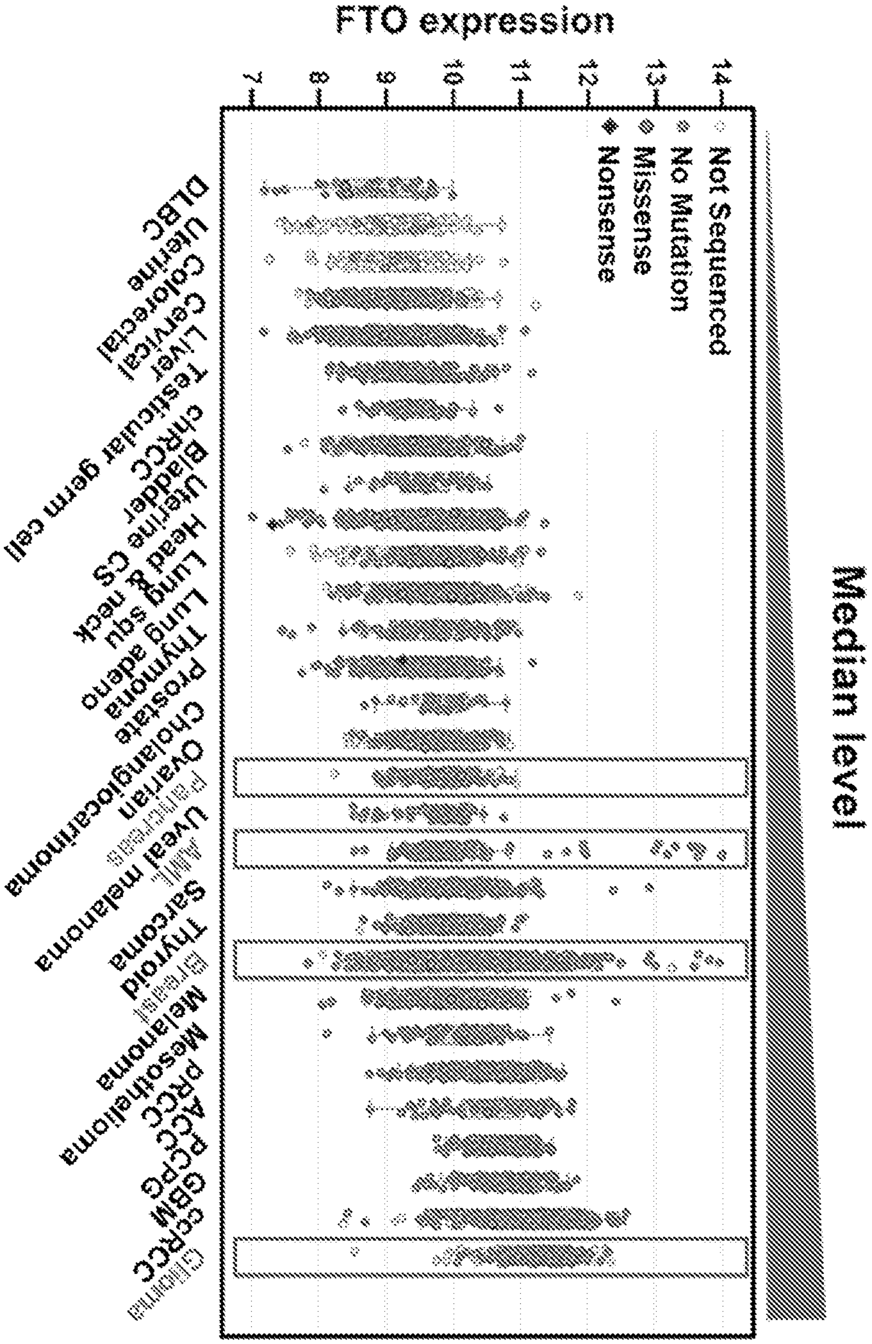
FIGS. 8A-D show effects of compounds of formula (I) (CS1) and (II) (CS2) on solid tumors.
Figure 8B:
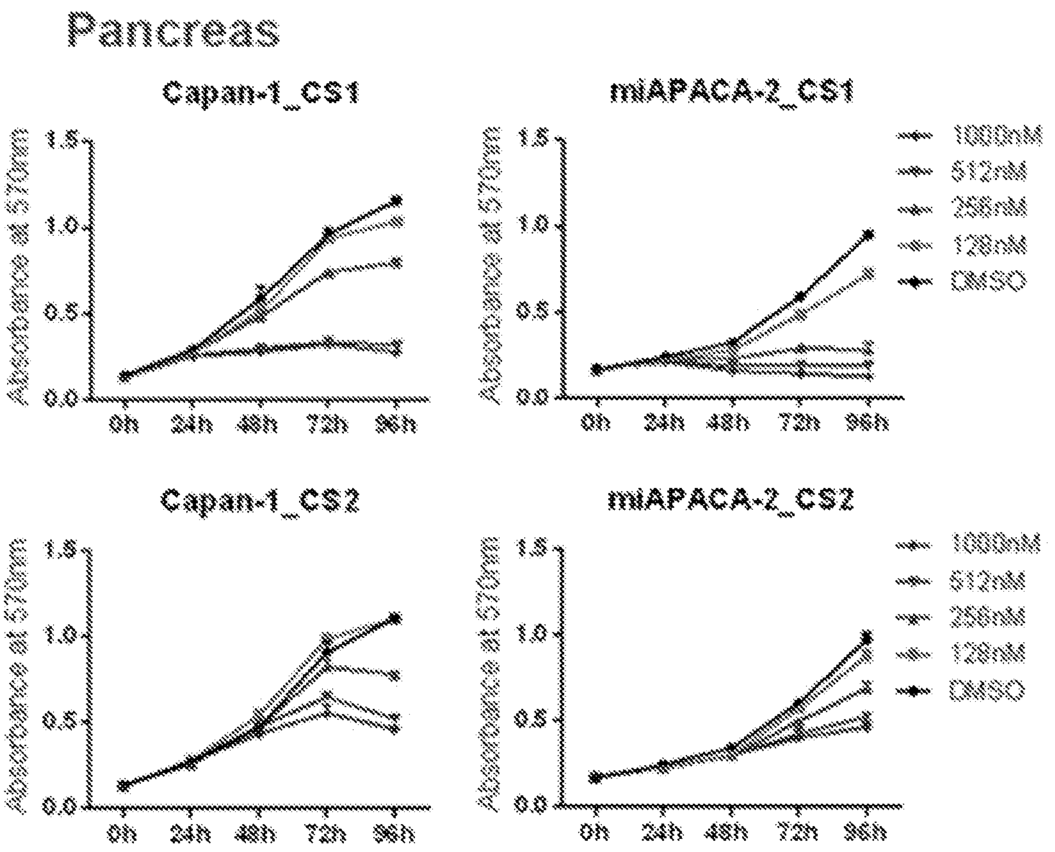
Figure 8C:
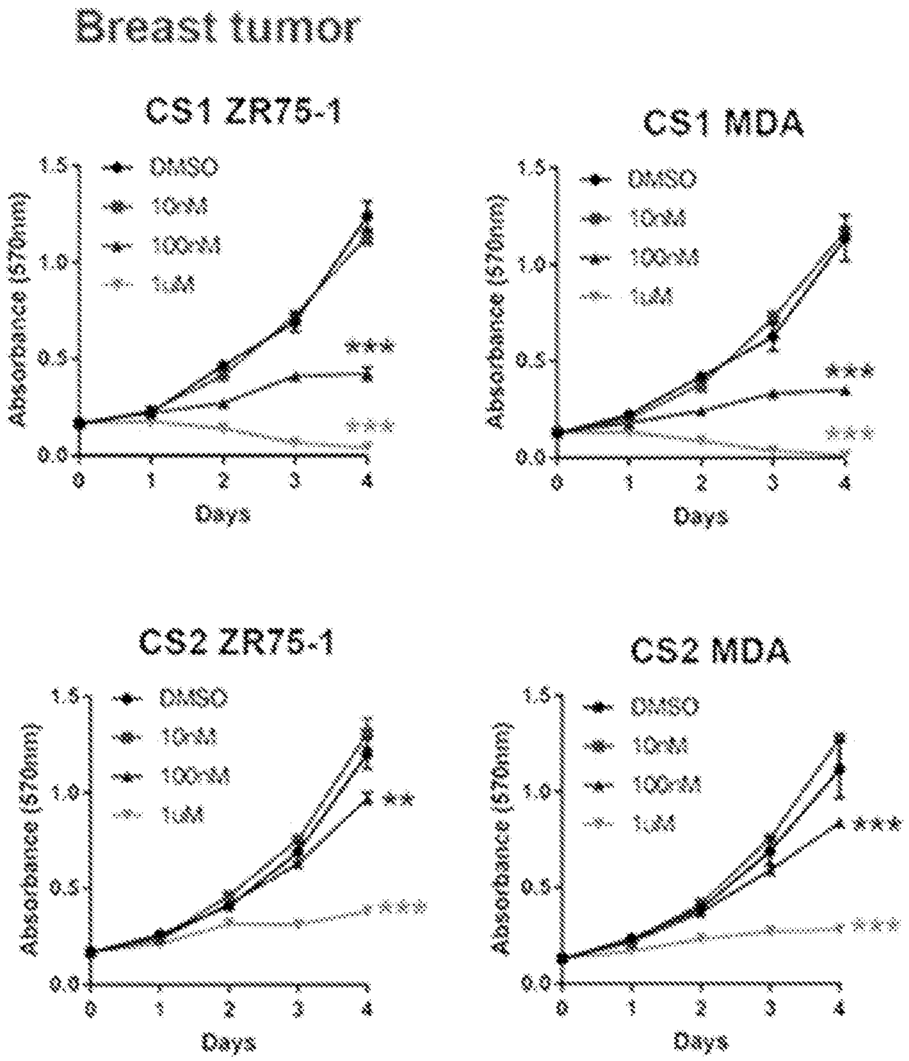
Figure 8D:
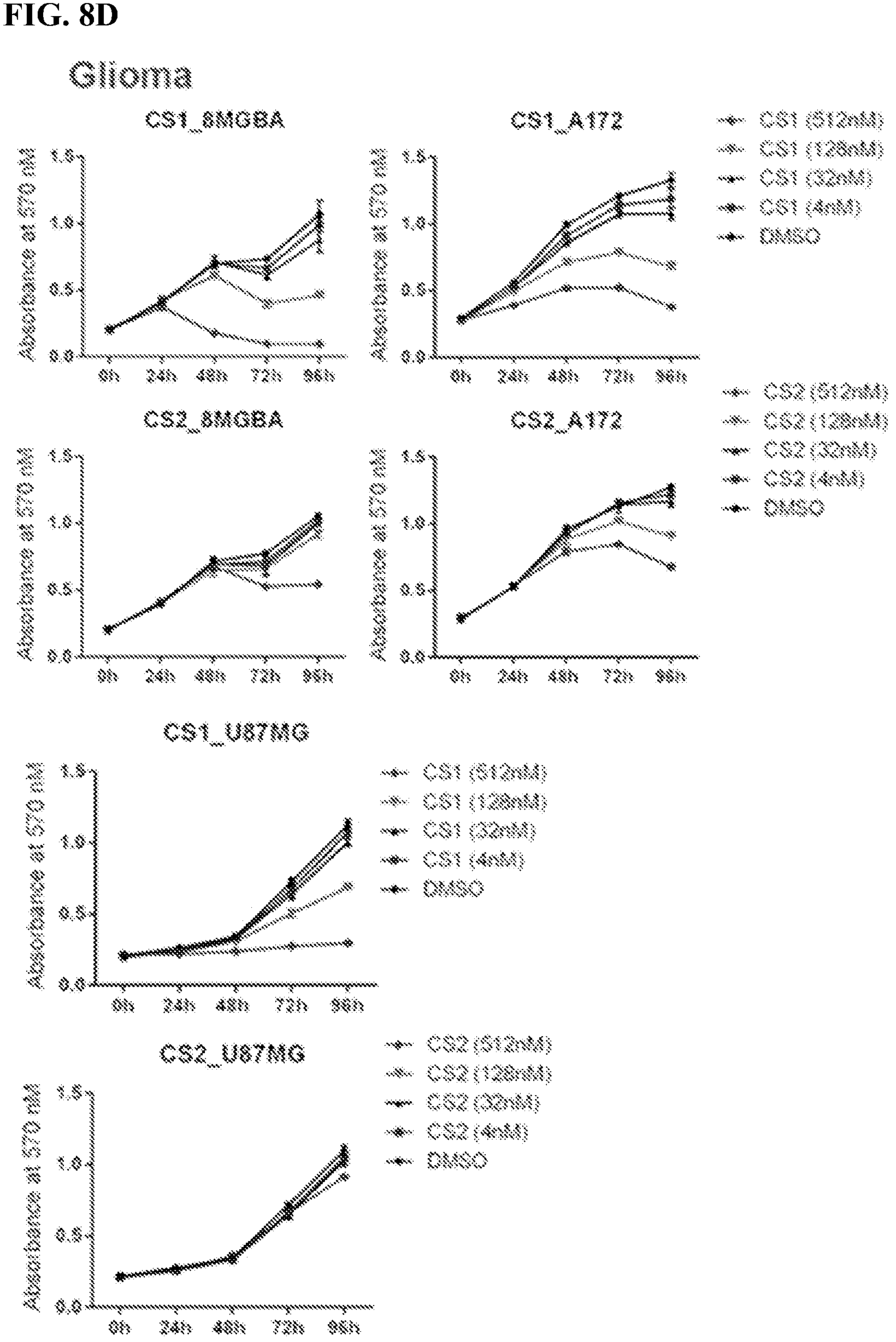

Besides in hematopoietic malignancy, FTO also plays oncogenic function in solid tumors, such as glioblastoma (GBM) and lung squamous cell carcinoma (LUSC). To broaden the application of the FTO inhibitors in additional cancers, expression of FTO in various types of cancers was adopted from cBioPortal for Cancer Genomics (http://www.cbioportal.org/). It was determined that FTO showed high levels in glioma, GBM, breast tumor, pancreas cancer, as well as AML (FIG. 8A). Moreover, treatment with compound of formula (I) or (II) provided growth disadvantage in pancreatic cancer (FIG. 8B), breast tumors (FIG. 8C), and Glioma (FIG. 8D), indicating the anti-tumor effects in solid cancers.

Example 8: Optimization of FTO Inhibitors, Compounds of Formula (I) and (II)

Figure 9A:
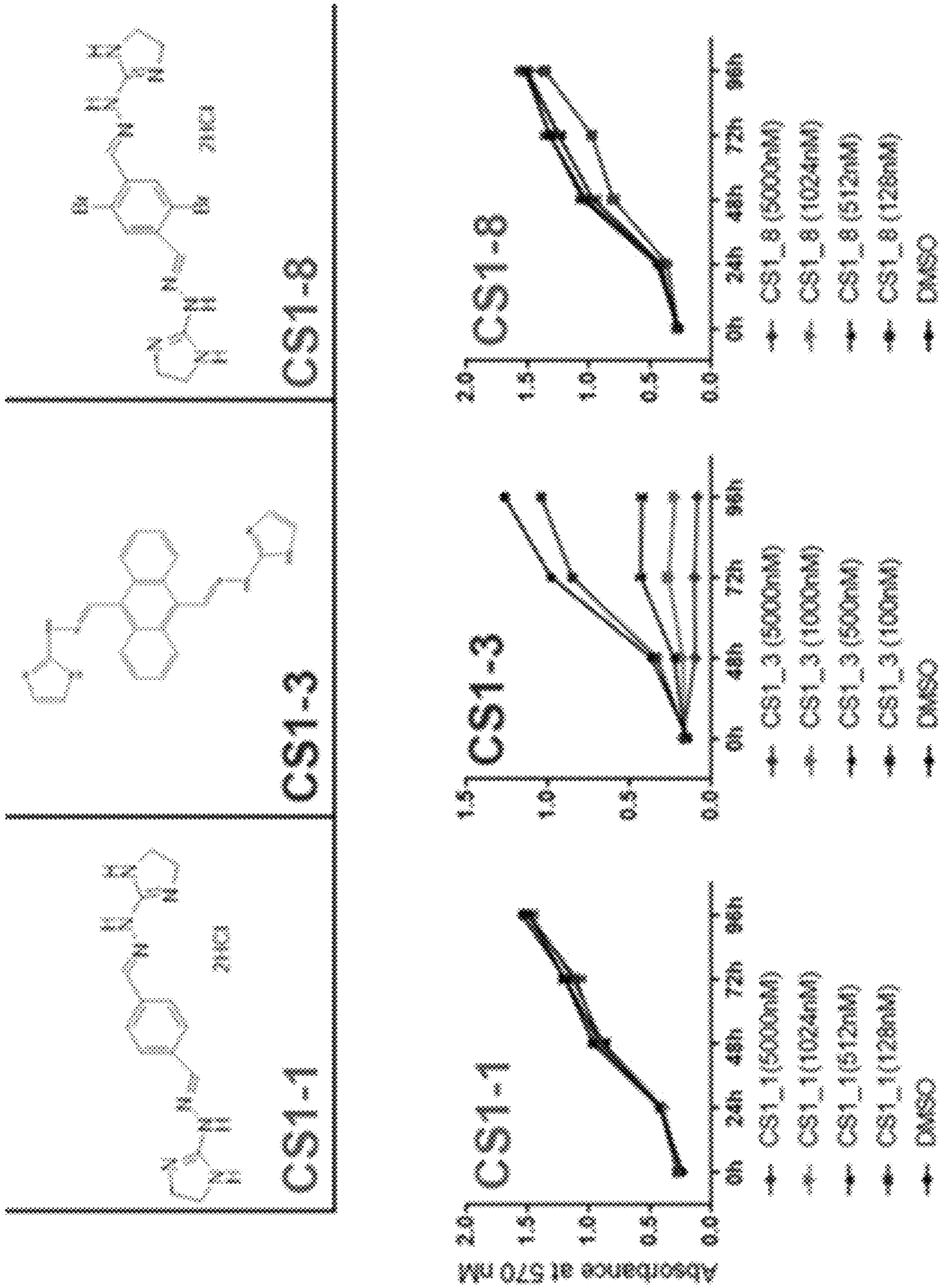
FIGS. 9A-F show effects of 6 analogs of compound of formula (I) (CS1) and 4 analogs of compound of formula (II) (CS2) on proliferation of MONOMAC 6 AML cells.
Figure 9A:
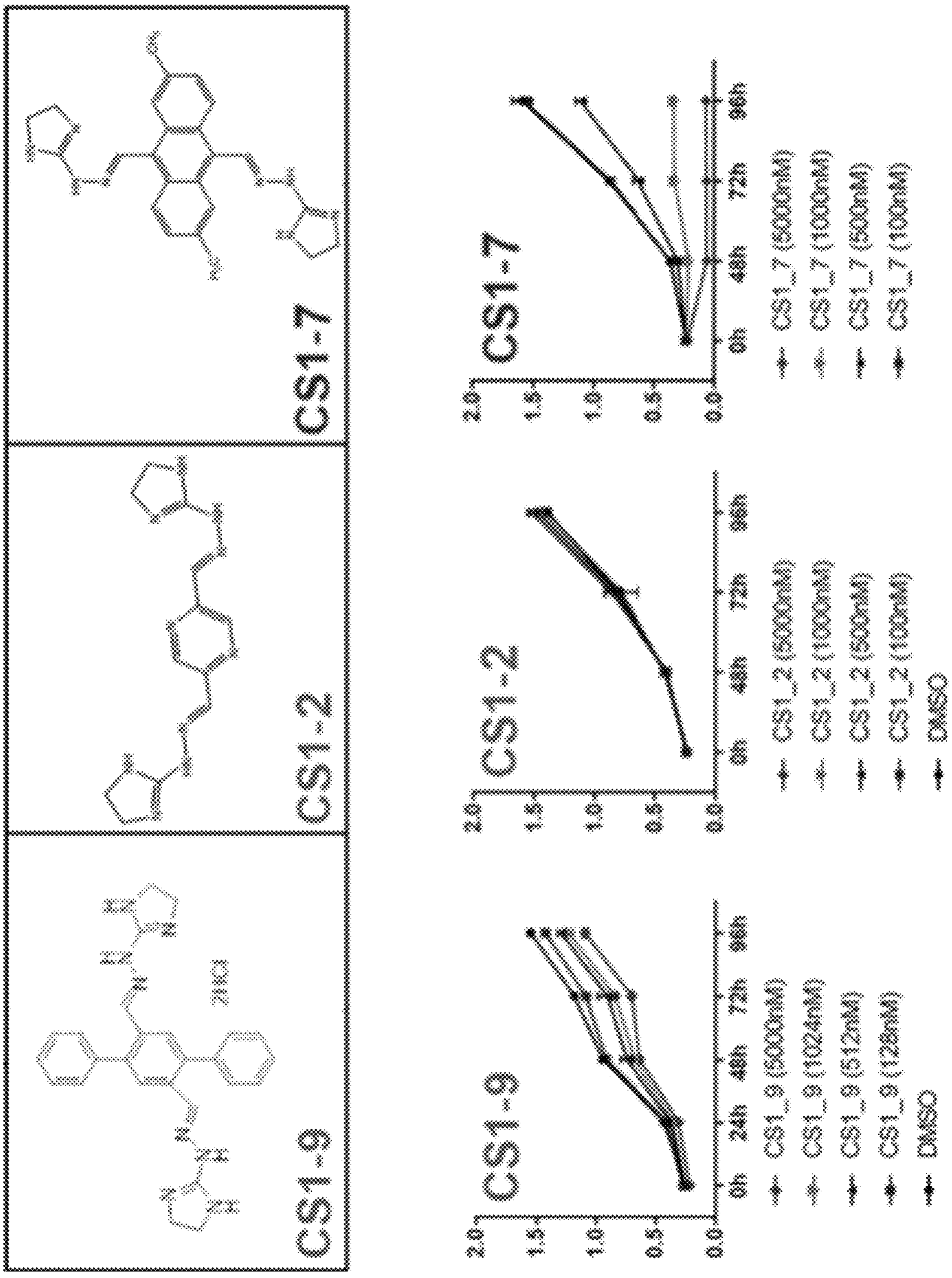

Chemical structures of compounds of formula (I) and (II), were further refined according to their binding pose with FTO proteins, to improve the drug characteristics. FIG. 9A shows the structures of the 6 analogs of compound of formula (I) which have much higher docking scores with FTO protein than compound of formula (I). The analogs were tested for their anti-leukemia activity in MONOMAC 6 AML cells (concentration and cell proliferation were assessed by MTT assay) (FIG. 9A). Two compounds, of formula (Ia) and (Ib), that possess similar or even stronger anti-tumor effects as compared to compound of formula (I) were identified.

Figure 9B:
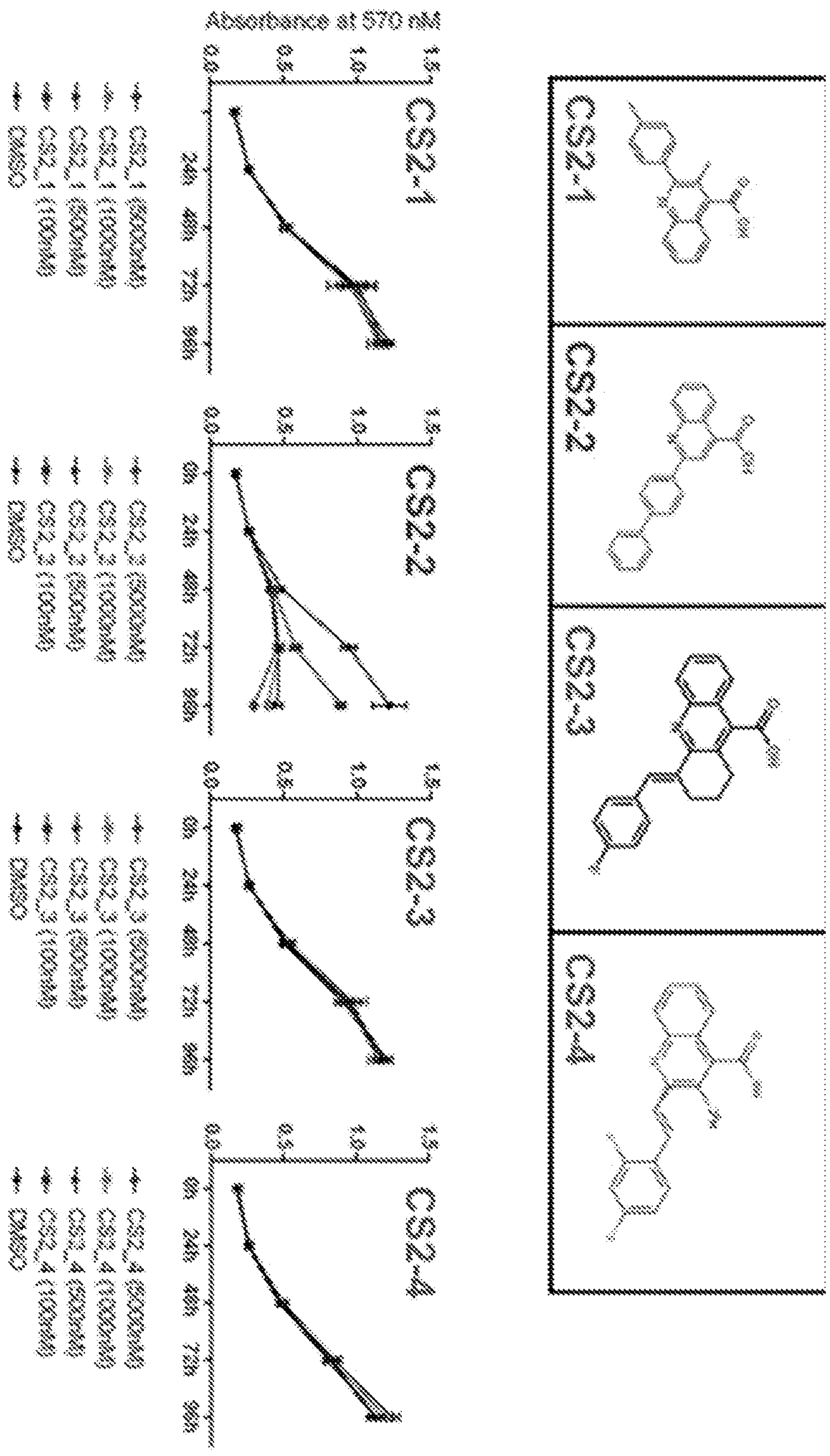

FIG. 9B shows the structures of the 4 analogs of compound of formula (II) which have higher docking scores with FTO protein than compound of formula (II). The analogs were tested for their anti-leukemia activity in MONOMAC 6 AML cells (concentration and cell proliferation were assessed by MTT assay) (FIG. 9B). A compound of formula (IIa) that possesses similar anti-tumor effects as compared to compound of formula (II) was identified.

Figure 9C:
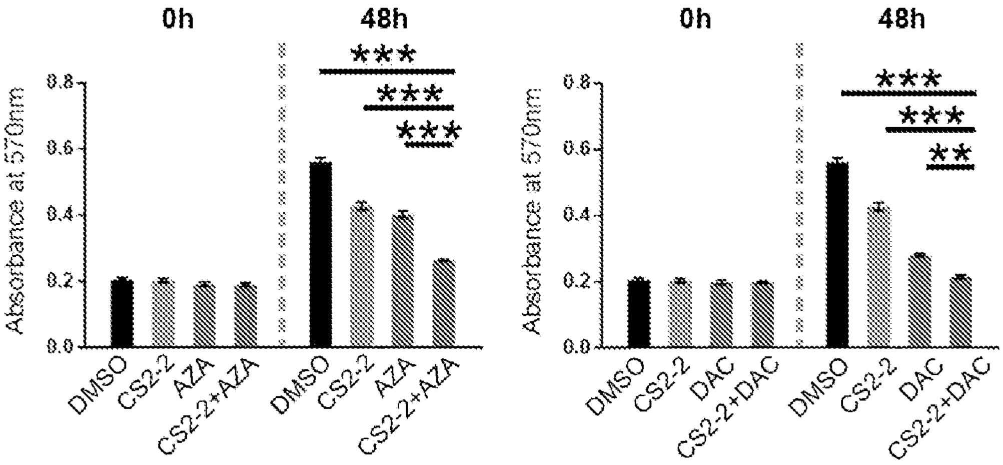

HONO-1 AML cells were treated with 256 nM compound of formula (IIa), 1000 nM AZA, 100 nM DAC, or their combinations for 48 hours. Effects of compound of formula (IIa), DAC, AZA and combined effects of compound of formula (IIa) with either DAC or AZA on HONO-1 AML cell growth was measured (FIG. 9C). Compound of formula (IIa) displayed synergistic effects with DNMT inhibitors AZA and DAC in HONO-1 AML cells.

Figure 9D:
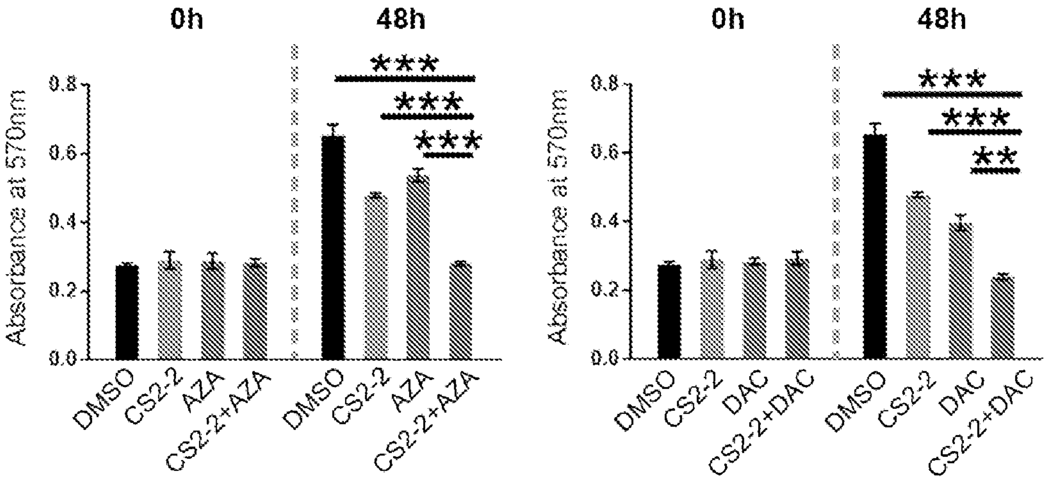

NB4 AML cells were treated with 256 nM compound of formula (IIa), 1000 nM AZA, 100 nM DAC, or their combinations for 48 hours. Effects of compound of formula (IIa), DAC, AZA and combined effects of compound of formula (IIa) with either DAC or AZA on HONO-1 AML cell growth was measured (FIG. 9D). Compound of formula (IIa) displayed synergistic effects with DNMT inhibitors AZA and DAC in NB4 AML cells.

Figure 9E:
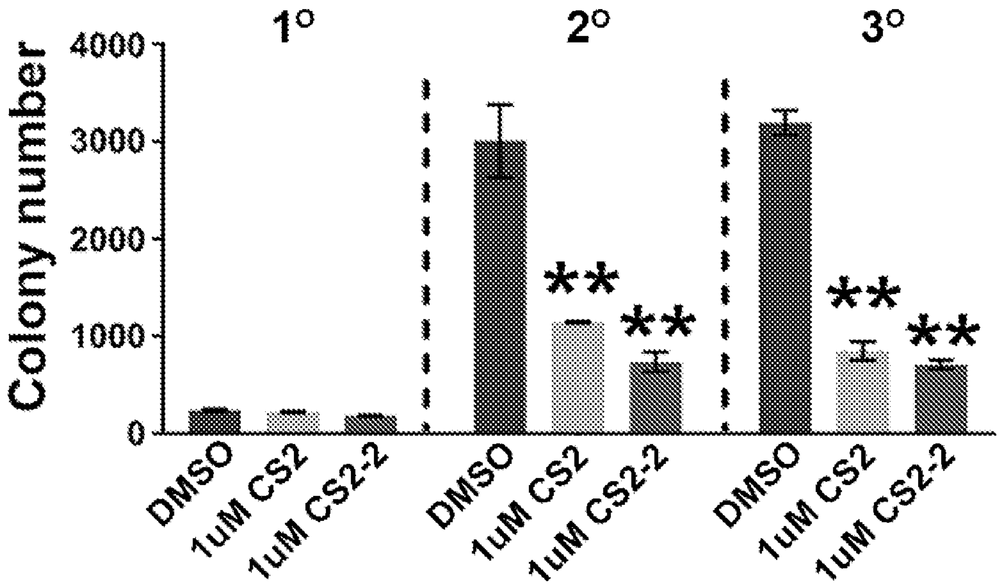
Figure 9F:
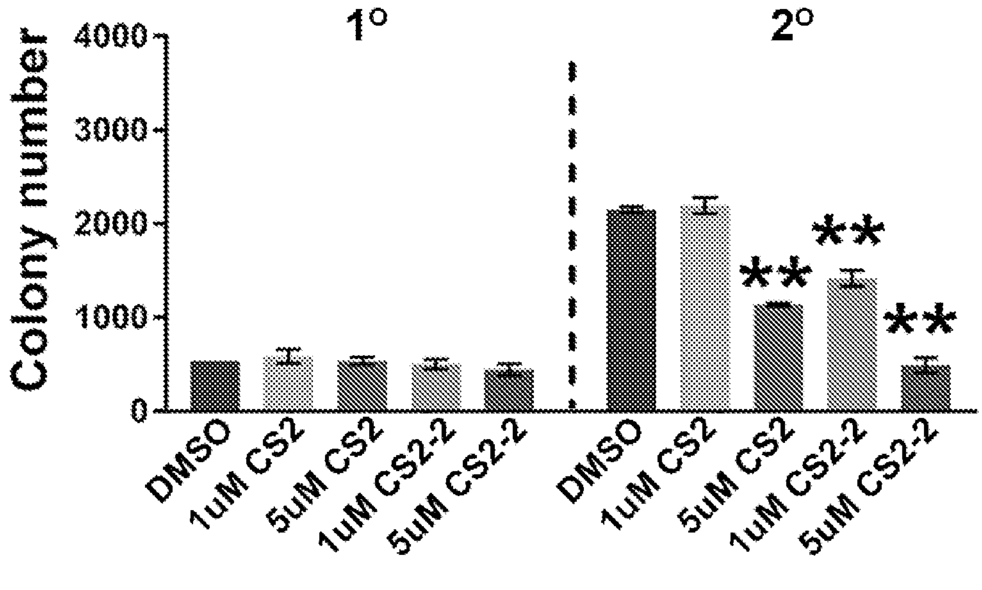

MA9 murine AML cells were treated with 1 μM compound of formula (II) and (IIa), and colony forming activity of the cells was compared. Both compounds exhibited decreased colony forming activity in MA9 murine AML cells, with compound of formula (IIa) exhibiting slightly stronger inhibitory effect (FIG. 9E). Similar experiment was carried out with FLT3ITD-NPM1$^{mut}$ murine cells, which were treated with 10 nM or 50 nM of compound of formula (II) and (IIa). Both compounds exhibited dose dependent decreased colony forming activity in FLT3ITD-NPM1$^{mut}$ murine cells, with compound of formula (IIa) exhibiting slightly stronger inhibitory effect (FIG. 9F).

Example 9: Toxicity of Compounds of Formula (I) and (II) In Vivo

To evaluate the potential drug toxicity of compounds of formula (I) and (II) in vivo, two doses for each compound (5 mg/kg/day (i.e., the does used in the AML mouse model studies) and 20 mg/kg/day) were injected into C57BL/6 mice once every other day for 10 days (similar to the frequency used in the AML mouse model studies). The mice were euthanized 10 days post the last treatment. No significant difference between the drug-treated groups and vehicle-treated control group (Ctrl) were observed on whole body weight and weights of organs (heart, liver, spleen, lung, and kidney). Complete blood count (CBC) data collected from peripheral blood, white blood cell (WBC), red blood cell (RBC), and platelet (PLT) did not show significant differences between the treated groups and control group. Haemotoxylin and Eosin (H&E) staining also showed no difference between the groups. These data suggest that compounds of formula (I) and (II) are safe, at least at a dose that is 4-fold higher than the dose showed potent therapeutic efficacy in preclinical AML mouse models.

Methods

Cell culture: For leukemia cells, U937 and MV4-11 were obtained from American Type Culture Collection (ATCC) and cultured in endotoxin-free RPMI1640 supplemented with 10% fetal bovine serum (FBS) (Gemini Bio-Products); K562 (ATCC) was cultured in IMDM with 10% FBS; NOMO-1, ML-2, NB4 were obtained from DSMZ and kept in RPMI1640 with 10% FBS; SKNO-1 (DSMZ) was maintained in RPMI1640 with 10% FBS and 10 ng/ml GM-CSF; MA9.3ITD (MLL-AF9 plus FLT3-ITD-transformed human CD34$^+$ cord blood) and MA9.3RAS (MLL-AF9 plus NRasG12D-transformed human CD34$^+$ cord blood), established by Dr. James Mulloy (30), were maintained in IMDM supplemented with 20% FBS. AML patient-derived primary cells were kept in IDMD supplemented with 20% FBS, 10 ng/ml human cytokines SCF, TPO, FLT3 ligand, IL-3, and IL-6. The glioblastoma cell lines, including 8MGBA, A172 and U87MG were originally maintained by Dr. David Plas from University of Cincinnati, and cultured in RPMI1640 with 10% FBS. Breast tumor cell lines, including ZR-75-1 and MDA-MB-231, were purchased from ATCC, and cultivated in RPMI1640 with 10% FBS. The cell lines from lung cancer, H1993, H2009, and H1437, and pancreatic cancer cells Capan-1 and miAPACA2 were kindly provided by Dr. Ravi Salgia from City of hope, and maintained in RPMI1640 with 10% FBS. All the cells are not among commonly misidentified cells lines, and were tested for mycoplasma contamination yearly using a PCR Mycoplasma Detection Kit (Applied Biological Materials Inc.). In order to prevent potential contamination, all the mediums were supplemented with Penicillin-Streptomycin (15140122, Life Technologies) and Plasmocin prophylactic (Applied Biological Materials Inc.) according to the manufacture's instruction.

Cell viability and proliferation assay: Cell viability and proliferation were determined with CellTiter 96 Non-Radioactive Cell Proliferation Assay (MTT, G400, Promega). To validate the function of top 213 compounds enriched from structure based virtual screening pipeline, MONOMAC 6 cells were seeded into 96-well plate in the concentration of 10,000 cells/well and treated with 1 M and 5 M in triplicates. Per the manufacture's recommendation, 15 μL dye solution was added into the well at indicated time point. After incubation at 37° C. for 2-4 hours, 100 μL solubilization/Stop Solution was added to quench the reaction. Finally, the absorbance was recorded at 570 on the next day. For the cell proliferation with FTO knockdown stable cells, the indicated AML cells were first infected with pLKO.1-shFTO lentivirus, selected the positive cells with 1 μg/ml puromycin for one week, and then seed into 96-well plate upon treatment with compounds of formula (I) and (II).

Cell cycle and apoptosis assays: Propidium Iodide (PI) DNA staining was chosen to assess the cells located at G0/G1, S, and G2/M stages; while Hoechest 33342 and Pyronin Y was selected to evaluate cells at G0, G1, and S/G2/M phases. For PI staining, $1*10^6$ cells were collected, washed once with PBS, and suspended in 1 ml buffer with 0.05 mg/ml PI, 0.1% trisodium citrate, 0.02 mg/ml ribonuclease A, 0.3% NP-40, incubated at 37° C. for 30 minutes, and then applied to flow cytometer directly. As Hochest 33342/Pyronin Y staining, the cells were collected, washed, and re-suspended in 1 ml cell culture medium, stained with 10 μg/ml Hochest 33342 at 37° C. for 45 minutes, and further stained with 0.5 μg/ml Pyronin Y for additional 15 minutes at 37° C. The samples were transferred onto ice before subjected to flow cytometry. Cell apoptosis was validated with PE Annexin V Apoptosis Detection Kit I (559763, BD Biosciences) according to the instructed protocol. Flow cytometry was performed with Fortessa X20 and the related results were analyzed with FlowJo V10 software.

Secondary bone marrow transplantation (BMT) assays with MLL-AF9 (MA9): For primary BMT assay, mouse bone marrow progenitor cells (herein is lineage negative; Lin$^-$) cells were enriched from 6- to 8-week-old C57BL/6J CD45.2 (B6) mice upon 5-fluorouracil (5-FU) treatment for 5 days with Lineage Cell Depletion Kit (130-090-858, Miltenyi Biotec). The Lin$^-$ progenitor cells were retrovirally transduced with MSCV-Neo-MA9 construct through two rounds of 'spinoculation' as described previously (31). After 7 days of selection with 0.5 mg/ml G418 Sulfate in ColonyGEL (1201, ReachBio Research Lab), the cells were collected and injected into lethally lethally irradiated (960 rads) 8- to 10-week-old B6.SJL (CD45.1) recipient mice with $0.5\times10^6$ donor cells plus $1\times10^6$ 'helper' cells (freshly isolated from the bone marrow of B6.SJL mice without irradiation) for each recipient mouse. For secondary BMT assays, primary leukemic mouse bone marrow cells (CD45.2$^+$) were collected and sorted by flow cytometry when the mice developed full-blown AML. The cells were injected into sub-lethally irradiated (570 rads) secondary recipient mice with $0.1\times10^6$ donor cells per mouse via tail vein injection. One week after BMT, the mice were randomly grouped into compound of formula (I), compound of formula (II), and control groups. The recipient mice were injected with DMSO control, 5 mg/kg compound of formula (I), and 5 mg/kg compound of formula (II), i.p., once per two days, for 20 days.

Xenograft AML mouse models and AML PDX mouse models: NRG-SGM3 mice were used for both 'human-in-mouse' xeno-transplanation models and PDX models. The mice were originally purchased from the Jackson Laboratory, and breeded at core facilities of City of Hope and Cincinnati Children's Hospital according to standard procedures. For xenograft mouse, $0.1\times10^6$ MA9.3ITD cells were transplanted into NRGS recipient mice intravenously. Drug treatment was started from 10 days after transplanatation. Compound of formula (II) was administered through intraperitoneal (i.p.) injection at 5 mg/kg/day, every other day delivery. While β-cyclodextrin enclosed compound of formula (I) was delivered by intravenous injection (i.v.). The successful engraftment was observed following 4 weeks post inoculation displaying a level of about 5% human CD33+ cells in PB.

As PDX mouse models, $1\times10^6$ AML patient derived cells were transplanted into NRGS recipient mice intravenously, and drug treatment was started from 7 days later. Compound of formula (II) and free compound of formula (I) were administered through i.p. injection at 5 mg/kg/day, while micelle enclosed compound of formula (I) was delivered by i.v. injection at 5 mg/kg/day. Both compounds of formula (I) and (II) were injected every other day for ten times in total.

Preparation of compound of formula (I) mPEG-b-PLA Micelle: Methoxy poly(ethylene glycol)-b-poly(D,L-lactide) (mPEG-b-PLA) was purchased from Sigma-Aldorich (900661-500 mg). The film hydration method was employed to prepare the compound of formula (I) loaded polymeric micelle as described previously with some modification (32). In brief, compound of formula (I) and mPEG-b-PLA were dispersed in chloroform accompanying with sonication, respectively. Then, the two chloroform solutions were well-mixed together via vortexing and sonication. After making sure that the mixture was completely dissolved by chloroform, a vacuum-rotary evaporator was applied to evaporate the chloroform and to obtain a compound of formula (I)-loaded polymer film. The thin film was then hydrated with deionized water, followed by vortexing for 2 min and sonication for 5 min. Finally, the hydrated system was processed to centrifuge for 15 min at 5000 rpm to remove the unencapsulated free compound of formula (I). The supernatant was the purified compound of formula (I) loaded mPEG-b-PLA micelle.

Serial colony-forming assay: The assay was employed as described previously with some modification (31). Briefly, the primary murine leukemic cells isolated from bone marrow of AML mice, including MA9 and FLT3ITD/NPM1, were seeded into 35 mm culture dishes (20,000 cells/dish or 10,000 cells/dish) with ColonyGEL plus murine cytokines, including 10 ng/ml IL-3, IL-6, GM-CSF, and 50 ng/ml SCF. The dishes were incubated at 37° C. in a humidified atmosphere of 5% CO2 in air for 7 days. Then, colony cells were collected and replated every 7 days with 20,000 cells/dish for 3 passages. Colony numbers were counted and compared for each passage.

Retrovirus and lentivirus production: Retrovirus infection of murine progenitor cells were employed as described previously (31). The retrovious vectors were transfected into HEK-293T cells using Effectene Transfection Reagent (301427, Qiagen, Valencia, CA) together with packaging vector pCL-ECO. The retrovirus were collected at 48 and 72 hours post transfection, and added into mouse progenitor cells in the presence of polybrene for 'spinoculation'.

Lentivirus used to overexpression and knockdown of a specific gene were packaged with pMD2.G, pMDLg/pRRE and pRSV-Rev (purchased from Addgene). Briefly, 1.5 μg pMD2.G, 0.9 μg pMDLg/pRRE, 2.1 μg pRSV-Rev and 5 μg constructs were co-transfected into Lenti-X 293T cells in 100 mm cell culture dish with Effectene Transfection Reagent. The lentivirus particles were harvested at 48 and 72 hours after transfection, concentrated with PEG-it Virus Precipitation Solution (#LV810A-1, SBI), and finally used to infect leukemic cells with existence of polybrene.

RNA extraction, cDNA synthesis and qPCR: Total RNA samples were isolated with miRNeasy Mini Kit (217004, Qiagen) according to the manufacturer's guidelines. As cDNA synthesis, 200-1,000 ng total RNA or immunoprecipitated RNA samples were used for reverse transcription in 10 μl reaction volume with QuantiTect Rev. Transcription Kit (205314, Qiagen). And quantitative PCR (qPCR) was performed with Maxima SYBR Green qPCR Master Mix (2×) (FEPK0253, Thermo Fisher) in an AB 7900HT Fast Real-Time PCR system (Applied Biosystem). GAPDH or ACTB were used as endogenous control and each reaction was run in triplicates. All the primers were listed in XXX.

$m^6A$ dot blot assay: To determine global $m^6A$ abundance, $m^6A$ dot blot assay were employed with poly(A)$^+$ RNA as described previously (33). poly(A)$^+$ RNA was enriched from total RNA with polyATract mRNA isolation system IV (Z5310, Promega).

Protein extraction and Western Blot assay: The total protein were extracted from cell pellet with RIPA buffer (R0278, Sigma-Aldrich) plus Halt phosphatase inhibitor cocktail (78420, Thermo Fisher Scientific) and Halt protease inhibitor cocktail (78429, Thermo Fisher Scientific). Western blot assay was performed as described previously (33). Antibodies used for Western blot were as follows unless otherwise specified: FTO (ab124892, Abcam), GAPDH (sc-47724, Santa Cruz Biotechnology), PD-L1 (66248, Proteintech), and PD-L2 (329608, BioLgend).

Flow cytometry analysis: Flow cytometry analysis with surface markers was conducted as described previously with some modifications (33). Antibodies used include anti-mouse CD45.2-PE (12-0454-83, Thermo Fisher Scientific), anti-Human CD33 PE (12-0339-42, Thermo Fisher Scientific), PE anti-mouse/human CD11b antibody, anti-Human CD15 APC (17-0158-42, eBioscience), and anti-Human CD34 FITC (11-0349-42, eBioscience).

Intracellular staining: For intracellular staining with FTO, we first labeled the human primary cells with CD34 surface marker. The cells were washed with chilled PBS, re-suspended in 4% paraformaldehyde (PFA) at a density of $2\times10^6$ cells/ml, and incubated at 4° C. for 20 minutes with rotation. After fixation, the cells was gently re-suspended in 5× Permeabilization buffer (00-8333, eBioscience), stained with anti-FTO (1:100) for 1 hour on ice. Finally, the cells were washed twice with 1× Permeabilization buffer, incubated with anti-rabbit IgG (H+L) (Alexa Fluor 555 Conjugate, 4413S, Cell Signaling Technology) in 5× Permeabilization buffer for 30 minutes at room temperature, and stored in 200 μl of FACS buffer for analysis.

$m^6A$ demethylase assay in cell free system: To determine whether compounds of formula (I) and (II) could directly disturb the $m^6A$ demethylation activity of FTO protein, $m^6A$ demethylase assay was conducted with $m^6A$ demethylase assay kit (ab233489, Abcam) following the manufacturer's protocol with minor modifications. Recombinant FTO protein was purchased from Active Motif (31572). For the enzymatic reaction, we added 44 μl of final demethylase buffer, 1 μl (0.5 μg) of purified FTO protein, and 5 μl of inhibitor solution with indicated concentration and incubated the strip plate at 37° C. for 90 minutes. For the final signal detection, we added 100 μl of developer solution to each well and incubated at room temperature for 3 minutes away from light before subjected to 100 μl of stop solution. The absorbance was recorded at 450 nm immediately.

The FTO demethylase activity (OD/h/mg) in each well was determined by the following formula:

$$\text{Demethylase activity} \frac{[OD(\text{control} - \text{blank}) - OD(\text{inhibitor sample} - \text{blank})]}{[\text{Protein Amount } \mu g/1000] \times 1.5 \text{ hour}}$$

The relative inhibition on FTO demethylase was calculated by the following equation:

$$\% \text{ Inhibition} = 100\% \times \left(1 - \frac{OD(\text{control} - \text{blank}) - OD(\text{inhibitor sample} - \text{blank})]}{[OD(\text{control} - \text{blank}) - OD(\text{no inhibitor sample} - \text{blank})]}\right.$$

Cross-Linking Immunoprecipitation and qPCR (CLIP-qPCR): CLIP-qPCR analysis to validate the interactions between FTO/YTHDF2 and their targets mRNAs was performed as previously with some modifications. Briefly, cells in 150 mm culture plates with 80% confluence were washed once with ice-cold PBS, cross-linked by UV with 150 mJ/cm$^2$ (254 nm), and harvested by trypsinization. The nuclear fraction was isolated with XXX buffer, lysed in XXX buffer for sonication. For each reaction, 50 μl Protein A/G magnetic beads (88803, Thermo Fisher Scientific) were added to pre-clear nuclear lysates. In the meantime, Flag (F3165, Sigma-Aldrich) antibody and negative control IgG antibody (CS200621, Millipore) were conjugated to Protein A/G magnetic Beads by incubation for 4 hours at 4° C. The conjugated beads were washed three times with RNA immunoprecipitation (RIP) buffer (150 mM KCl, 25 mM Tris (pH 7.4), 5 mM EDTA, 0.5 mM DTT, 0.5% NP40, lx protease inhibitor, incubated with pre-cleared nuclear extraction at 4° C. overnight. After washed three times with RIP buffer, the beads were incubated with RNase-free DNase I for 15 minutes at 37° C., and Proteinase K for 15 minutes at 37° C. before quenched by QIAzol lysis reagent (79306, Qiagen). The Input RNA and immunoprecipitated RNA were recovered by QIAzol extraction, and dissolved with 12 μl RNase-free water. 4 μl purified RNA from each group was used for reverse transcription and qPCR.

mRNA sequencing: Total RNA samples were isolated from NOMO-1 cells upon treatment with compounds of formula (I) or (II) and FTO knockdown with miRNeasy Mini Kit for sequencing. RNA concentration was measured by NanoDrop 1000 (Thermo Fisher Scientific, Waltham Massachusetts, US) and RNA integrity was determined with Bioanalyzer (Agilent). Each RNA sample was spiked in with an appropriate amount of either Mix1 or Mix2 according to Life Technologies' guidelines which would lead to about 1% of the total number of RNA-Seq reads mapping to the 92 ERCC control sequences, assuming the mRNA fraction in the total RNA is 2%. Library construction of 300 ng total RNA for each sample was made using KAPA Stranded mRNA-Seq Kit (Illumina Platforms) (Kapa Biosystems, Wilmington, USA) with 10 cycles of PCR amplification. Libraries were purified using AxyPrep Mag PCR Clean-up kit (Thermo Fisher Scientific). Each library was quantified using a Qubit fluorometer (Life Technologies) and the size distribution assessed using the 2100 Bioanalyzer (Agilent Technologies, Santa Clara, USA). Sequencing was performed on an Illumina® Hiseq 2500 (Illumina, San Diego, CA, USA) instrument using the TruSeq SR Cluster Kit V4-cBot-HS (Illumina®) to generate 51 bp single-end reads sequencing with v4 chemistry. Quality control of RNA-Seq reads was performed using FastQC. Differential gene expression was analyzed by standard Illumina sequence analysis pipeline. Each group contains 3-4 replicates. Gene Set Enrichment Analysis (GSEA) was used to analyze the signal pathway enrichment in different groups of samples. Circos and Integrative Genomics Viewer (IGV) were used to visualize specific gene.

Quantification and statistical analysis: Data were analyzed with GrapPad Prism 7 and were presented as mean±SEM or mean±SD as indicated. Two-tailed Student's t test was used to compare means between groups as indicated; $P<0.05$ was considered significant. Kaplan-Meier survival curves were plotted with GraphPad Prism 7 and the P values were calculated using the log rank test. For Western blot results, representative figures from three biological replicates were shown. Densitometry analysis of the bands from Western blot were performed with Gel-Pro analyzer and normalized to the loading controls.

REFERENCES

1. Boccaletto, P. et al. MODOMICS: a database of RNA modification pathways. 2017 update. *Nucleic Acids Res* 46, D303-D307 (2018).
2. Frye, M., Harada, B. T., Behm, M. & He, C. RNA modifications modulate gene expression during development. *Science* 361, 1346-1349 (2018).
3. Jia, G. et al. N6-methyladenosine in nuclear RNA is a major substrate of the obesity-associated FTO. *Nat Chem Biol* 7, 885-7 (2011).
4. Jia, G., Fu, Y. & He, C. Reversible RNA adenosine methylation in biological regulation. *Trends Genet* 29, 108-15 (2013).
5. Frayling, T. M. et al. A common variant in the FTO gene is associated with body mass index and predisposes to childhood and adult obesity. *Science* 316, 889-94 (2007).
6. Hernandez-Caballero, M. E. & Sierra-Ramirez, J. A. Single nucleotide polymorphisms of the FTO gene and cancer risk: an overview. *Mol Biol Rep* 42, 699-704 (2015).
7. Deng, X., Su, R., Stanford, S. & Chen, J. Critical Enzymatic Functions of FTO in Obesity and Cancer. *Front Endocrinol* (*Lausanne*) 9, 396 (2018).
8. Li, Z. et al. FTO Plays an Oncogenic Role in Acute Myeloid Leukemia as a N(6)-Methyladenosine RNA Demethylase. *Cancer Cell* 31, 127-141 (2017).
9. Dang, L. et al. Cancer-associated IDH1 mutations produce 2-hydroxyglutarate. *Nature* 462, 739-44 (2009).
10. Ward, P. S. et al. The common feature of leukemia-associated IDH1 and IDH2 mutations is a neomorphic enzyme activity converting alpha-ketoglutarate to 2-hydroxyglutarate. *Cancer Cell* 17, 225-34 (2010).
11. Su, R. et al. R-2HG Exhibits Anti-tumor Activity by Targeting FTO/m(6)A/MYC/CEBPA Signaling. *Cell* 172, 90-105 e23 (2018).
12. Niu, Y. et al. RNA N6-methyladenosine demethylase FTO promotes breast tumor progression through inhibiting BNIP3. *Mol Cancer* 18, 46 (2019).
13. Liu, J. et al. m(6)A demethylase FTO facilitates tumor progression in lung squamous cell carcinoma by regulating MZF1 expression. *Biochem Biophys Res Commun* 502, 456-464 (2018).

14. Tang, X., Liu, S., Chen, D., Zhao, Z. & Zhou, J. The role of the fat mass and obesity-associated protein in the proliferation of pancreatic cancer cells. *Oncol Lett* 17, 2473-2478 (2019).
15. Shen, X. P. et al. Low expression of microRNA-1266 promotes colorectal cancer progression via targeting FTO. *Eur Rev Med Pharmacol Sci* 22, 8220-8226 (2018).
16. Xu, D. et al. FTO expression is associated with the occurrence of gastric cancer and prognosis. *Oncol Rep* 38, 2285-2292 (2017).
17. Yan, F. et al. A dynamic N(6)-methyladenosine methylome regulates intrinsic and acquired resistance to tyrosine kinase inhibitors. *Cell Res* 28, 1062-1076 (2018).
18. Chen, B. et al. Development of cell-active N6-methyladenosine RNA demethylase FTO inhibitor. *J Am Chem Soc* 134, 17963-71 (2012).
19. Huang, Y. et al. Meclofenamic acid selectively inhibits FTO demethylation of m6A over ALKBH5. *Nucleic Acids Res* 43, 373-84 (2015).
20. Zheng, G. et al. Synthesis of a FTO inhibitor with anticonvulsant activity. *ACS chemical neuroscience* 5, 658-65 (2014).
21. Singh, B. et al. Important Role of FTO in the Survival of Rare Panresistant Triple-Negative Inflammatory Breast Cancer Cells Facing a Severe Metabolic Challenge. *PLoS ONE* 11, e0159072 (2016).
22. Wang, T. et al. Fluorescein Derivatives as Bifunctional Molecules for the Simultaneous Inhibiting and Labeling of FTO Protein. *J Am Chem Soc* 137, 13736-9 (2015).
23. Toh, J. D. W. et al. A strategy based on nucleotide specificity leads to a subfamily-selective and cell-active inhibitor of N6-methyladenosine demethylase FTO. *Chem. Sci.* 6, 112-122 (2015).
24. He, W. et al. Identification of A Novel Small-Molecule Binding Site of the Fat Mass and Obesity Associated Protein (FTO). *J Med Chem* 58, 7341-8 (2015).
25. Padariya, M. & Kalathiya, U. Structure-based design and evaluation of novel N-phenyl-1H-indol-2-amine derivatives for fat mass and obesity-associated (FTO) protein inhibition. *Comput Biol Chem* 64, 414-425 (2016).
26. Huang, Y. et al. Small-molecule targeting of oncogenic FTO demethylase in acute myeloid leukemia. *Cancer Cell* 35, 677-691 (2019).
27. Issa, J. P. et al. Phase 1 study of low-dose prolonged exposure schedules of the hypomethylating agent 5-aza-2'-deoxycytidine (decitabine) in hematopoietic malignancies. *Blood* 103, 1635-40 (2004).
28. Dombret, H. et al. International phase 3 study of azacitidine vs conventional care regimens in older patients with newly diagnosed AML with >30% blasts. *Blood* 126, 291-9 (2015).
29. Yang, H. et al. Expression of PD-L1, PD-L2, PD-1 and CTLA4 in myelodysplastic syndromes is enhanced by treatment with hypomethylating agents. *Leukemia* 28, 1280-8 (2014).
30. Wunderlich, M. et al. AML cells are differentially sensitive to chemotherapy treatment in a human xenograft model. *Blood* 121, e90-7 (2013).
31. Li, Z. et al. Overexpression and knockout of miR-126 both promote leukemogenesis. *Blood* 126, 2005-15 (2015).
32. Gao, M. et al. Stereoselective Stabilization of Polymeric Vitamin E Conjugate Micelles. *Biomacromolecules* 18, 4349-4356 (2017).
33. Su, R. et al. R-2HG Exhibits Anti-tumor Activity by Targeting FTO/m(6)A/MYC/CEBPA Signaling. *Cell* 172, 90-105 e23 (2018).

What is claimed is:

1. A method of treating cancer in a subject in need thereof, the method comprising measuring an elevated Fat Mass and Obesity-Associated Protein (FTO) level compared to a control in a biological sample obtained from the subject and administering a therapeutically effective amount of a compound of formula (I):

(I)

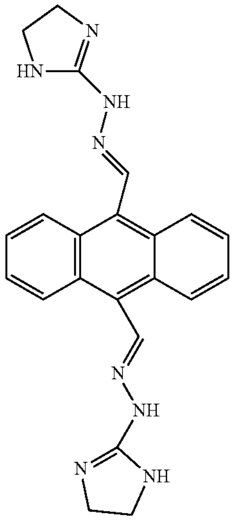

or a pharmaceutically acceptable salt thereof, wherein (i) the cancer is leukemia and the biological sample is a blood sample, or (ii) the cancer is a solid tumor and the biological sample is a tumor sample, wherein the solid tumor is breast cancer, pancreatic cancer, glioma or glioblastoma and the leukemia is acute myeloid leukemia (AML).

2. The method of claim 1, wherein the blood sample is a peripheral blood sample.

3. A method of treating cancer in a subject in need thereof, the method comprising administering a therapeutically effective amount of a Fat Mass and Obesity-Associated Protein (FTO) inhibitor to a subject in need thereof, wherein the FTO inhibitor is a compound of formula (I):

(I)

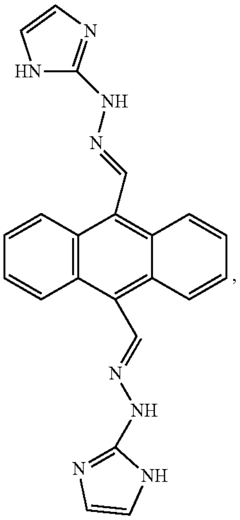

or a pharmaceutically acceptable salt thereof, and wherein the cancer is AML with an elevated FTO level compared to a control, pancreatic cancer with an elevated FTO level compared to a control, breast cancer with an elevated FTO level compared to a control, glioma with an elevated FTO level compared to a control or glioblastoma with an elevated FTO level compared to a control.

* * * * *